(12) United States Patent
Von Hoff et al.

(10) Patent No.: US 8,394,742 B2
(45) Date of Patent: Mar. 12, 2013

(54) METHODS, COMPOUNDS AND COMPOSITIONS WITH GENOTYPE SELECTIVE ANTICANCER ACTIVITY

(75) Inventors: Daniel D. Von Hoff, Scottsdale, AZ (US); Haiyong Han, Chandler, AZ (US); Hong Wang, East Brunswick, NJ (US); Gary A. Flynn, Oro Valley, AZ (US)

(73) Assignees: The Translation Genomics Research Institute, Phoenix, AZ (US); The Arizona Board of Regents on Behalf of the University of Arizona, Tucson, AZ (US)

( * ) Notice: Subject to any disclaimer, the term of this patent is extended or adjusted under 35 U.S.C. 154(b) by 1137 days.

(21) Appl. No.: 11/910,591

(22) PCT Filed: Apr. 14, 2006

(86) PCT No.: PCT/US2006/013900
§ 371 (c)(1), (2), (4) Date: Aug. 26, 2008

(87) PCT Pub. No.: WO2006/113367
PCT Pub. Date: Oct. 26, 2006

(65) Prior Publication Data
US 2009/0137420 A1 May 28, 2009

Related U.S. Application Data

(60) Provisional application No. 60/671,758, filed on Apr. 15, 2005.

(51) Int. Cl.
*C40B 30/06* (2006.01)
*C12N 15/11* (2006.01)

(52) U.S. Cl. ....................... 506/10; 514/44 A

(58) Field of Classification Search ................ None
See application file for complete search history.

(56) References Cited

U.S. PATENT DOCUMENTS

| | | | |
|---|---|---|---|
| 4,282,309 A * | 8/1981 | Laridon et al. | 430/281.1 |
| 6,646,232 B2 | 11/2003 | Richards et al. | |
| 2002/0132340 A1 | 9/2002 | Waldman | |
| 2003/0018245 A1 | 1/2003 | Kaufman et al. | |
| 2004/0018624 A1 | 1/2004 | Harrington et al. | |
| 2004/0248221 A1 * | 12/2004 | Stockwell | 435/7.23 |

FOREIGN PATENT DOCUMENTS

| | | |
|---|---|---|
| WO | 9807849 | 2/1998 |
| WO | 0009526 | 2/2000 |
| WO | 0050439 | 8/2000 |
| WO | 03027260 | 4/2003 |

(Continued)

OTHER PUBLICATIONS

Wang et al., Proc. Amer. Assoc. Cancer Res., 2004, Vol.*

(Continued)

*Primary Examiner* — Christopher M Gross
*Assistant Examiner* — Jeremy C Flinders
(74) *Attorney, Agent, or Firm* — Rodney J. Fuller; Booth Udall Fuller, PLC

(57) ABSTRACT

This invention is directed to methods for screening and identification of compounds capable of selectively eliminating cancer cells with specific loss-of-function alterations, including but not limited to mutations, deletions, hypermethylations, and other types of gene silencing. This invention is also directed to novel compounds that selectively eliminate cancer cells with specific loss-of-function alterations. Furthermore, this invention is directed to methods for production and therapeutic use of compounds that selectively eliminate cancer cells with specific loss-of-function alterations.

16 Claims, 23 Drawing Sheets

FOREIGN PATENT DOCUMENTS

WO 03089580 10/2003

OTHER PUBLICATIONS

Paddison et al., Genes & Development, 2002, 16:948-958.*
Aaronson, Science, 1991, 254:1146-1153.*
Torrance et al., Nat. Biotech., 2001, 19:940-945.*
Basco et al., Oncology, 2004, 67:277-290.*
Koyama et al., Mutation Research Genomics, 1999, 406:71-77.*
Brummelkamp et al., "A system for stable expression of short interfering RNAs in mammalian cells," Science 296, Apr. 19, 2002, 550-553.
Tascilar et al., "The SMAD4 protein and prognosis of pancreatic ductal adenocarcinoma," Clinical Cancer Res 7, Dec. 2001. 4115-4121.

* cited by examiner

Figure 3
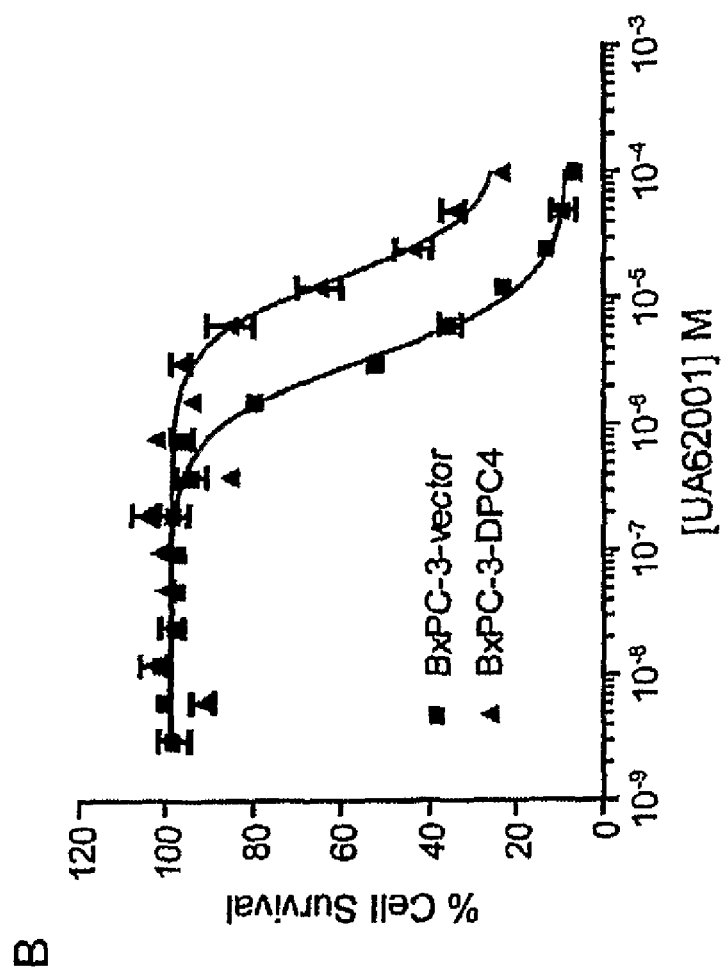
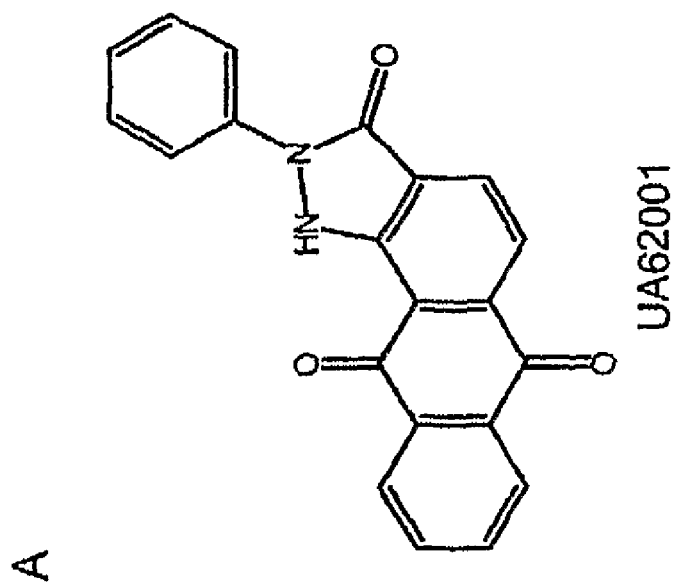

Figure 6

IC$_{50}$ values of UA62001 in pancreatic cancer cell lines and primary cells

| Cell line | BxPC-3 | AsPC-1 | Capan-1 | Capan-2 | CFPAC-1 | Hs 766T | MIA PaCa-2 | PANC-1 | SU.86.8 6 | HPDE6 | Forf | IMR-90 |
|---|---|---|---|---|---|---|---|---|---|---|---|---|
| UA62001 | 3.2[a] | 14.8[c] | 10.8[b] | 4.7[a] | 6.4[a] | 3.7[a] | 3.5[a] | 18.7[c] | 6.5[a] | 92.3 | >>200 | >>200 |
| DPC4 Status | HD | Wt/Mut | Mut (343Stop) | Wt (low expression) | HD | HD | Wt | Wt | Wt | Wt | Wt | Wt |
| References | (4, 21, 39) | (42, 43) | (39, 42) | (41) | (4, 21, 39, 42) | (4, 39) | (40) | (39, 42, 43) | | (18, 19) | (17) | (52) |

The table lists the average μM concentration required to achieve 50% inhibition in MTS assay in each cell line (IC$_{50}$s were calculated by GraphPad Prism 4, GraphPad Software Inc.) from three different cytotoxicity tests. HD, homozygous deletion; W', absence of the genetic alteration; Mut, Mutations (amino acids involved were indicated in the parenthesis). There are significant differences among the three groups (a, b and c) of IC$_{50}$ values (P value < 0.05 calculated using one-way ANOVA).

Figure 7

Comparison between Agilent microarray data and real-time quantitative RT-PCR data

| Functional complexes in cell cycle | Gene Name | Accession number | Oligo array data (ratio, treatment/control) | | Real-time PCR data (ratio, treatment/control) | |
|---|---|---|---|---|---|---|
| | | | BxPC-3-vector | BxPC-3-DPC4 | BxPC-3-vector | BxPC-3-DPC4 |
| Cyclin B/CDC2 | CCNB1 | NM_031966 | 0.56 (12.5%) | 0.64 | 0.23 (30.3%) | 0.33 |
| | CCNB2 | NM_004701 | 0.46 (14.8%) | 0.54 | 0.18 (41.9%) | 0.31 |
| | CDC2 | NM_001786 | 0.54 (20.6%) | 0.68 | 0.23 (67.6%) | 0.71 |
| MCM complex | MCM2 | NM_004526 | 0.54 (12.9%) | 0.62 | 0.28 (61.1%) | 0.72 |
| | MCM3 | NM_002388 | 0.38 (20.8%) | 0.48 | 0.13 (61.8%) | 0.34 |
| | MCM4 | NM_005914 | 0.47 (21.7%) | 0.60 | 0.47 (36.5%) | 0.74 |
| | MCM5 | NM_006739 | 0.45 (25.0%) | 0.60 | 0.14 (48.1%) | 0.27 |
| | MCM6 | NM_005915 | 0.31 (26.2%) | 0.42 | 0.16 (54.3%) | 0.35 |
| | MCM7 | NM_005916 | 0.44 (13.7%) | 0.51 | 0.28 (31.7%) | 0.41 |

Real-time quantitative RT-PCR was performed to validate the transcript changes of the genes of cyclin B/CDC2 and MCM complexes, measured by Agilent microarray analysis, in DPC4 isogenic cell lines in response to UA62001 treatment. The percentage values in parentheses represent the ratio (treatment/control) difference of each gene involved in cyclin B/CDC2 or MCM complex between the DPC4 isogenic cell lines.

A

Targeted sequences for DPC4 suppression

Oligo1: 138 5'ATGTCTATTACGAATACAC3' 156
Oligo2: 413 5'TGCCCGTCTCTGGAGGTGG3' 431
Oligo3: 691 5'ATCGTGCATCGACAGAGAC3' 709
Oligo4: 939 5'GTAGGACTGCACCATACAC3' 958
Oligo5: 1221 5'GGTCAACTCTCCAATGTCC3' 1239
Oligo6: 1265 5'AGCAAGGTTGCACATAGGC3' 1281

B

Figure 13
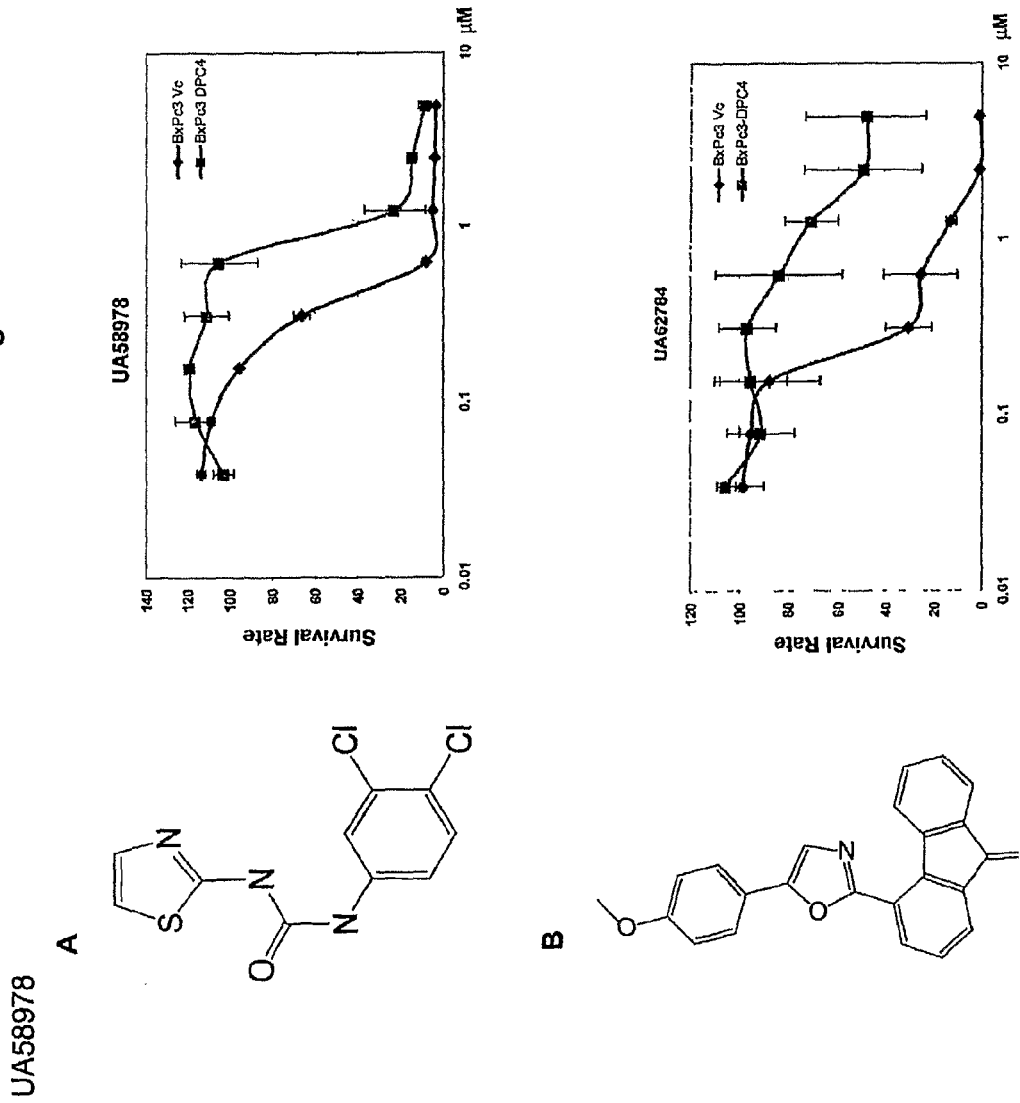
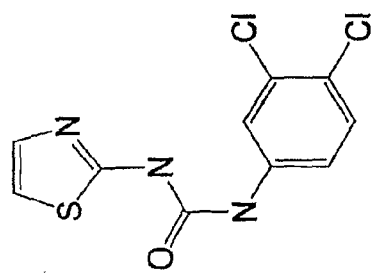
UA58978
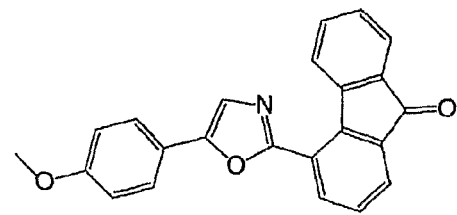
UA62784

Figure 14

UA62784 Molecular Properties

| UA62784 Properties | | Lipinski's Role of 5 | |
|---|---|---|---|
| cLogP: | 5.429 | LogP: | ≤ 5.0 |
| TPSA: | 52.337 | MW: | ≤ 500 |
| MW: | 353.376 | nON: | ≤ 10(2*5) |
| nON: | 4 | nOHNH: | ≤ 5 |
| nOHNH: | 0 | | |
| Nviolations: | 1 | | |
| Nrotb: | 3 | | |

Figure 15

IC50 values

| | BxPC-3 | AsPC-1 | Capan-1 | Capan-2 | CFPac-1 | Hs766T | MIAPaCa-2 | PANC-1 | SU.86 | Forf | IMR-90 |
|---|---|---|---|---|---|---|---|---|---|---|---|
| UA62784 | 0.004 | 0.029 | 0.046 | 0.012 | 0.005 | 0.012 | 0.0025 | 0.0058 | 0.0078 | >>50 | 3.13 |
| Gem | 0.006 | 0.009 | 0.004 | 0.040 | 0.0014 | 0.069 | 0.021 | 0.015 | 0.003 | >50 | >50 |

The concentration unit is in μM

UA62784 selectivity against DPC4 deficiency: 3.4

Cell Cycle Arrest

This result indicates that UA62784 induces G2/M cell cycle arrest and cell death in BxPC-3 cells Reagents: a) NaN₃, MeOH, HOAC; b) Ph₃P; THF/H₂O; c) 9-oxo-9H-fluorene-4-carbonyl chloride, NEt₃, DCM; d) POCl₃, DMF, 90°C; e) H₂, Pd/C, MeOH.

Reagents: a) H₂O₂, K₂CO₃, DMSO
b) NaN₃, EtOH
c) NH₂OH, EtOH; HCl
d) MeAlClNH₂; HCl. Tetrahedron Letters, 31(14), 1969-72; 1990

Priority Region-1 analogs for synthesis:

Priority Region-2 analogs for synthesis: Many aromatic acids are available:

Figure 23

Priority oxazole variants for synthesis:

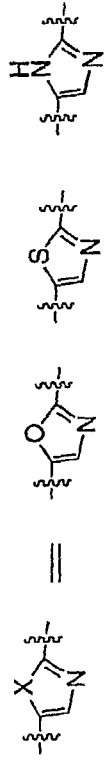

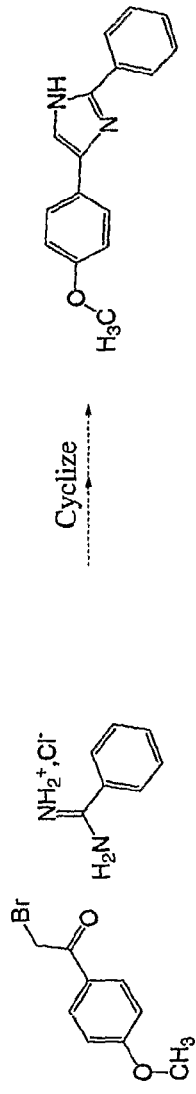

Reference:

Preparation of 2,4-disubstituted imidazoles: 4-(4-methoxyphenyl)-2-phenyl-1h-imidazole. Li, Bryan; Chiu, Charles K.-F.; Hank, Richard F.; Murry, Jerry; Roth, Joshua; Tobiassen, Harry. Chem. Res. and Dev., Pfizer Global Res. and Dev., Groton Lab., Groton, CT, USA. Organic Syntheses (2005), 81 105-111. Publisher: John Wiley & Sons, Inc., CODEN: ORSYAT ISSN: 0078-6209. Journal written in English. CAN 142:261464 AN 2005:30409 CAPLUS

SEQUENCE LISTING

```
<160> NUMBER OF SEQ ID NOS: 13

<210> SEQ ID NO 1
<211> LENGTH: 19
<212> TYPE: DNA
<213> ORGANISM: Homo sapiens

<400> SEQUENCE: 1
atgtctatta cgaatacac                                                   19

<210> SEQ ID NO 2
<211> LENGTH: 19
<212> TYPE: DNA
<213> ORGANISM: Homo sapiens

<400> SEQUENCE: 2
tgcccgtctc tggaggtgg                                                   19

<210> SEQ ID NO 3
<211> LENGTH: 19
<212> TYPE: DNA
<213> ORGANISM: Homo sapiens

<400> SEQUENCE: 3
atcgtgcatc gacagagac                                                   19

<210> SEQ ID NO 4
<211> LENGTH: 19
<212> TYPE: DNA
<213> ORGANISM: Homo sapiens

<400> SEQUENCE: 4
gtaggactgc accatacac                                                   19

<210> SEQ ID NO 5
<211> LENGTH: 19
<212> TYPE: DNA
<213> ORGANISM: Homo sapiens

<400> SEQUENCE: 5
ggtcaactct ccaatgtcc                                                   19

<210> SEQ ID NO 6
<211> LENGTH: 19
<212> TYPE: DNA
<213> ORGANISM: Homo sapiens

<400> SEQUENCE: 6
```
agcaaggttg cacataggc                                            19

<210> SEQ ID NO 7
<211> LENGTH: 27
<212> TYPE: DNA
<213> ORGANISM: Homo sapiens

<400> SEQUENCE: 7
cacgaattca tggacaatat gtctatt                                   27

<210> SEQ ID NO 8
<211> LENGTH: 27
<212> TYPE: DNA
<213> ORGANISM: Homo sapiens

<400> SEQUENCE: 8
attctcgagt cagtctaaag gttgtgg                                   27

<210> SEQ ID NO 9
<211> LENGTH: 21
<212> TYPE: DNA
<213> ORGANISM: Artificial sequence
<220> FEATURE:
<223> OTHER INFORMATION: Retrovirus vector

<400> SEQUENCE: 9
gttaacatcc tcgagagatc t                                         21

<210> SEQ ID NO 10
<211> LENGTH: 63
<212> TYPE: DNA
<213> ORGANISM: Artificial sequence
<220> FEATURE:
<223> OTHER INFORMATION: Retrovirus vector
<220> FEATURE:
<221> NAME/KEY: misc_feature
<222> LOCATION: (6)..(24)
<223> OTHER INFORMATION: n is a, c, g, or t
<220> FEATURE:
<221> NAME/KEY: misc_feature
<222> LOCATION: (35)..(53)
<223> OTHER INFORMATION: n is a, c, g, or t

<400> SEQUENCE: 10
aacccnnnnn nnnnnnnnnn nnnncttcct gtcannnnnn nnnnnnnnnn nnnttttgg  60 aaa                                                              63

<210> SEQ ID NO 11
<211> LENGTH: 67
<212> TYPE: DNA
<213> ORGANISM: Artificial sequence
<220> FEATURE:
<223> OTHER INFORMATION: Retrovirus vector
<220> FEATURE:
<221> NAME/KEY: misc_feature
<222> LOCATION: (15)..(33)
<223> OTHER INFORMATION: n is a, c, g, or t
<220> FEATURE:
<221> NAME/KEY: misc_feature
<222> LOCATION: (44)..(62)
<223> OTHER INFORMATION: n is a, c, g, or t

<400> SEQUENCE: 11
tcgatttcca aaaannnnnn nnnnnnnnnn nnntgacagg aagnnnnnnn nnnnnnnnnn  60 nngggtt                                                          67

<210> SEQ ID NO 12

```
<211> LENGTH: 50
<212> TYPE: DNA
<213> ORGANISM: Artificial sequence
<220> FEATURE:
<223> OTHER INFORMATION: Predicted short hairpin structure

<400> SEQUENCE: 12 cauccgacg ugguaugugg uuggucugtc acauaccacg ucaggauguu              50

<210> SEQ ID NO 13
<211> LENGTH: 50
<212> TYPE: DNA
<213> ORGANISM: Artificial sequence
<220> FEATURE:
<223> OTHER INFORMATION: Predicted short hairpin structure

<400> SEQUENCE: 13
cauccugacu ugguaugugg uuggucugtc acauaccaag ucaggauguu             50
```

METHODS, COMPOUNDS AND COMPOSITIONS WITH GENOTYPE SELECTIVE ANTICANCER ACTIVITY

RELATED APPLICATIONS

The present application claims the benefit of priority under 35 U.S.C. 119(e) to U.S. provisional application Ser. No. 60/671,758, filed Apr. 15, 2005, the contents of which are hereby fully incorporated by reference.

FIELD OF THE INVENTION

This invention relates to novel compounds that are able to selectively eliminate cancer cells with specific patterns of loss-of-function alterations, including but not limited to mutations, deletions, hypermethylations and other types of gene silencing. The present invention further relates to methods for the production and therapeutic use of such compounds. The present invention also relates to methods for screening and identification of compounds that are able to selectively eliminate cancer cells with specific patterns of loss-of-function alterations, including but not limited to mutations, deletions, hypermethylations, and other types of gene silencing.

BACKGROUND OF THE INVENTION

Pancreatic cancer is the fourth leading cause of cancer death among adults in the United States (1, 2). In the year 2005 alone, an estimated 32,180 new cases of pancreas cancer were predicted in the United States and 31,800 patients with pancreas cancer were expected to die (2). The five-year survival rate is about 4% (1, 2). This is largely due to the lack of symptoms and diagnostic tools for the detection of this disease at early stages as well as a deficiency of effective therapeutics for later stage disease.

In addition, pancreatic cancer is a highly chemoresistant malignancy. The most effective first-line drug for patients with advanced pancreatic cancer is gemcitabine, which provides only a very moderate improvement in survival (3). Thus, the discovery of new treatment for patients with pancreatic cancer is critically important.

One of the main genetic alterations in pancreatic cancer is the loss-of-function mutation of the DPC4 (Deleted in Pancreatic Cancer locus 4) tumor suppressor gene. The DPC4 gene is located on chromosome 18q21, a region that is homozygously deleted in 30–37% of pancreas ductal adenocarcinomas (4, 5). Intragenic inactivating mutations such as nonsense, misssense, and frameshift also occur commonly in the DPC4 gene, accompanied by a loss of the other allele, resulting in the loss of heterozygosity (5, 6). In total (both homozygous deletion and loss of heterozygosity), the DPC4 gene is inactivated in approximately 55% of patients' tumors (1, 7).

The loss of DPC4 gene is thought to be associated with the progression and malignancy of pancreatic cancer, as it occurs only in PanIN3 and pancreas adenocarcinomas (8, 9). DPC4 deficiency is also associated with poor survival of patients with pancreatic cancer. Patients with pancreatic cancer with normal DPC4 expression have significantly longer survival times. The unadjusted median survival was 19.2 months in patients with pancreatic cancers with DPC4 protein expression compared with 14.7 months in patients with pancreatic cancers lacking DPC4 protein (10).

In summary, loss of DPC4 has been considered as a predictor of decreased survival in pancreatic cancer (10, 11). Of additional interest is that loss of DPC4 is associated with progression and malignancy in other types of tumors as well. For example, Kuroki et al. reported that among 176 colorectal tumors at varying stages, DPC4 is lost in 0% (0/40) of adenomas, in 10% (4/39) of intramucosal carcinomas, in 7% (3/144) of invasive carcinomas without distant metastasis, in 35% (6/17) of primary invasive carcinomas with distant metastases, and in 31% (11/36) of carcinomas metastasized to the liver or distant lymph nodes (12), which is further supported by Lindberg et al. (13).

With its high frequency in pancreatic cancer, DPC4 deficiency presents a target for therapeutic intervention. The underlying promise of targeting DPC4 deficiency in pancreatic cancer is the hypothesis that molecular targets that are critical to the viability of cancer cells, in combination with DPC4 deficiency, exist in the genome of cancer cells and can be explored using small molecular weight compounds. It has been previously reported that some cancer cells with a specific loss-of-function mutation in tumor suppressor genes can be selectively killed by certain antitumor agents. For example, some myeloma cells with PTEN mutations are remarkably sensitive to CCI-779, a rapamycin analog than those with wild type PTEN (14). Erastin, a quinazoline analog, has been shown to specifically kill transformed tumorigenic human foreskin fibroblast cells expressing SV40 small T antigen and the RAS.sup.v12 oncoprotein (15). Similarly, DNA cross-linking agents such as mitomycin C and cisplatin have higher activity in pancreatic cancer cells with BRCA2 deficiency (16). However, none of the references discussed above mentioned any compounds capable of selectively targeting cancer cells deficient in DPC4 gene.

The present invention describes novel antitumor agents with genotype selectivity against cancer cells exhibiting DPC4 deficiency, methods for screening and identification of antitumor agents that selectively eliminate cancer cells with specific patterns of loss-of-function alterations, and methods for preparation and therapeutic use of such antitumor agents.

SUMMARY OF THE INVENTION

The present invention generally describes novel compounds that selectively eliminate cancer cells with specific patterns of loss-of-function alterations, including but not limited to mutations, deletions, hypermethylations and other types of gene silencing.

In one embodiment, the present invention describes small molecules that selectively kill pancreatic cancer cells with loss-of-function alterations, wherein such loss-of-function alterations include but are not limited to DPC4 gene deficiency.

In another embodiment, the present invention describes methods for screening and identification of compounds able to selectively target and eliminate cancer cells exhibiting specific patterns of loss-of-function alterations, including but not limited to mutations, deletions, hypermethylations, and other types of gene silencing.

In another embodiment, the present invention describes methods for production of compounds that selectively eliminate pancreatic cancer cells with DPC4 gene deficiency.

In yet another embodiment, the present invention describes methods for therapeutic use of compounds that selectively eliminate cancer cells with specific patterns of loss-of-function alterations, wherein such loss-of-function alterations include but are not limited to DPC4 gene deficiency.

These and various other advantages and novel features characterizing the present invention are also particularly pointed out in the claims attached to and forming a part of the present application. However, for a better understanding of the invention, its advantages, and objects obtained by its use, reference should also be made to the accompanying descriptive disclosure, in which the preferred embodiments and methods of practicing the present invention are described in requisite detail.

BRIEF DESCRIPTION OF THE DRAWINGS

The resent invention will become better understood with reference to the specification, appended claims, and accompanying drawings, where:

FIG. 1A demonstrates ectopic expression of DPC4 in BxPC-3 cells detected by Western blot. Whole cell extracts were prepared from HPDE6 and BxPC-3 cells infected by retrovirus containing the empty vector (BxPC-3 vector) and an individual clone of BxPC-3 infected by retrovirus containing pMSCVneoDPC4 (BxPC-3-DPC4). Each lane was loaded with 20 µg of total protein.

FIG. 1B demonstrates DPC4 nuclear localization upon the activation of TGF-β signaling pathway. The nucleic and cytoplasmic fractions of cell extracts were prepared from PANC-1, BxPC-3-vector and BxPC-3-DPC4 cells. 20 µg protein was loaded per lane. BxPC-3-vector-C: cytoplasmic fraction of BxPC-3-vector cell extracts; BxPC-3-vector-N: nucleic fraction of BxPC-3-vector cell extracts; PANC-1-C: cytoplasmic fraction of PANC-1 cell extracts; PANC-1-N: nucleic fraction of PANC-1 cell extracts; BxPC-3-DPC4-C: cytoplasmic fraction of BxPC-3-DPC4 cell extracts; BxPC-3-DPC4-C: nucleic fraction of BxPC-3-DPC4 cell extracts. Extracts from PANC-1 cells were included to serve as positive controls.

FIG. 1C demonstrates upregulation of p21 protein in BxPC-3-DPC4 cells. BxPC-3-vector, BxPC-3-DPC4 and HPDE6 cells were treated with 10 ng/ml of TGF-β. Whole cell extracts were prepared from treated cells and p21 protein was detected using Western blotting.

FIG. 1D demonstrates growth curves of BxPC-3-vector and BxPC-3-DPC4. Cells were seeded in six-well plates and allowed to grow under normal conditions. Two wells of cells for each cell line were harvested daily for 6 consecutive days and counted with a hemocytometer.

FIG. 1E demonstrates anchorage-independent growth of BxPC-3-DPC4 cells. 3,000 cells, mixed with 0.26% Difco agar and RPMI, were seeded onto an under-layer of 0.45% Difco agar containing RPMI in a 35-mm grid Petri dish, and allowed to grow for 19 days. Cell colonies (≧8 cells) were then counted. Each cell line was repeated in triplicates.

FIG. 3A provides structural formula of compound UA62001, 2-phenyl-1H-Naphth [2,3-g]indazole-3,6,11 (2H)-trione, one of the selective antitumor compounds of the present invention. FIG. 3B demonstrates the activity profile of UA62001 in the DPC4 isogenic cell lines (Estimated $IC_{50}$ 3.2±0.45 µM for BxPC-3-vector and 14.7±4.3 µM for BxPC-3-DPC4).

FIG. 4A demonstrates the cell cycle distribution of the untreated control samples harvested at 24, 48 and 72 hours. FIG. 4B demonstrates the cell cycle distribution of BxPC-3 cells treated with 25 µM UA62001 for 24, 48 and 72 hours.

FIG. 5A provides a graphic depiction of the Annexin V staining. The percentage of cells in the indicated M1 region was 4.6% in the untreated control and 8.2%, in the UA62001-treated (25 µM, 24 hours) BxPC-3 cells. FIG. 5B provides an image of the activation of pro-caspase-3 in BxPC-3 cells after UA62001 treatment. Whole cell extracts were prepared from BxPC-3-vector and BxPC-3-DPC4 cells after UA62001 (25 µM, 24 hours) treatment. Each lane was loaded with 20 µg of total protein. Camptothecin treated Jurkat cell lysate (20 µg) was loaded as the positive control. Lane 1, BxPC-3-DPC4; lane 2, BxPC-3-DPC4-UA62001; lane 3, BxPC-3-vector; lane 4, BxPC-3-vector-UA62001; lane 5, Jurkat-camptothecin.

FIG. 6 is a table demonstrating $IC_{50}$ values of UA62001 in pancreatic cancer cell lines and primary cells. The table lists the average µM concentration required to achieve 50% inhibition in MTS assay in each cell line ($IC_{50}$s were calculated by GraphPad Prism 4, GraphPad Software Inc) from three different cytotoxicity tests. HD, homozygous deletion; W', absence of the genetic alteration; Mut, Mutations (amino acids involved were indicated in the parenthesis).

FIG. 7 is a table comparing the Agilent microarray data and real-time quantitative RT-PCR data. Real-time quantitative RT-PCR was performed to validate the transcript changes of the genes of cyclin B/CDC2 and MCM complexes, measured by Agilent microarray analysis, in DPC4 isogenic cell lines in response to UA62001 treatment. The percentage values in parentheses represent the ratio (treatment/control) difference of each gene involved in cyclin B/CDC2 or MCM complex between the DPC4 isogenic cell lines.

FIG. 13A demonstrates the structural formula and activity profile of compound UA58978, one of the selective antitumor compounds of present invention.

FIG. 13B demonstrates the structural formula and activity profile of compound UA62784, one of the selective antitumor compounds of present invention.

FIG. 14 demonstrates the molecular properties of compound UA62784.

FIG. 15 is a table comparing the $IC_{50}$ values of compound UA62784 and gemcitabine.

FIG. 23 shows alternative five-membered heterocyclic groups that can be generated between the aromatic moiety of Region 1 and the aromatic acid of Region 2 to generate additional analogues of compound UA62874.

DETAILED DESCRIPTION OF THE INVENTION

Figure 1:
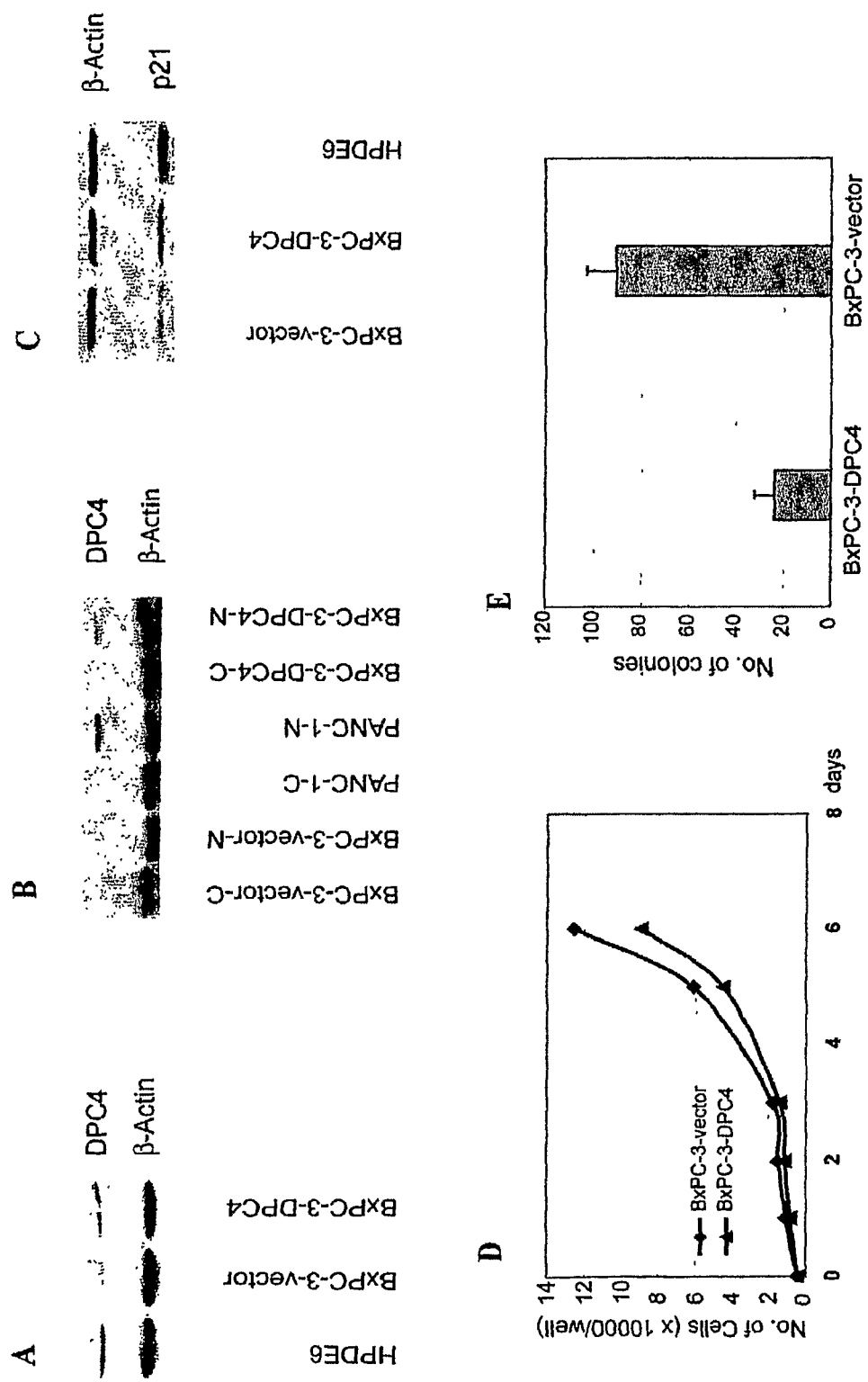
FIG. 1 is a series of images and graphs representing the ectopic expression of DPC4 in pancreatic cancer cell line BxPC-3.

The present invention is based upon the discovery of certain families of compounds that selectively kill pancreatic cancer cells with a DPC4 gene deficiency. These novel compounds selectively target cancer cells exhibiting a particular loss-of-function alteration, which represents a significant innovation from existing genetically selective antitumor agents which predominantly target cancer cells with gain-of-function alterations.

The present invention is also based upon the discovery of a novel method for screening and identification of compounds capable of selectively eliminating cancer cells with specific loss-of-function alterations, including but not limited to deletions, hypermethylations and other types of gene silencing.

The present invention is further based upon the discovery of novel methods for preparation and therapeutic use of compounds capable of selectively eliminating cancer cells with a loss-of-function alteration, wherein such loss-of-function alterations include but are not limited to a DPC4 gene deficiency.

Unless defined otherwise, all technical and scientific terms used herein have the same meaning as is commonly understood by one of skill in the art to which this invention belongs.

In accordance with the present invention and as used herein, the following terms are provided for nomenclature purposes. Furthermore, in an effort to maintain consistency in the naming of compounds of similar structures but differing substituents, the compounds described herein are named according to the following general guidelines.

The terms alkyl, alkenyl and alkynyl include straight-chain, branched-chain, saturated and/or unsaturated structures, and combinations thereof.

The terms heteroalkyl, heteroalkenyl and heteroalkynyl include optionally substituted $C_1$-$C_{10}$ alkyl, alkenyl and alkynyl structures, as described above, in which one or more skeletal atoms is oxygen, nitrogen, sulfur, or combinations thereof.

The terms haloalkyl, haloalkenyl and haloalkynyl include $C_1$-$C_{10}$ alkyl, alkenyl and alkynyl structures, as described above, that are substituted with one or more fluorines, chlorines, bromines or iodines, or with combinations thereof.

The terms cycloalkyl and cycloalkene include optionally substituted, saturated and/or unsaturated $C_3$-$C_7$ carbocyclic structures.

The term heterocycle includes optionally substituted, saturated and/or unsaturated, three- to seven-membered cyclic structures in which one or more skeletal atoms is oxygen, nitrogen, sulfur, or combinations thereof.

The term aryl refers to optionally substituted six-membered aromatic rings including optionally substituted polycyclic carbon ring systems of two to four, more preferably two to three, and most preferably two rings, including, without limitation, phenyl, biphenyl, naphthyl and anthryl ring systems.

The term heteroaryl refers to optionally substituted five- or six-membered heterocyclic aromatic rings containing one or more heteroatoms. The heterocyclic rings may contain one or more heteroatoms selected from the group consisting of oxygen, nitrogen and sulfur and six-membered heterocyclic rings may contain one or more nitrogens. Heterocyclic rings include polycyclic ring systems of from two to four, more preferably two to three, and most preferably two aromatic rings including, without limitation, furyl, pyrrolyl, pyrrolidinyl, thienyl, pyridyl, piperidyl, indolyl, quinolyl, thiazole, benzthiazole and triazole.

The term acyl includes alkyl, aryl, heteroaryl, arylalkyl or heteroarylalkyl substituents attached to a compound via a carbonyl functionality (e.g., —CO-alkyl, —CO-aryl, —CO-arylalkyl or heteroarylalkyl etc. . . . ).

The substituents of an "optionally substituted" structure may include, but are not limited to, one or more of the following preferred substituents: F, Cl, Br, I, CN, $NO_2$, $NH_2$, $NHCH_3$, $N(CH_3)_2$, SH, $SCH_3$, OH, $OCH_3$, $OCF_3$, $CH_3$, $CF_3$.

As used herein, the term "nucleic acid," "nucleic acid sequence," "polynucleotide," or similar terms, refers to a deoxyribonucleotide or ribonucleotide, oligonucleotide or polynucleotide, including single- or double-stranded forms, and coding or non-coding (e.g., "antisense") forms. The term encompasses nucleic acids containing known analogues of natural nucleotides. The term also encompasses nucleic acids including modified or substituted bases as long as the modified or substituted bases interfere neither with the Watson-Crick binding of complementary nucleotides or with the binding of the nucleotide sequence by proteins that bind specifically, such as zinc finger proteins. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones, such as N-(2-aminoethyl)glycine units. Phosphorothioate linkages are described, e.g., by U.S. Pat. Nos. 6,031,092; 6,001,982; 5,684,148; see also, WO 97/03211; WO 96/39154; Mata (1997) Toxicol. Appl. Pharmacol. 144:189-197. Other synthetic backbones encompassed by the term include methylphosphonate linkages or alternating methylphosphonate and phosphodiester linkages (see, e.g., U.S. Pat. No. 5,962,674; Strauss-Soukup (1997) Biochemistry 36:8692-8698), and benzylphosphonate linkages (see, e.g., U.S. Pat. No. 5,532,226; Samstag (1996) Antisense Nucleic Acid Drug Dev 6:153-156). Such analogues can be employed in the preparation and use of antisense nucleic acids as is well known in the art, such as for the purpose of inhibiting transcription. Additionally, the recitation of a nucleic acid sequence includes its complement unless the complement is specifically excluded or the context makes it clear that only one strand of the nucleic acid sequence is intended to be utilized. Additionally, the recitation of a nucleic acid sequence includes DNA, RNA, or DNA-RNA hybrids unless the context makes it clear that only one specific form of the nucleic acid sequence is intended to be utilized.

As used herein, the amino acids, which occur in the various amino acid sequences appearing herein, are identified according to their well-known, three-letter or one-letter abbreviations. The nucleotides, which occur in the various DNA fragments, are designated with the standard single-letter designations used routinely in the art.

In a peptide or protein, suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g. J. D. Watson et al., "Molecular Biology of the Gene" (4th Edition, 1987, Benjamin/Cummings, Palo Alto), p. 224). Specifically, in particular, the conservative amino acid substitutions can be any of the following: (1) any of isoleucine for leucine or valine, leucine for isoleucine, and valine for leucine or isoleucine; (2) aspartic acid for glutamic acid and glutamic acid for aspartic acid; (3) glutamine for asparagine and asparagine for glutamine; and (4) serine for threonine and threonine for serine. Other substitutions can also be considered conservative, depending upon the environment of the particular amino acid. For example, glycine (G) and alanine (A) can frequently be interchangeable, as can be alanine and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the different pK's of these two amino acid residues or their different sizes are not significant. Still other changes can be considered "conservative" in particular environments. For example, if an amino acid on the surface of a protein is not involved in a hydrogen bond or salt bridge interaction with another molecule, such as another protein subunit or a ligand bound by the protein, negatively charged amino acids such as glutamic acid and aspartic acid can be substituted for by positively charged amino acids such as lysine or arginine and vice versa. Histidine (H), which is more weakly basic than arginine or lysine, and is partially charged at neutral pH, can sometimes be substituted for these more basic amino acids. Additionally, the amides glutamine (Q) and asparagine (N) can sometimes be substituted for their carboxylic acid homologues, glutamic acid and aspartic acid.

As used herein, "expression vector" refers to a plasmid, virus or other vehicle known in the art that has been manipulated by insertion or incorporation of heterologous DNA, such as nucleic acid encoding the fusion proteins herein or expression cassettes provided herein. Such expression vectors contain a promoter sequence for efficient transcription of the inserted nucleic acid in a cell. The expression vector typically contains an origin of replication, and a promoter, as well as specific genes that permit phenotypic selection of transformed cells.

As used herein, "host cells" are cells in which a vector can be propagated and its DNA expressed. The term also includes any progeny of the subject host cell. It is understood that all progeny may not be identical to the parental cell since there may be mutations that occur during replication. Such progeny are included when the term "host cell" is used. Methods of stable transfer where the foreign DNA is continuously maintained in the host are known in the art.

As used herein, an expression or delivery vector refers to any plasmid or virus into which a foreign or heterologous DNA may be inserted for expression in a suitable host cell—i.e., the protein or polypeptide encoded by the DNA is synthesized in the host cell's system. Vectors capable of directing the expression of DNA segments (genes) encoding one or more proteins are referred to herein as "expression vectors". Also included are vectors that allow cloning of cDNA (complementary DNA) from mRNAs produced using reverse transcriptase. As used herein, a gene refers to a nucleic acid molecule whose nucleotide sequence encodes an RNA or polypeptide. A gene can be either RNA or DNA. Genes may include regions preceding and following the coding region (leader and trailer) as well as intervening sequences (introns) between individual coding segments (exons).

As used herein, "isolated," with reference to a nucleic acid molecule or polypeptide or other biomolecule means that the nucleic acid or polypeptide has separated from the genetic environment from which the polypeptide or nucleic acid were obtained. It may also mean altered from the natural state. For example, a polynucleotide or a polypeptide naturally present in a living animal is not "isolated", but the same polynucleotide or polypeptide separated from the coexisting materials of its natural state is "isolated", as the term is employed herein. Thus, a polypeptide or polynucleotide produced and/or contained within a recombinant host cell is considered isolated. Also intended as an "isolated polypeptide" or an "isolated polynucleotide" are polypeptides or polynucleotides that have been purified, partially or substantially, from a recombinant host cell or from a native source. For example, a recombinantly produced version of a compound can be substantially purified by the one-step method described in Smith et al. (1988) Gene 67:3140. The terms isolated and purified are sometimes used interchangeably.

Thus, by "isolated" the nucleic acid is free of the coding sequences of those genes that, in a naturally-occurring genome immediately flank the gene encoding the nucleic acid of interest. Isolated DNA may be single-stranded or double-stranded, and may be genomic DNA, cDNA, recombinant hybrid DNA, or synthetic DNA. It may be identical to a native DNA sequence, or may differ from such sequence by the deletion, addition, or substitution of one or more nucleotides.

Isolated or purified as it refers to preparations made from biological cells or hosts means any cell extract containing the indicated DNA or protein, including a crude extract of the DNA or protein of interest. For example, in the case of a protein, a purified preparation can be obtained following an individual technique or a series of preparative or biochemical techniques and the DNA or protein of interest can be present at various degrees of purity in these preparations. The procedures may include for example, but are not limited to, ammonium sulfate fractionation, gel filtration, ion exchange chromatography, affinity chromatography, density gradient centrifugation, electrophoresis, electrofocusing, chromatofocusing, or other protein purification techniques known in the art.

A preparation of DNA or protein that is "substantially pure" or "isolated" should be understood to mean a preparation free from naturally occurring materials with which such DNA or protein is normally associated in nature. "Essentially pure" should be understood to mean a "highly" purified preparation that contains at least 95% of the DNA or protein of interest.

As used herein, the term "vector" refers to a nucleic acid molecule capable of transporting between different genetic environments another nucleic acid to which it has been operatively linked. Preferred vectors are those capable of autonomous replication and expression of structural gene products present in the DNA segments to which they are operatively linked. Vectors, therefore, preferably contain the replicons and selectable markers described earlier.

All publications, including but not limited to patents and patent applications, cited in this specification are herein incorporated by reference as though fully set forth in the present application.

While the preferred embodiments of the present invention are illustrated below in numerical order, it is to be understood that the invention is not limited to the precise instructions and embodiments disclosed herein and that the right to all modifications coming within the scope of the following claims is reserved.

One embodiment of the present invention, referred to herein as embodiment 1, is a method for identifying molecules that eliminate cancer cells with a specific pattern of a loss-of-function genetic alteration comprising the steps of:

(a) creating a matched pair of isogenic cell lines that differ only by the presence or absence of expression of a single gene or a combination of several genes;

(b) screening a molecular library against the matched pair of isogenic cell lines to identify a molecule that exerts a differential effect on cell survival such that cell survival is diminished to a greater extent in the cell line that exhibits absence of expression of the single gene or the combination of several genes; and (c) confirming the differential effect in a tumor model selected from the group consisting of an in vivo tumor model and an in vitro tumor model to identify the molecules.

One embodiment of the present invention is the method of embodiment 1 wherein the presence or absence of expression is the presence or absence of expression of a single gene.

One embodiment of the present invention is the method of embodiment 1 wherein the presence or absence of expression is the presence or absence of expression of the combination of several genes; the several genes can be structurally related.

One embodiment of the present invention is the method of embodiment 1 wherein the absence of expression of the single gene or the combination of genes is achieved by RNA interference. The RNA interference can be performed by transient gene suppression using a synthetic RNA duplex, or, alternatively, by transcription of at least one short hairpin RNA by a RNA polymerase III promoter such that the short hairpin RNA is processed into siRNA.

One embodiment of the present invention is the method of embodiment 1 wherein the absence of expression of a single gene or the combination of genes is achieved by a homozygous deletion of the gene or the combination of genes in the pair of isogenic cell lines and wherein, in one of the pair of isogenic cell lines, expression of the single gene or the combination of genes is achieved by gene reexpression. The gene reexpression can be achieved by transfection or transformation of one of the pair of isogenic cell lines with an expression vector including therein the single gene or the combination of genes under control of a promoter in the expression vector. The promoter can be a retroviral promoter, such as the retrovirus y promoter.

The single gene can be a gene that affects the survival of a cancer cell selected from the group consisting of a pancreatic cancer cell and a colon cancer cell. The single gene can be selected from the group consisting of p15, p53, DPC4, BRAC2, APC-1, and E-cadherin. Particularly preferred single genes include, but are not limited to, p53 and DPC4.

The RNA interference can be carried out to block expression of a single gene, such as DPC4. When RNA interference is performed by transcription of a short hairpin RNA, the transcription of the short hairpin RNA is typically performed by transfection or transformation of the cell line with a vector including therein in sequence: (1) DNA encoding a sequence selected from the single gene whose expression is to be blocked; (2) DNA encoding a spacer sequence; and (3) DNA encoding the reverse complement of the selected sequence such that transcription of the vector results in formation of a short hairpin RNA. In one preferred alternative, when the gene is DPC4, the sequence selected from the DPC4 gene and the reverse complement of the sequence are both 19 nucleotides.

Preferred sequences include, but are not limited to:

```
5'- ATGTCTATTACGAATACAC-3';    (SEQ ID NO: 1)

5'-TGCCCGTCTCTGGAGGTGG-3';     (SEQ ID NO: 2)

5'-ATCGTGCATCGACAGAGAC-3';     (SEQ ID NO: 3)

5'-GTAGGACTGCACCATACAC-3';     (SEQ ID NO: 4)

5'-GGTCAACTCTCCAATGTCC-3';     (SEQ ID NO: 5)
and

5'-AGCAAGGTTGCACATAGGC-3'.     (SEQ ID NO: 6)
```

The use of 5'-GTAGGACTGCACCATACAC-3' (SEQ ID NO: 4) is particularly preferred. Accordingly, isolated purified oligonucleotides such as those of SEQ ID NO: 1 through SEQ ID NO: 6 are within the scope of the present invention. Additionally, vectors, including expression vectors, including therein SEQ ID NO: 1 through SEQ ID NO: 6 operably linked to at least one nucleotide sequence that affects, controls, or modulates the replication or transcription of the nucleotide sequence such as SEQ ID NO: 1 through SEQ ID NO: 6 are also within the scope of the present invention. Moreover, host cells transformed or transfected with isolated purified nucleotides according to the present invention or with vectors according to the present invention are also within the scope of the present invention. Additionally, isolated purified nucleotides differing in sequence from the sequences of SEQ ID NO: 1 through SEQ ID NO: 6 by no more than two nucleotides, using best matching according to the Needleman-Wunsch algorithm, are within the scope of the present invention provided that the nucleotides differing in sequence from the sequences of SEQ ID NO: 1 through SEQ ID NO: 6 can induce RNA interference. Preferably, the sequence differs by no more than one nucleotide, and the variant sequence can induce RNA interference. Vectors and host cells incorporating, transformed by, or transfected by these variant nucleic acid sequences are also within the scope of the present invention One embodiment of the present invention is the method of embodiment 1 wherein the molecular library is selected from the group consisting of a small molecule library, a library of siRNA molecules, a library of antisense RNA molecules, a library of protein molecules, and a library of peptide molecules.

When the molecular library is a small molecule library, the small molecular library can be selected from the group consisting of steroids, prostaglandins and analogues thereof, prostacyclins and analogues thereof, carbohydrates, receptor agonists, and receptor antagonists.

When the molecular library is a library of protein molecules, the library can be a library of antibody molecules or receptor molecules.

In one alternative, the molecules that are identified have therapeutic activity against pancreatic cancer. In another alternative, the molecules that are identified have therapeutic activity against colon cancer.

One embodiment of the present invention is a compound isolated by the method of embodiment 1 as described above. Such compounds and their analogues, derivatives, salts, and prodrugs are within the scope of the present invention.

In the case of salts, it is well known that organic compounds, including compounds having activities suitable for methods according to the present invention, have multiple groups that can accept or donate protons, depending upon the pH of the solution in which they are present. These groups include carboxyl groups, hydroxyl groups, amino groups, sulfonic acid groups, and other groups known to be involved in acid-base reactions. The recitation of a compound or analogue includes such salt forms as occur at physiological pH or at the pH of a pharmaceutical composition unless specifically excluded.

Similarly, prodrug esters can be formed by reaction of either a carboxyl or a hydroxyl group on compounds or analogues suitable for methods according to the present invention with either an acid or an alcohol to form an ester. Typically, the acid or alcohol includes a lower alkyl group such as methyl, ethyl, propyl, isopropyl, butyl, isobutyl, and tertiary butyl. These groups can be substituted with substituents such as hydroxy, or other substituents. Such prodrugs are well known in the art and need not be described further here. The prodrug is converted into the active compound by hydrolysis of the ester linkage, typically by intracellular enzymes. Other suitable groups that can be used to form prodrug esters are well known in the art. For example prodrugs can include amides prepared by reaction of the parent acid compound with a suitable amine. In some cases it is desirable to prepare double ester type prodrugs such as (acyloxy) alkyl esters or ((alkoxycarbonyl)oxy)alkyl esters. Suitable esters as prodrugs include, but are not necessarily limited to, methyl, ethyl, propyl, isopropyl, n-butyl, isobutyl, tert-butyl, morpholinoethyl, and N,N-diethylglycolamido. Methyl ester prodrugs may be prepared by reaction of the acid form of a compound having a suitable carboxylic acid group in a medium such as methanol with an acid or base esterification catalyst (e.g., NaOH, $H_2SO_4$). Ethyl ester prodrugs are prepared in similar fashion using ethanol in place of methanol. Morpholinylethyl ester prodrugs may be prepared by reaction of the sodium salt of a suitable compound (in a medium such as dimethylformamide) with 4-(2-chloroethyl)morphine hydrochloride (available from Aldrich Chemical Co., Milwaukee, Wis. USA.

Pharmaceutically acceptable salts include acid salts such as hydrochloride, hydrobromide, hydroiodide, sulfate, phosphate, fumarate, maleate, acetates, citrates, lactates, tartrates, sulfamates, malonate, succinate, tartrate, methanesulfonates, ethanesulfonates, benzenesulfonates, p-toluenesulfonates, cyclohexylsulfamates, quinates, formates, cinnamates, picrates, and other suitable salts. Such salts can be derived using acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid.

Pharmaceutically acceptable salts also include salts with bases such as alkali metal salts such as sodium or potassium, as well as pyridine salts, ammonium salts, piperazine salts, diethylamine salts, nicotinamide salts, calcium salts, magnesium salts, zinc salts, lithium salts, methylamino salts, triethylamino salts, dimethylamino salts, and tris(hydroxymethyl)aminomethane salts.

One embodiment of the present invention is a pharmaceutical composition comprising:

(1) a therapeutically effective quantity of a compound according to the present invention as described above; and (2) a pharmaceutically acceptable carrier.

As described below, pharmaceutical compositions can be prepared from specific compounds within the scope of the invention as described herein. The pharmaceutical composition can have therapeutic activity against pancreatic cancer or against colon cancer.

Pharmaceutical compositions according to the present invention can be formulated for oral administration or for parenteral administration. The route of administration depends on the chemical nature of the active species, the condition of the patient, and pharmacokinetic considerations such as liver or kidney function.

An additional aspect of the present invention is a method of treating a disease or condition treatable by inducing killing of a cancer cell with a specific pattern of a loss-of-function genetic alteration comprising administering a quantity of a compound as described above or subsequently, or of a pharmaceutical composition as described above or subsequently, sufficient to kill the cancer cell, thus treating the disease or condition. The disease or condition can be pancreatic cancer or colon cancer; however, the treatment of other forms of cancer is contemplated by the present invention.

Another embodiment of the present invention, described herein as embodiment 2, is a compound selected from the group consisting of:

(a) a compound of formula (I)

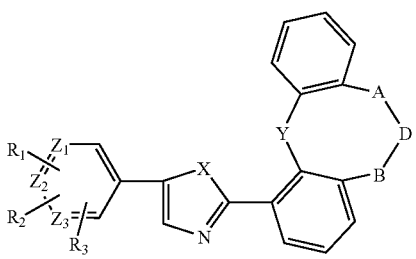

wherein:
(i) X is selected from the group consisting of O, NH, NR, and S, wherein R is $C_1$-$C_6$ lower alkyl;
(ii) Y is optionally present, and, if present, is selected from the group consisting of a valence bond, O, S, NH, NR, or $CH_2$, wherein R is $C_1$-$C_6$ lower alkyl;
(iii) $Z_1$ is selected from the group consisting of CH and N;
(iv) $Z_2$ is selected from the group consisting of CH and N;
(v) $Z_3$ is selected from the group consisting of CH and N;
(vi) A and B are optionally present, and, if present, are selected from the group consisting of a valence bond, O, $CH_2$, and NH, with the provisos that only one of A and B can be O and A or B can only be O when the other of A and B is a valence bond;
(vii) D is selected from the group consisting of CO, CS, C=N—$OCH_3$, and C=N—$NH_2$, with the provisos that where A and B are both not present, D is not present and where one of A and B is a valence bond and the other of A and B is O, D is not present; and
(viii) $R_1$, $R_2$, and $R_3$ are each independently selected from the group consisting of hydrogen, aryl, heteroaryl, halogen, trihalomethane, hydroxy, alkoxy, aryloxy, amino, N-alkylamino, N,N-dialkylamino, alkylcarbamoyl, arylcarbamoyl, aminocarbamoyl, N-alkyldiaminocarbamoyl, N,N-dialkylaminocarbamoyl, alkylsulfonylamino, arylsulfonylamino, carboxy, carboxyalkyl, N-alkylcarboxamido, N,N-dialkylcarboxamido, alkylthio, alkylsulfinyl, alkylsulfonyl, trifluoromethylsulfonylamino, arylthio, arylsulfinyl, arylsulfonyl, hydroxyalkyl, alkoxyalkyl, aryloxyalkyl, aminoalkyl, N-alkylaminoalkyl, N,N-dialkylaminoalkyl, alkylcarbamoylalkyl, arylcarbamoylalkyl, aminocarbamoylalkyl, N-alkylaminocarbamoylalkyl, N,N-dialkylaminocarbamoylalkyl, alkylsulfonylaminoalkyl, arylsulfonylaminoalkyl, alkylcarboxy, alkylcarboxyalkyl, N-alkylcarboxamidoalkyl, N,N-dialkylcarboxamidoalkyl, alkylthioalkyl, alkylsulfinylalkyl, alkylsulfonylalkyl, trifluoromethylsulfonylaminoalkyl, arylthioalkyl, arylsulfinylalkyl, and arylsulfonylalkyl, such that $R_2$ and $R_3$ can optionally form a five-membered or six-membered carbocyclic, heterocyclic, aryl, or heteroaryl ring system when taken together, and with the proviso that, where $Z_1$, $Z_2$, or $Z_3$ are nitrogen, the corresponding substituent $R_1$, $R_2$, or $R_3$ is absent;
(b) a prodrug of a compound of formula (I); and
(c) a salt of a compound of formula (I).

One embodiment of the present invention is the compound of embodiment 2 wherein the compound is a compound of formula (I).

In one alternative of embodiment 2, $Z_1$, $Z_2$, and $Z_3$ are CH. In this alternative, preferred compounds include compounds wherein $R_1$ is H, $R_3$ is H, and $R_2$ is selected from the group consisting of $CH_3S$, N=$CH_2$, $CH_3$—S(O)$_n$, wherein n is 1 or 2, N($CH_3$)$_2$—CO, $F_3C$, $NH_2$—$SO_2$, F, $NH_2$, Cl, $CH_3CONH$, $CH_3SO_2NH$, $H_3CO$, OH, and $F_3CO$.

In another alternative, $R_1$ is H, and $R_2$ and $R_3$ are selected from the group consisting of the following combinations: (1) $R_2$ is O, $R_3$ is O, and $R_2$ and $R_3$ are joined by a valence bond to form a five-membered ring; and (2) $R_2$ and $R_3$ are each $H_3CO$.

In still another alternative, $R_3$ is H, and $R_1$ and $R_2$ are selected from the group consisting of the following combinations: (1) $R_1$ is C=CH, $R_2$ is O, and $R_1$ and $R_2$ are joined by a valence bond to form a five-membered ring; (2) $R_1$ is C=N, $R_2$ is O, and $R_1$ and $R_2$ are joined by a valence bond to form a five-membered ring; (3) $R_1$ is C=CH, $R_2$ is S, and $R_1$ and $R_2$ are joined by a valence bond to form a five-membered ring; (4) $R_1$ is C=N, $R_2$ is S, and $R_1$ and $R_2$ are joined by a valence bond to form a five-membered ring; (5) $R_1$ is C=CH, $R_2$ is NH, and $R_1$ and $R_2$ are joined by a valence bond to form a five-membered ring; and (6) $R_1$ is C=N, $R_2$ is NH, and $R_1$ and $R_2$ are joined by a valence bond to form a five-membered ring.

In still another alternative, additional compounds are compounds of embodiment 2 as described above wherein Y, A, B, and D are selected from the group consisting of the following combinations: (1) Y is a valence bond, A is a valence bond, B is a valence bond, and D is CO; (2) Y is O, A is a valence bond, B is a valence bond, and D is CO; (3) Y is NH, A is a valence bond, B is a valence bond, and D is CO; (4) Y is a valence bond, A is NH, B is a valence bond, and D is O; (5) Y is a valence bond, A is a valence bond, B is NH, and D is CO; (6) Y is not present, A is a valence bond, B is a valence bond, and D is O; (7) Y is O, and A, B, and D are not present; (8) Y is not present, A is a valence bond, B is O, and D is not present; (9) Y is not present, A is a valence bond, B is a valence bond, and D is not present; and (10) Y is not present, A is not present, B is not present, and D is not present.

In still another alternative, additional compounds are compounds of embodiment 2 as described above wherein X is selected from the group consisting of O, S, and NH. In preferred alternatives, $R_2$ is $H_3CO$, Y is a valence bond, A is a valence bond, B is a valence bond, and D is CO, and X is O.

In additional alternatives of embodiment 2, $Z_1$ is CH, $Z_2$ is CH, $Z_3$ is CH, $R_1$ is H, $R_2$ is selected from the group consisting of $CH_2$=CH—$CH_2O$, ($CH_3$)2-$CH_2O$, 2-pyrimidinyl-O, 4-pyridyl-O, N=C—$CH_2O$, $H_2N$—$CH_2$—$CH_2O$, $H_2N$—(CO), ($H_2N$)(HON)C, ($H_2N$)(HN)C, amino, and tetrazolyl, $R_3$ is H, X is O, Y is a valence bond, A is a valence bond, B is a valence bond, and D is CO.

One particularly preferred embodiment is the compound of embodiment 2 wherein $Z_1$ is CH, $Z_2$ is CH, $Z_3$ is CH, $R_1$ is H, $R_2$ is $H_3CO$, $R_3$ is H, X is O, Y is a valence bond, A is a valence bond, B is a valence bond, and D is CO, and the compound has the structure of formula (II)

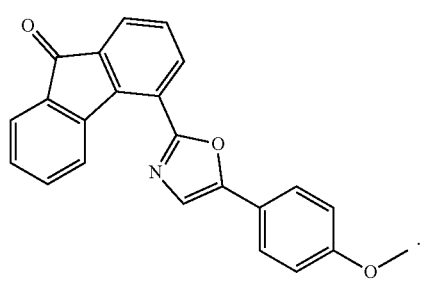

This compound is referred to herein as compound UA62784

Another alternative is a compound of embodiment 2 wherein $Z_1$ is CH, $Z_2$ is CH, $Z_3$ is CH, $R_1$ is H, $R_2$ is $H_3CO$, $R_3$ is H, X is O, Y is a valence bond, A is a valence bond, B is a valence bond, and D is selected from the group consisting of C=N—$NH_2$, C=N—O—$CH_3$, and C=N—OH. Still another alternative is a compound of formula (I) in which $Z_1$ is N, $Z_2$ is CH, and $Z_3$ is CH. A particularly preferred example of this alternative is a compound in which $R_1$ is absent, $R_2$ is $H_3CO$, and $R_3$ is H. Yet another alternative is a compound of formula (I) wherein $Z_1$ is CH, $Z_2$ is N, and $Z_3$ is CH. A particularly preferred example of this alternative is a compound of in which $R_1$ is H, $R_2$ is absent, and $R_3$ is H.

One embodiment of the present invention is embodiment 3, which is a compound selected from the group consisting of:
(a) a compound of formula (III)

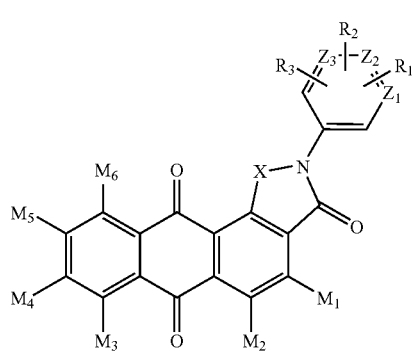

(III)

wherein:
(i) $Z_1$ is selected from the group consisting of CH and N;
(ii) $Z_2$ is selected from the group consisting of CH and N;
(iii) $Z_3$ is selected from the group consisting of CH and N;
(iv) $R_1$, $R_2$, and $R_3$ are each independently selected from the group consisting of hydrogen, aryl, heteroaryl, halogen, trihalomethane, hydroxy, alkoxy, aryloxy, amino, N-alkylamino, N,N-dialkylamino, alkylcarbamoyl, arylcarbamoyl, aminocarbamoyl, N-alkyldiaminocarbamoyl, N,N-dialkylaminocarbamoyl, alkylsulfonylamino, arylsulfonylamino, carboxy, carboxyalkyl, N-alkylcarboxamido, N,N-dialkylcarboxamido, alkylthio, alkylsulfinyl, alkylsulfonyl, trifluoromethylsulfonylamino, arylthio, arylsulfinyl, arylsulfonyl, hydroxyalkyl, alkoxyalkyl, aryloxalkyl, aminoalkyl, N-alkylaminoalkyl, N,N-dialkylaminoalkyl, alkylcarbamoylalkyl, arylcarbamoylalkyl, aminocarbamoylalkyl, N-alkylaminocarbamoylalkyl, N,N-dialkylaminocarbamoylalkyl, alkylsulfonylaminoalkyl, arylsulfonylaminoalkyl, alkylcarboxy, alkylcarboxyalkyl, N-alkylcarboxamidoalkyl, N,N-dialkylcarboxamidoalkyl, alkylthioalkyl, alkylsulfinylalkyl, alkylsulfonylalkyl, trifluoromethylsulfonylaminoalkyl, arylthioalkyl, arylsulfinylalkyl, and arylsulfonylalkyl, such that $R_2$ and $R_3$ can optionally form a five-membered ring when taken together, and with the proviso that, where $Z_1$, $Z_2$, or $Z_3$ are nitrogen, the corresponding substituent $R_1$, $R_2$, or $R_3$ is absent;
(v) X is selected from the group consisting of O, S, and NH; and
(vi) each of $M_1$, $M_2$, $M_3$, $M_4$, $M_5$, and $M_6$ is selected from the group consisting of hydrogen and $C_1$-$C_6$ lower alkyl;

(b) a prodrug of a compound of formula (III); and
(c) a salt of a compound of formula (III).

Typically, the compound is a compound of formula (III).

In one alternative of compounds of formula (III), $Z_1$, $Z_2$, and $Z_3$ are all CH and $R_1$, $R_2$, and $R_3$ are all H. In one preferred example of this alternative, X is NH.

One particularly preferred example of compounds of formula (III) is the compound of embodiment 77 wherein $Z_1$, $Z_2$, and $Z_3$ are all CH, $R_1$, $R_2$, and $R_3$ are all H, and X is NH, and wherein the compound has the structure of formula (IV)

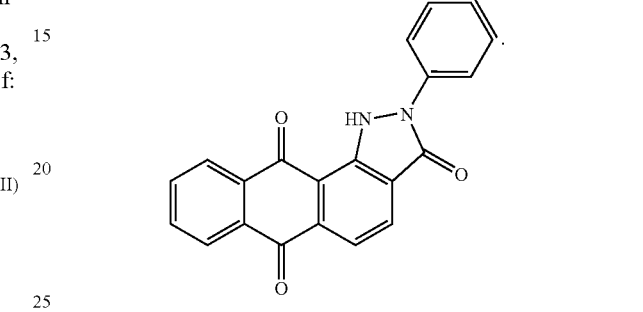

(IV)

This compound is referred to as compound UA62001.

One embodiment of the present invention, described herein generally as embodiment 4, is a compound selected from the group consisting of:
(a) a compound of formula (V)

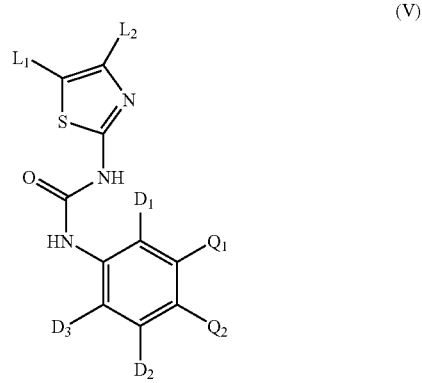

(V)

wherein:
(i) $L_1$ is selected from the group consisting of hydrogen and $C_1$-$C_6$ lower alkyl;
(ii) $L_2$ is selected from the group consisting of hydrogen and $C_1$-$C_6$ lower alkyl;
(iii) $D_1$ is selected from the group consisting of hydrogen and $C_1$-$C_6$ lower alkyl;
(iv) $D_2$ is selected from the group consisting of hydrogen and $C_1$-$C_6$ lower alkyl;
(v) $D_3$ is selected from the group consisting of hydrogen and $C_1$-$C_6$ lower alkyl;
(vi) $Q_1$ is selected from the group consisting of Cl, F, Br, and I; and
(vii) $Q_1$ is selected from the group consisting of Cl, F, Br, and I; and
(b) a prodrug of a compound of formula (V).

Typically, a compound of embodiment 4 is a compound of formula (V). In one preferred alternative, $L_1$ and $L_2$ are H. In another preferred alternative, $D_1$, $D_2$, and $D_3$ are H. In still another preferred alternative $Q_1$ and $Q_2$ are Cl.

A particularly preferred alternative is the compound of embodiment 4 or formula (IV) wherein $L_1$ and $L_2$ are H, wherein $D_1$, $D_2$, and $D_3$ are H, and wherein $Q_1$ and $Q_2$ are Cl, and wherein the compound has the structure of formula (VI)

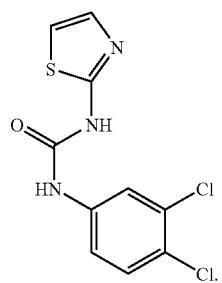

(VI)

This compound is described as compound UA58978.

Another embodiment of the present invention, embodiment 5, is a method of synthesizing a compound of formula (I), comprising the steps of:

(a) activating a carboxylic acid comprising the portion of the structure of formula (I) including therein the two benzene rings by reacting the carboxylic acid with thionyl chloride and dimethylformamide;

(b) reacting the activated carboxylic acid with an amine comprising the portion of the structure of formula (I) including therein the single aromatic ring in the presence of triethylamine to form an amide intermediate; and (c) reacting the amide intermediate with phosphorus oxychloride to form a five-membered heterocyclic ring including therein oxygen and nitrogen to generate the compound of formula (I). The method can further comprise a step of electrophilic aromatic substitution to substitute the moiety designated as $R_2$ with a substituent capable of being introduced by electrophilic aromatic substitution. The step of electrophilic aromatic substitution can replace Br as $R_2$ with $H_3CO$. The compound synthesized can be the compound of formula (II), or UA62784. The method can further comprise a step of purifying the compound by silica gel chromatography.

Another embodiment of the present invention, referred to herein as embodiment 6, is a method of synthesizing a substituted compound from a compound of formula (I) wherein $R_2$ is $H_3CO$ comprising the steps of:

(a) converting $R_2$ to OH by reaction with boron tribromide in a polar aprotic solvent; and (b) substituting $R_2$ by further reaction with a bromide or acyl chloride under basic conditions to generate the substituted compound. In one preferred alternative, $R_2$ of the substituted compound is selected from the group consisting of $CH_2=CH-CH_2O$, $(CH_3)2-CH_2O$, 2-pyrimidinyl-O, 4-pyridyl-O, and $N\equiv C-CH_2O$. Wherein $R_2$ of the substituted compound is $N\equiv C-CH_2O$, the method can further comprise a step of catalytic hydrogenation to convert the substituted compound to one in which $R_2$ is $H_2N-CH_2-CH_2O$.

One embodiment of the present invention, referred to herein as embodiment 7, is the method of synthesizing a compound of formula (I) in which $R_2$ is $H_2N$ comprising the steps of:

(a) reacting 2-bromo-4'-nitroacetophenone with sodium azide to generate 2-cyano-4'-nitroacetophenone;

(b) reducing the cyano group to yield 2-amino-4'-nitroacetophenone;

(c) reacting the 2-amino-4'-nitroacetophenone in the presence of triethylamine with an activated carboxylic acid comprising the portion of the structure of formula (I) including therein the two benzene rings to form an amide intermediate;

(d) reacting the amide intermediate with phosphorus oxychloride to form a five-membered heterocyclic ring intermediate including therein oxygen and nitrogen; and (e) reducing the nitro group by catalytic hydrogenation to synthesize the compound of formula (I) in which $R_2$ is $H_2N$.

Another embodiment of the present invention, referred to herein as embodiment 8, is a method for converting a compound of formula (I) in which $R_2$ is cyano to a compound in which $R_2$ is $H_2N-(CO)$ comprising the step of reacting the compound of formula (I) in which $R_2$ is cyano with hydrogen peroxide in the presence of a base to produce the compound in which $R_2$ is $H_2N-(CO)$.

Yet another embodiment of the present invention, referred to herein as embodiment 9, is a method for converting a compound of formula (I) in which $R_2$ is cyano to a compound in which $R_2$ is $(H_2N)(HON)C$ comprising the step of reacting the compound of formula (I) in which $R_2$ is cyano with azide in ethanol to produce the compound in which $R_2$ is $(H_2N)(HON)C$.

Still another embodiment of the present invention, referred to herein as embodiment 10, is a method for converting a compound of formula (I) in which $R_2$ is cyano to a compound in which $R_2$ is tetrazolyl comprising the step of reacting the compound of formula (I) in which $R_2$ is cyano with azide in ethanol to produce the compound in which $R_2$ is tetrazolyl Yet another embodiment of the present invention, referred to herein as embodiment 11, is a method for converting a compound of formula (I) in which $R_2$ is cyano to a compound in which $R_2$ is $(H_2N)(HON)C$ comprising the step of reacting the compound of formula (I) in which $R_2$ is cyano with hydroxylamine in the presence of acid to produce the compound in which $R_2$ is $(H_2N)(HON)C$.

Yet another embodiment of the present invention, referred to herein as embodiment 12, is a method for converting a compound of formula (I) in which $R_2$ is cyano to a compound in which $R_2$ is $(H_2N)(HN)C$ comprising the step of reacting the compound of formula (I) in which $R_2$ is cyano with MeAlClNH$_2$ in the presence of acid to produce the compound in which $R_2$ is $(H_2N)(HN)C$.

Still another synthetic embodiment of the present invention, referred to herein as embodiment 13, is a method for converting a compound of formula (I) in which D is CO to a compound in which D is $C=N-NH_2$ comprising the step of reacting the compound of formula (I) in which D is CO with hydrazine to produce the compound in which D is $C=N-NH_2$.

Still another synthetic embodiment of the present invention, referred to herein as embodiment 14, is a method for converting a compound of formula (I) in which D is CO to a compound in which D is C=NOH comprising the step of reacting the compound of formula (I) in which D is CO with hydroxylamine to produce the compound in which D is C=NOH.

Still another synthetic embodiment of the present invention, referred to herein as embodiment 15, is a method for converting a compound of formula (I) in which D is CO to a compound in which D is $C=N-O-CH_3$ comprising the step of reacting the compound of formula (I) in which D is CO with methylhydroxylamine to produce the compound in which D is $C=N-O-CH_3$.

Figure 17:
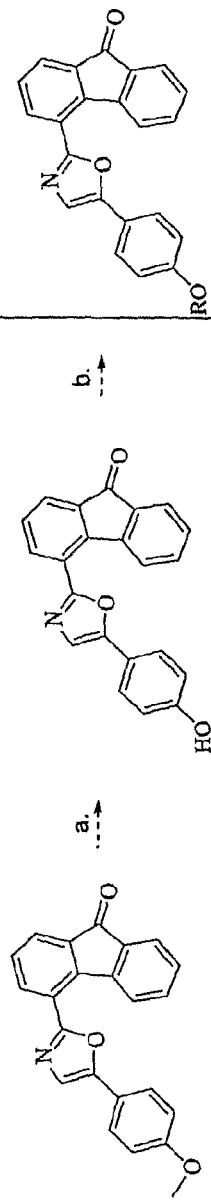
FIG. 17 is a schematic showing the preparation of derivatives of compound UA62784 by replacement of the methoxy substituent with a number of alternative substituents.
Figure 18:
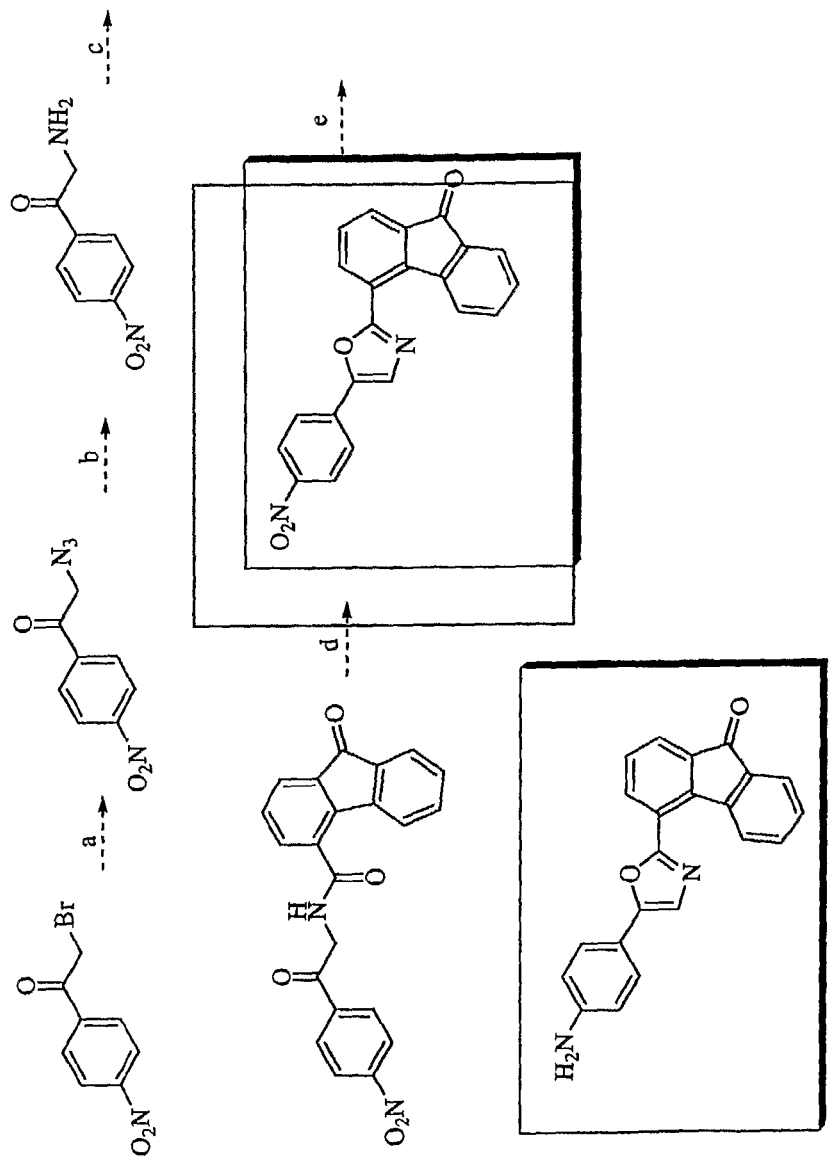
FIG. 18 is a schematic showing the preparation of an analogue of compound UA62874 by replacement of the methoxy substituent with an amine substituent.
Figure 19:
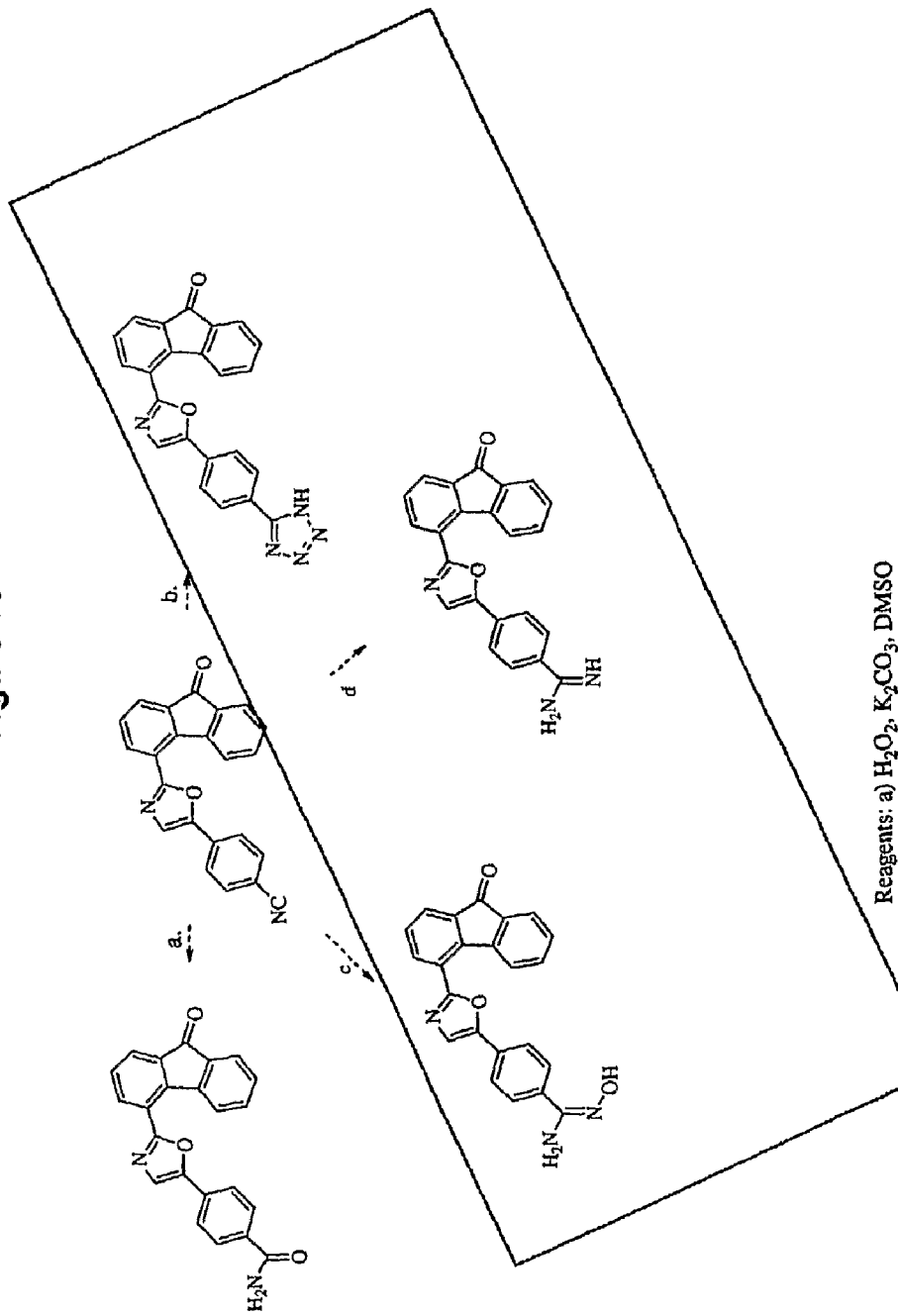
FIG. 19 is a schematic showing the preparation of additional analogues of compound UA62874 by replacement of the methoxy substituent with one of several nitrogen-containing substituents.
Figure 20:
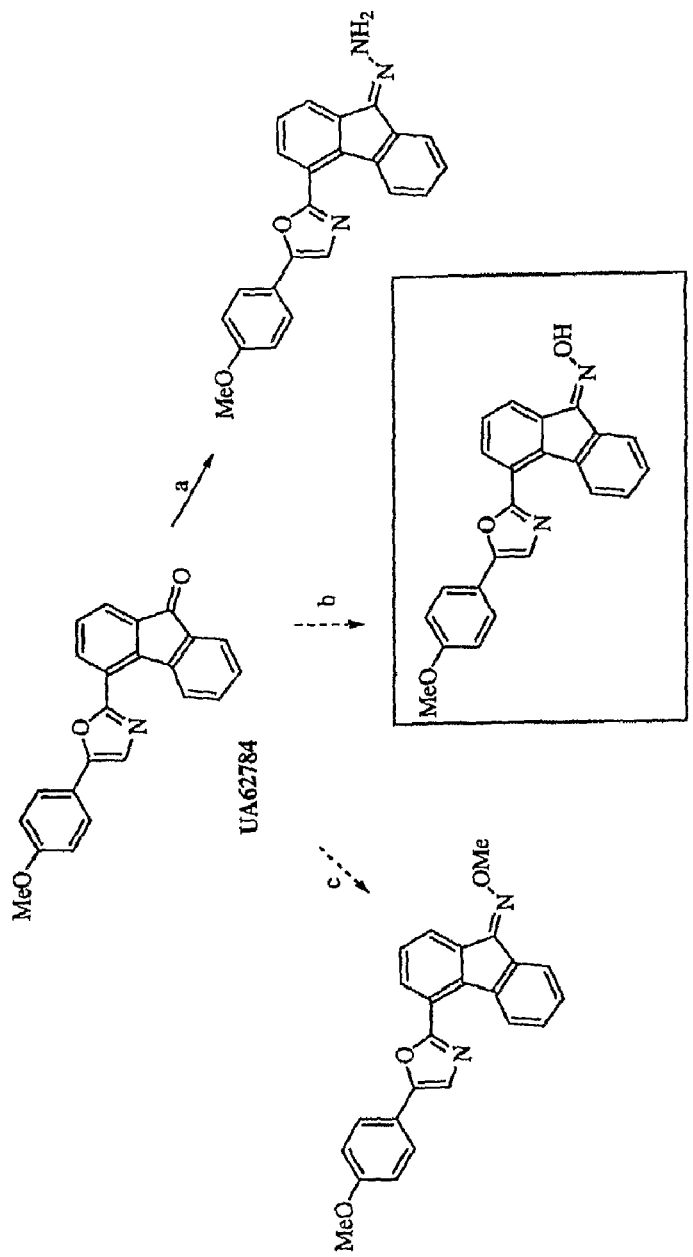
FIG. 20 is a schematic showing the preparation of additional analogues of compound UA62874 by replacement of the carbonyl moiety in the conjugated fluorene structure with one of several nitrogen-containing moieties.

As examples of synthetic methods, FIG. 17 is a schematic showing the preparation of derivatives of compound UA62784 by replacement of the methoxy substituent with a number of alternative substituents. This is performed by reaction with $BBr_3$ in DCM at −40° C. to room temperature, followed by reaction with RBr or RCOCl in DMF in the presence of the base potassium carbonate. Such alternatively substituted analogues are within the scope of the invention. Similarly, FIG. 18 is a schematic showing the preparation of an analogue of compound UA62874 by replacement of the methoxy substituent with an amine substituent. This is performed by reaction with sodium azide in methanol and acetic acid, followed by reaction with $Ph_3P$ in a THF/water solvent, followed by reaction of an appropriate carbonyl chloride, such as 9-oxo-9H-fluorene-4-carbonyl chloride in the presence of triethylamine in DCM, followed by reaction with $POCl_3$ in DMF at 90° C., followed by catalytic hydrogenation with molecular hydrogen using a Pd/C catalyst in MeOH. Again, such a substituted analogue is within the scope of the invention. Similarly, FIG. 19 is a schematic showing the preparation of additional analogues of compound UA62874 by replacement of the methoxy substituent with one of several nitrogen-containing substituents. In one alternative, reaction is performed with hydrogen peroxide in DMSO in the presence of sodium carbonate. In another alternative, reaction is performed with sodium azide in ethanol. In yet another alternative, reaction is performed with hydroxylamine in ethanol and HCl. In still another alternative, reaction is performed with $MeAlClNH_2$ in the presence of HCl (*Tetrahedron Lett.* 31: 1969-1972 (1990). Again, FIG. 20 is a schematic showing the preparation of additional analogues of compound UA62874 by replacement of the carbonyl moiety in the conjugated fluorene structure with one of several nitrogen-containing moieties. Reactions can occur with hydrazine in ethanol, with hydroxylamine in ethanol, or with methylhydroxylamine in ethanol. These analogues are within the scope of the invention.

Figure 21:
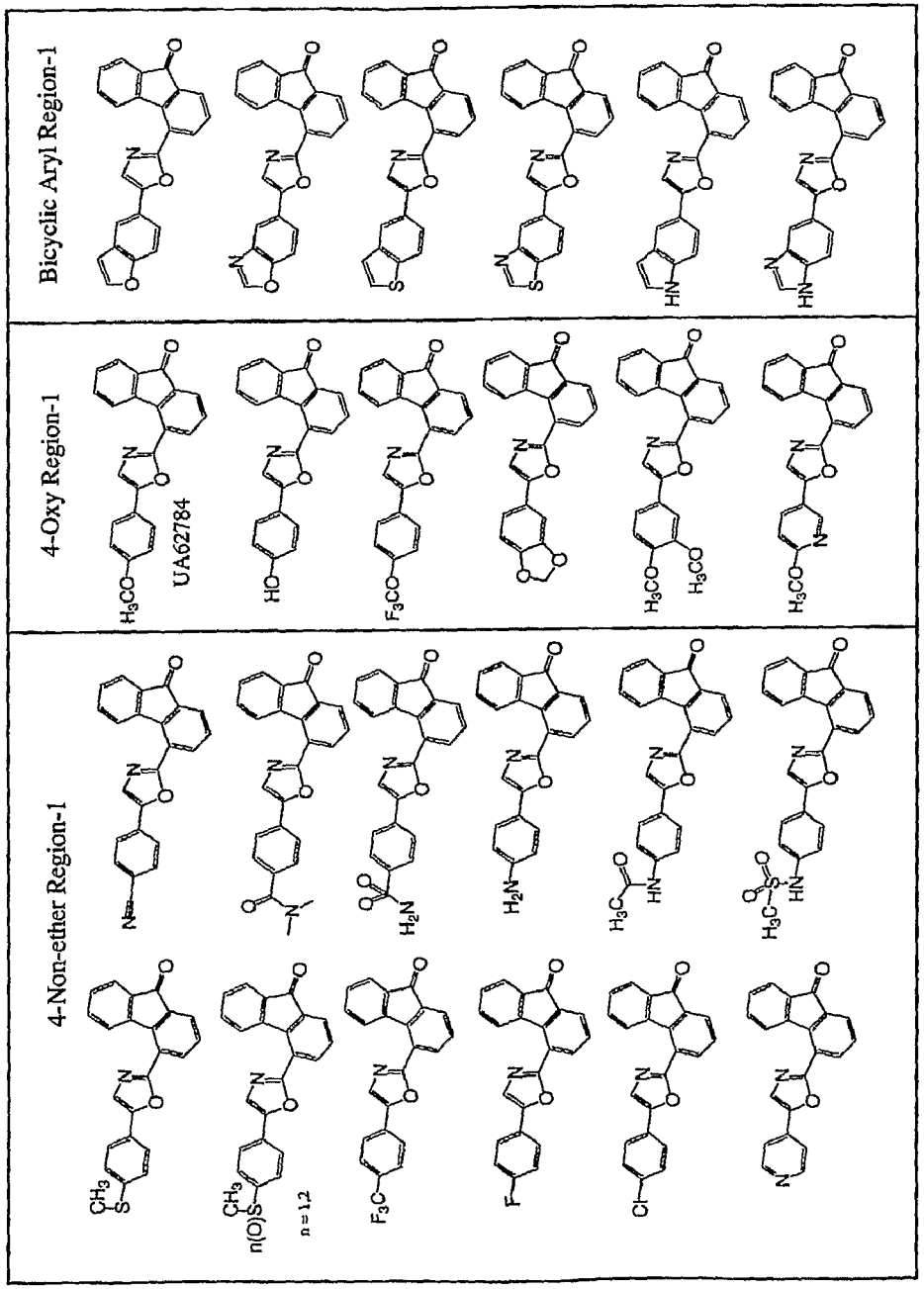
FIG. 21 shows the structures of analogues of compound UA62874 produced by varying the aromatic moiety introduced in Region 1 of the synthesis.
Figure 22:
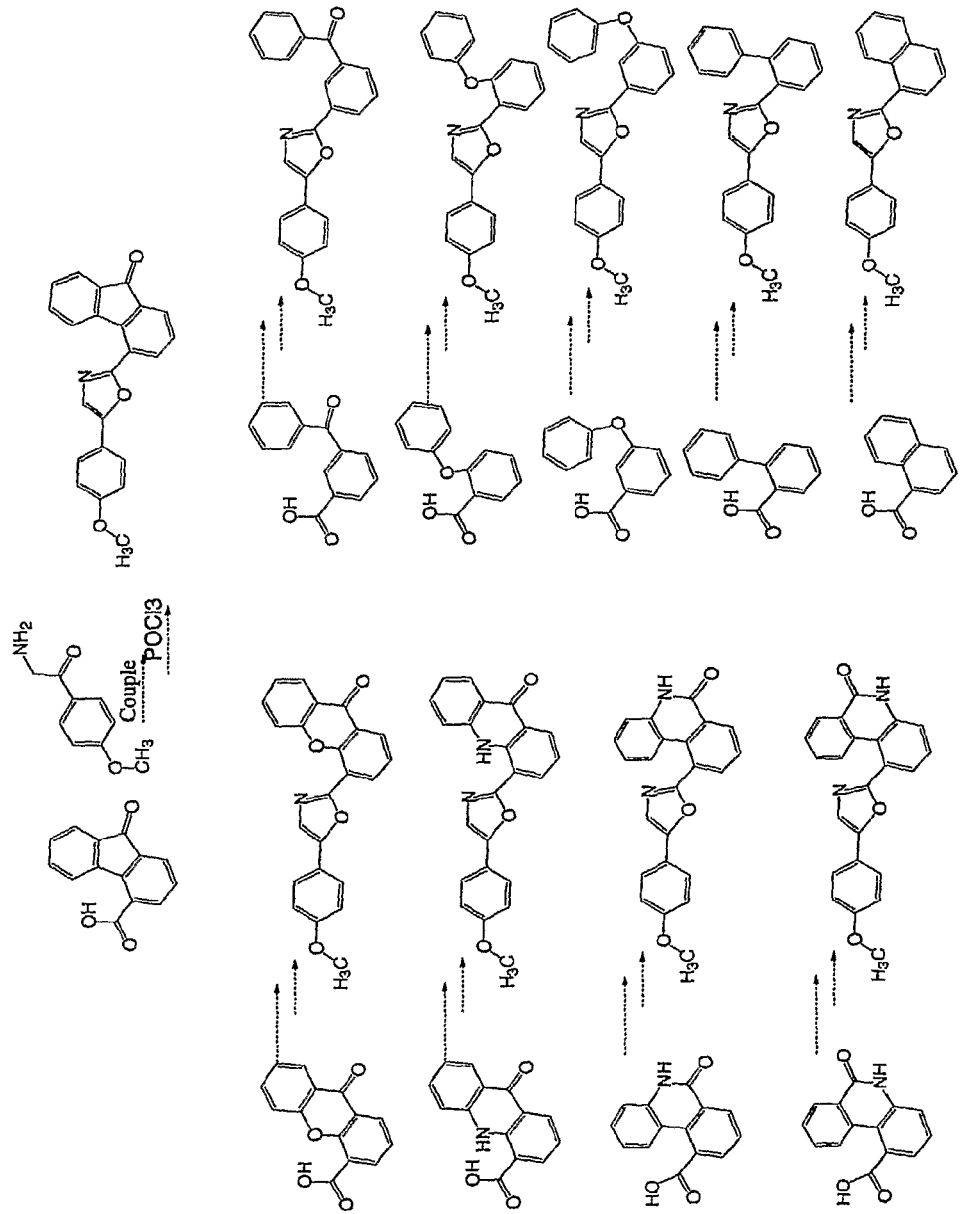
FIG. 22 similarly shows the structures of additional analogues of compound UA62874 produced by varying the aromatic acid introduced in Region 2 of the synthesis.

FIG. 21 shows the structures of analogues of compound UA62874 produced by varying the aromatic moiety introduced in Region 1 of the synthesis. The compounds of FIG. 21 are within the scope of the present invention. Similarly, FIG. 22 shows the structures of additional analogues of compound UA62874 produced by varying the aromatic acid introduced in Region 2 of the synthesis. The compounds of FIG. 22 are within the scope of the present invention. Again, FIG. 23 shows alternative five-membered heterocyclic groups that can be generated between the aromatic moiety of Region 1 and the aromatic acid of Region 2 to generate additional analogues of compound UA62874. These additional analogues of FIG. 23 are within the scope of the present invention.

The compounds of the present invention contain one or more chiral centers, and exist in different optically active forms. When compounds of the present invention contain one chiral center, the compounds exist in two enantiomeric forms and the present invention includes both enantiomers and mixtures of enantiomers, such as racemic mixtures.

The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent.

It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of the present invention has one or more chiral substituent it may exist in diastereoisomeric forms. The diastereoisomeric pairs may be separated by methods known to those skilled in the art, for example chromatography or crystallization and the individual enantiomers within each pair may be separated as described above. The present invention includes each diastereoisomer of compounds disclosed herein as well as any and all mixtures thereof.

Certain compounds of the present invention may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of the present invention and mixtures thereof.

Certain compounds of the present invention may exist in zwitterionic form and the present invention includes each such zwitterionic form and mixtures thereof.

Certain compounds of the present invention and their salts may exist in more than one crystal form. Polymorphs of compounds of the present invention form part of this invention and may be prepared by crystallization of a compound(s) of the present invention under different conditions.

For example, different conditions which may be potentially used to prepare polymorphs of compounds of the present invention include but are not limited to using different solvents or different solvent mixtures for recrystallization; crystallization at different temperatures; various modes of cooling, ranging from very fast to very slow cooling during crystallization.

Polymorphs may also be obtained by heating or melting a compound(s) of the present invention followed by gradual or fast cooling. The presence of polymorphs may be determined by solid probe NMR spectroscopy, IR spectroscopy, differential scanning calorimetry, powder X-ray diffraction or such other techniques.

The compounds disclosed in the present invention represent a novel group of small molecules that are able to target and kill pancreatic cancer cells in a genotype-selective manner, namely by targeting pancreatic cancer cells with DPC4 gene deficiency.

The particular conditions that can be treated with the compounds of the present invention include but are not limited to various types of colorectal tumors, such as pancreatic cancers, colon cancers, adenomas, intramucosal carcinomas, invasive carcinomas without distant metastasis, primary invasive carcinomas with distant metastases, and carcinomas metastasized to the liver or distant lymph nodes.

Furthermore, it is understood by those skilled in the art that the compounds of the present invention, including but not limited to pharmaceutical compositions and formulations containing these compounds can be used in a wide variety of combination therapies to treat the conditions and diseases described above. As described above, all compounds within the scope of the present invention can be used to formulate appropriate pharmaceutical compositions, and such pharmaceutical compositions can be used to treat the conditions described above, including, but not limited to, pancreatic cancer and colon cancer. The use of pharmaceutical compositions according to the present invention is further completed for the treatment of other conditions in which is necessary to control proliferation of cells that have undergone a loss-of-function mutation that has the effect of diminishing normal growth control in these cells.

Pharmaceutical Formulation and Administration:

Compound(s) of the present invention or derivative(s) and/or combination(s) thereof, as the active ingredient, can be put in pharmaceutically acceptable formulations, such as those described in Remington's Pharmaceutical Sciences, 18$^{th}$ ed., Mack Publishing Co., Easton, Pa. (1990), incorporated by reference herein, and used for specific treatment of diseases and pathological conditions with little or no effect on healthy tissues.

The preparation of a pharmacological composition comprising active ingredients dissolved or dispersed therein need not be limited based on formulation. Such compositions may be prepared as injectable liquid solutions or suspensions. However, solid forms suitable for dissolution, or resuspension, in liquid prior to use can also be prepared. The preparation can also be emulsified.

In a preferred embodiment, the composition is held within a container, which includes a label stating to the effect that the composition is approved by the FDA in the United States (or other equivalent labels in other countries) for treating a disease or condition described herein. Such a container will provide therapeutically effective amount of the active ingredient to be administered to a host.

The particular therapeutic agents that affect the conditions of interest can be administered to a mammal either alone or in pharmaceutical compositions where it is mixed with suitable carrier(s) or excipient(s). In treating a mammal exhibiting a condition of interest, a therapeutically effective amount of an agent or agents, such as one of the structures of the present invention (including, but not limited to compounds of Formula I and derivatives thereof), is administered. The active ingredient can be mixed with excipients that are pharmaceutically acceptable and compatible with said active ingredient and in amounts suitable for use in the therapeutic methods described herein.

Pharmaceutically acceptable salts can be prepared by standard techniques. For example, the free base form of the compound is first dissolved in a suitable solvent such as an aqueous or aqueous-alcohol solution, containing the appropriate acid. The salt is then isolated by evaporating the solution. In another example, the salt is prepared by reacting the free base and acid in an organic solvent.

Carriers or excipients can be used to facilitate administration of the compound, for example, to increase the solubility of the compound. Examples of carriers and excipients include calcium carbonate, calcium phosphate, various sugars or types of starch, cellulose derivatives, gelatin, vegetable oils, polyethylene glycols, water, saline, dextrose, glycerol, ethanol and physiologically compatible solvents.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred.

The data obtained from these cell culture assays and animal studies can be used in formulating a range of dosage for use in human. The dosage of such compounds lies preferably within a range of circulating concentrations that include the ED50 with little or no toxicity. The dosage may vary within this range depending upon the dosage form employed and the route of administration utilized.

For any genotype-selective anticancer compound used in the methods of the invention, the therapeutically effective dose can be estimated initially from cell culture assays. For example, a dose can be formulated in animal models to achieve a circulating plasma concentration range that includes the IC50 as determined in cell culture (i.e., the concentration of the test compound which achieves a half-maximal disruption of the protein complex, or a half-maximal inhibition of the cellular level and/or activity of a complex component). Such information can be used to more accurately determine useful doses in humans. Levels in plasma may be measured, for example, by HPLC.

The exact formulation, route of administration and dosage can be chosen by the individual physician in view of the mammal's condition. (See e.g. Fingl et al., in The Pharmacological Basis of Therapeutics, 1975, Ch. 1 p. 1). It should be noted that the attending physician would know how to and when to terminate, interrupt, or adjust administration due to toxicity, or to organ dysfunctions.

Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency will also vary according to the age, body weight, and response of the individual mammal.

Depending on the specific conditions being treated, such agents may be formulated and administered systemically or locally. Techniques for formulation and administration may be found in Remington's Pharmaceutical Sciences, 18th ed., Mack Publishing Co., Easton, Pa. (1990), which is incorporated herein by reference.

For injection, the agents of the invention may be formulated in aqueous solutions, preferably in physiologically compatible buffers such as Hanks's solution, Ringer's solution, or physiological saline buffer.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in watersoluble form. Additionally, suspensions of the active compounds may be prepared as appropriate oily injection suspensions.

Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Novel Screening Method:

One embodiment of the present invention is a method for screening and identification of compounds that selectively eliminate cancer cells with specific loss-of-function alterations, including but not limited to mutations, deletions, hypermethylations, and other types of gene silencing.

The Concept of Pharmacological Synthetic Lethal Screening (PSLS)

Synthetic lethal screening is a genetic technique that has been used for years in genetic model systems to identify mutations that are lethal in combination (53, 54). The discovery of synthetic lethal interactions between genes allows for genetic dissection of pathways and helps to identify the functions of gene products. The use of synthetic lethal screening as a tool for drug development is based on the premise that the accumulation of genetic alterations may not only provide cancer cells with selective growth advantages but may also predispose them to increased sensitivity to loss of other genes. For example, in *Saccharomyces cerevisiae* cells harboring genetic defects in the mismatch repair gene PMS1 are selectively killed by mutations in the genes for DNA polymerase $\delta$ and $\epsilon$ (55). Currently, every gene in the yeast genome is being systematically explored for synthetic lethal.

The systematic use of synthetic lethal screening in a yeast genome could produce novel targets for cancer drug development. Unfortunately, many of genetic defects in cancer do not have good structural or functional homologs of genes in the yeast genome. Even where homologs exist, it is likely that mammalian cells have different mechanisms to compensate for the loss of specific genes. Thus, the development of a mammalian system to identify synthetic lethal interactions with genetic defects in cancers is necessary. In the yeast model, the synthetic lethal interaction with a primary gene mutation is explored through the mutagenesis of yeast strain harboring a primary mutation to screen for the lethality of yeast cells. In mammalian cells, we use organic molecules (small molecular weight molecules, antisense oligonucleotides, siRNA oligonucleotides or proteins) as agonists or antagonists of proteins to mimic gene mutations. Treatment of cells with such molecules alone is not lethal but can potentially induce lethality in cancer cells harboring specific loss-of-function mutations such as p53 or DPC4. Hence, Applicants refer to this phenomenon as pharmacological synthetic lethality (PSLS). Agents that show such pharmacological synthetic lethality are therefore genotype selective.

Generation of Matched Pair (Isogenic) Cell Lines

The first step of the pharmacological synthetic lethal screening is to generate isogenic cell lines that only differ in one single gene or combination of several genes. Applicants have taken two approaches to create the isogenic cell lines.

One approach is to specifically "knock down" the expression of gene of interest in immortalized normal cells using RNA interference (RNAi). A potential problem with such approach is that the genetic background of engineered cell lines is normal cell based and is different from that of pancreatic cancer cells. Therefore, agents identified in the screening might not be as active in cancer cells.

The other approach is to reexpress the wild type gene of interest in a cell line with homozygous deletion of the gene. The potential problem with cell lines generated in this reexpression approach is that reexpression of tumor suppressor gene in its loss-of-function pancreatic cancer cells might cause cell cycle inhibition and therefore stop cell growth. To overcome these potential problems, Applicants generated isogenic cell lines using both approaches for each gene of interest.

In preliminary studies, Applicants used DPC4 (MADH4 or SMAD4), a tumor suppressor gene that has been shown to be mutated or homozygously deleted in approximately 50% of pancreas ductal adenocarcinomas (56. 57), as an example to generate matched-pair cell lines using both reexpression and RNAi app. As described below, Applicants successfully generated two sets of matched-pair cell lines for the DPC4 gene—one set for each approach.

Generation of Isogenic Cell Lines Using Gene Reexpression

One way to generate isogenic cell lines that only differ in genes of interest is to reexpress these genes in cells that do not express them. For instance, the DPC4 gene has been reported to be homozygously deleted in a number of pancreatic cancer cell lines including BxPc3, CFPAC-1, and HS766T. Therefore, Applicants used BxPc3 as the parental cell line to generate a matching cell line that expresses wild-type DPC4.

To do so, they first cloned the full length cDNA of the DPC4 gene to a retrovirus vector pMSCVneo (Clontech, Palo Alto, Calif.), which has a neomycin selection marker. In the new construct, pMSCVneoDPC4 (FIG. 8A), the DPC4 gene expression is under the control of retrovirus T promoter. Transient transfection of BxPc3 cells using pMSCV-neoDPC4 was performed to verify the DPC4 expression. To generate a cell line that constitutively expression DPC4, pMSCVneoDPC4 was introduced into BxPc3 cells using the retrovirus system.

As a negative control, retrovirus containing the pMSCV-neo empty vector was also produced. Individual clones were isolated using serial dilution of the transfected cells in 96-well plates. DPC4 expression in selected individual clones was detected by Western blot.

Figure 8:
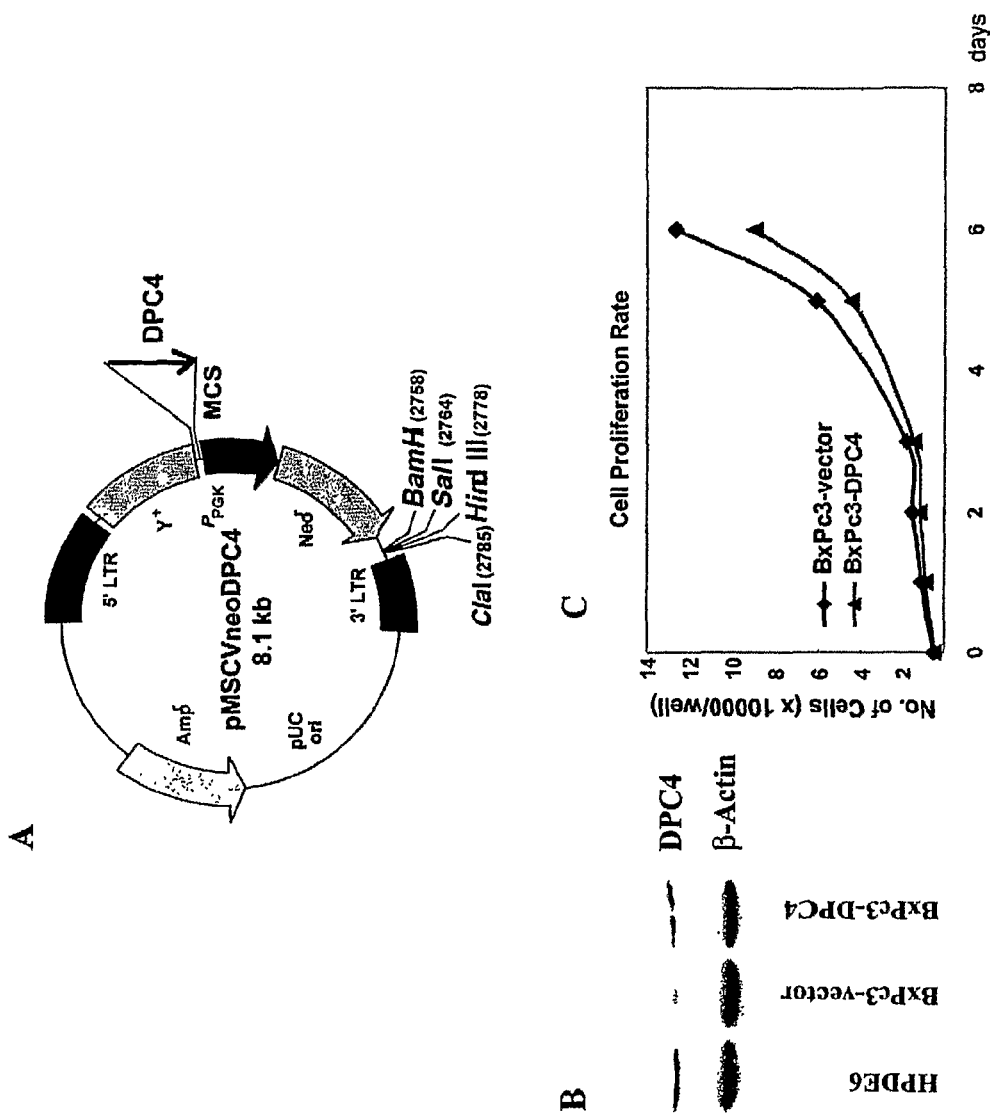
FIG. 8A is a schematic diagram of the retrovirus construct for the expression of DPC4 gene.
FIG. 8B demonstrates reexpression of DPC4 in BxPc3 cells detected by Western blot.
FIG. 8C is a graph demonstrating the growth curves of BxPc3 and BxPc3-DPC4. Cells were seeded to six-well plates at 50,000 cells/well. One well of cells for each cell line were harvested daily and counted with hemocytometer.

As shown in FIG. 8B, one clone, BxPc3-DPC4, has a DPC4 expression level that is comparable to that in the immortalized normal pancreatic ductal epithelial cell line HPDE6 (kindly provided by Dr. Ming-Song Chao at the University of Toronto, Canada). The proliferation rate of BxPc3-DPC4 was examined and compared with that of BxPc3 (FIG. 8C). As expected BxPc3-DPC4 expressing DPC4 had a slower growth rate than its parental cell line BxPc3.

Generation of Isogenic Cell Lines Using RNA Interference (RNAi)

Recently, the discovery of gene silencing through RNAi has opened up new possibilities for the "knock-down" of specific gene expression in mammalian cells. The gene silencing through the RNAi was first discovered in plants (58), then *C. elegans* and *Drosophila melanogaster* (59, 60, 61). Now it is found that RNAi is the common mechanism in higher organisms for viral defense and transposon silencing. The first use of RNAi gene silencing in mammalian cells is the transient gene suppression using 21-bp synthetic RNA duplex (62). The synthetic RNA duplex is very useful to study gene function through transient gene suppression but cannot be used for the long-term gene suppression (stable gene suppression) because the RNA duplex is degraded very quickly in mammalian cells. The study of small nucleic RNAs and their transcription leads to the discovery of the transcription of short hairpin RNA in vivo by RNA polymerase III promoters such as those of the H1 RNA, the RNA subunit of RNase P complex and U6 snRNA genes, which have well defined transcription initiation and termination signals. Short hairpin RNAs are processed into siRNAs and induce RNAi gene silencing (63, 64). The ability to quickly and easily create loss-of-function phenotypes through RNAi gene silencing in mammalian cells opens up new possibilities to perform cell-based screen to target loss-of-function mutations in pancreatic cancers.

Applicants developed a RNA interference (RNAi) based approach to generate isogenic cell lines.

First, three expression vectors were created by cloning the H1 RNA promoter into the pMSCV retrovirus system (Clontech), which contains three constructs. Retrovirus system was used to increase the DNA delivery efficiency in normal epithelial cells which are usually very difficult to transfect. These three expression vectors have identical elements except the antibiotic selection marker (puromycin, neomycin or hygromycin).

Figure 9:
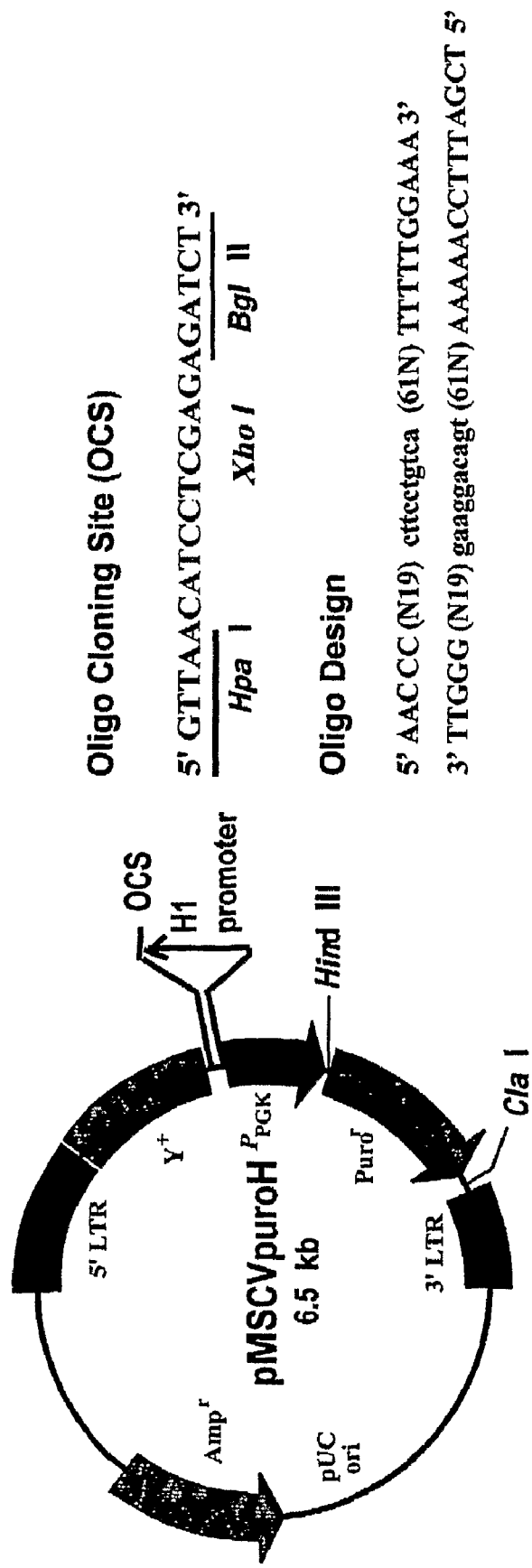
FIG. 9 is a schematic diagram of the pMSCVpuroH retrovirus vector for the in vivo expression of short hairpin RNA. Also shown are the Oligo Cloning Site (5'GTTAACATC-CTCGAGAGATCT 3') (SEQ ID NO: 9) and sequences used for oligo design (5'AACCC (N19) cttcctgtca (61N) TTTTTG-GAAA 3') (SEQ ID NO: 10) and (3' TTGGG (N19) gaagga-cagt (61N) AAAAACCTTTAGCT 5') (SEQ ID NO: 11).

Different selection markers can allow the practitioner to suppress more than one gene in immortalized normal cells. One of the retrovirus vectors constructed for siRNA expression, pMSCVpuroH, which has a puromycin selection marker, is shown in FIG. 9. It contains an oligo cloning site (OCS) immediate downstream of the H1 promoter. Gene specific oligos for siRNA expression can be designed based on the template sequences shown on the right panel of FIG. 9. The designed oligo consists of a 19-nt sequence selected from the target gene, separated by a short spacer (65) from the reverse complement of the same 19-nt sequence. Restriction sites HpaI and XhoI are attached to the 5' and 3' ends of DNA oligos, respectively, for unidirectional insertion into the oligo cloning site (OCS) immediately downstream of H1 promoter.

As an example, Applicants created a siRNA expression vector for the DPC4 gene and delivered it to HPDE6 cells to generate a cell line that has the DPC4 expression stably suppressed. The pMSCVproH vector was first used to create 6 DPC4 siRNA expression constructs, each of which targets a different region of the DPC4 transcript. Each of the oligonucleotide sequences was designed based on the criteria described by Tuschl and co-workers (65) and blasted against the GenBank database to confirm their specificity for DPC4.

Figure 10:
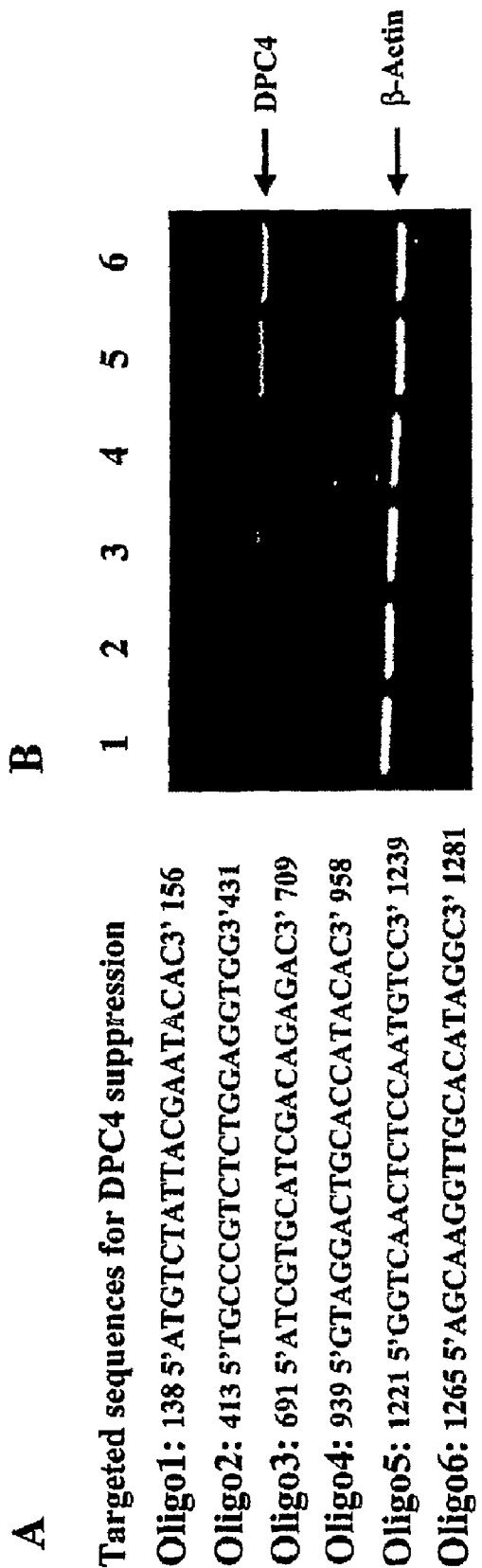
FIG. 10A lists sequences of the 6 oligonucleotides designed for the DPC4 siRNA expressing constructs. The 6 oligonucleotides are Oligo1: (138 5' ATGTCTATTAC-GAATACAC 3') (SEQ ID NO: 1); Oligo2: (413 5' TGC-CCGTCTCTGGAGGTGG 3') (SEQ ID NO: 2); Oligo3: (691 5' ATCGTGCATCGACAGAGAC 3') (SEQ ID NO: 3); Oligo4: (939 5'GTAGGACTGCACCATACAC 3') (SEQ ID NO: 4); Oligo5: (1221 5'GGTCAACTCTCCAATGTCC 3') (SEQ ID NO: 5); and Oligo6: (1265 5'AGCAAGGTTGCA-CATAGGC 3') (SEQ ID NO: 6). The numbers flanking the sequences mark the targeting region of the DPC4 transcript.
FIG. 10B demonstrates suppression of DPC4 expression by the constructs made from oligonucleotides shown in FIG. 10A.

Applicants first tested the ability of these constructs in suppressing DPC4 expression by performing transient transfections. Each construct was transiently transfected into the pancreatic cancer cell line MiaPaCa-2 (wild-type DPC4) using the Lipofectin Reagent (Invitrogen). DPC4 expression was examined 24 hours after transfection. As shown in FIGS. 10A and 10B, the construct containing Oligo4 showed about 90% DPC4 suppression and the construct with Olig6 showed about 80% DPC4 suppression, whereas the other 4 constructs showed 30-50% DPC4 suppression, indicating that, like antisense oligonucleotides, siRNA also has positional effects.

Figure 11:
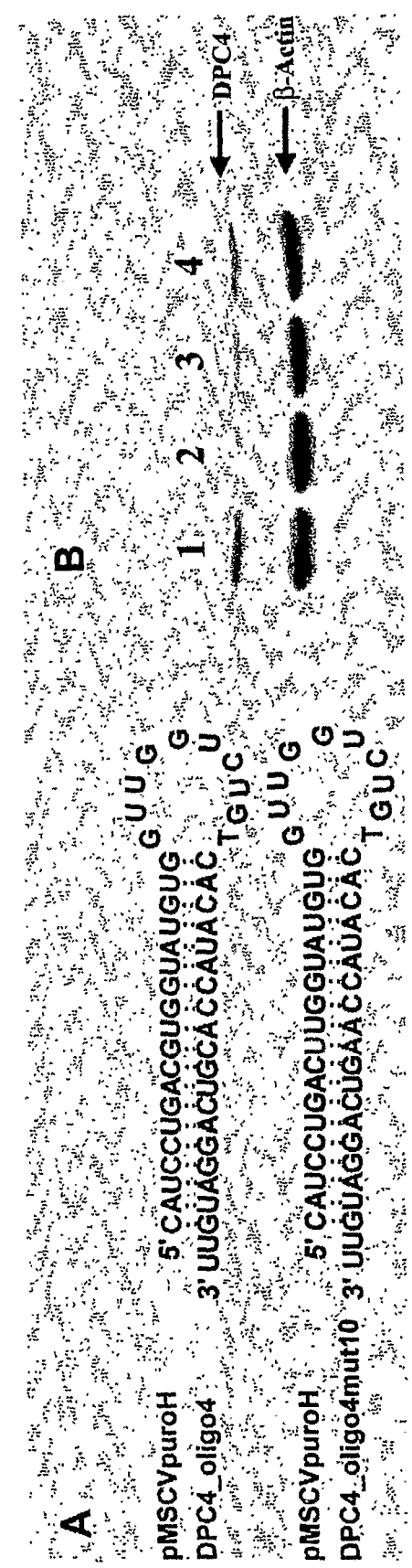
FIG. 11A is a graphic representation of the predicted short hairpin structures formed by the transcripts of pMSCVpuroH—DPC4—oligo4 (5'CAUCCUGACGUG-GUAUGUGGUUGGUCUGTCACAUAC-CACGUCAGGAUGUU 3') (SEQ ID NO: 12) and pMSCVpuroH—DPC4— oligo4mut10(5'CAUCCUGACU-UGGUAUGUGGUUGGUCUGTCACAUAC-CAAGUCAGGAUGUU 3') (SEQ ID NO: 13) inside cells.
FIG. 11B demonstrates DPC4 expression levels detected by Western blot in HPDE6 cells stably transfected with various constructs. Lane 1, An individual clone of HPDE6 cells transfected with pMSCVpuroH (empty vector); Lane 2, An individual clone of HPDE6 transfected with pMSCVpuroH_DPC4_oligo4; Lane 3, Pooled transfectants of HPDE6 transfected with pMSCVpuroH_DPC4_oligo4; Lane 4, An individual clone transfected with pMSCVpuroH_DPC4_oligo4mut10.

Because of its high suppression ability in transient transfections, the construct pMSCVpuroH_DPC4_oligo4 was chosen to generate a cell line with stable DPC4 suppression from HPDE6. To verify the specificity of Oligo4, Applicants created a construct with a mutated Oligo4, Oligo4mut10. The only difference between the two oligos is that the nucleotide residue at position 10 was changed from cytosine in Oligo4 to adenine in Oligo4mut10 (FIG. 11A). After retrovirus infection, HPDE6 cells were selected with puromycin at 3 μg/ml. Individual clones were isolated using serial dilution of the cells in 96-well plates. Ten individual clones for each construct were picked and tested for DPC4 expression at protein level by Western blot. Six out of the 10 individual clones derived from the HPDE6 cells infected with retrovirus from pMSCVpuroH_DPC4_oligo4 showed about 90% DPC4 suppression while 9 out of the 10 individual clones transfected with pMSCVpuroH empty vector had similar DPC4 protein level to that of HPDE6 cells.

FIG. 11B shows the DPC4 expression level detected by Western blot in one of the individual clones of pMSCVpuroH_DPC4_oligo4. Eight passages after the infection, the expression of DPC4 in this clone was still 90% inhibited compared to the HPDE6 cells transfected with the empty vector (HPDE6-vector). This new cell line, which was named HPDE6-siDPC4, along with HPDE6-vector forms a set of isogenic cell lines for the DPC4 gene.

Figure 12:
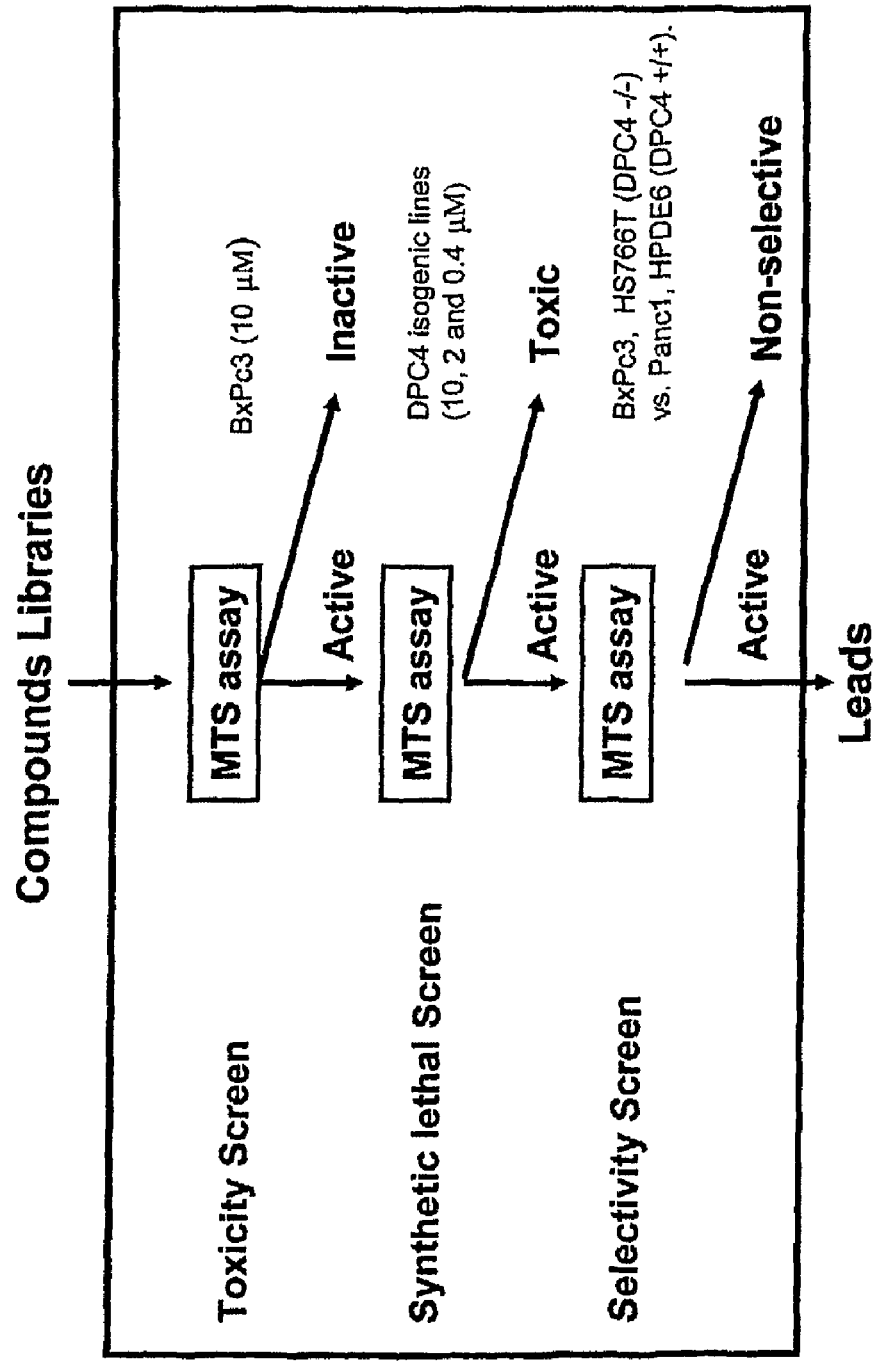
FIG. 12 is a flowchart of steps involved in the high throughput PSLS screening of small molecule libraries for identification of agents specific for DPC4 deficiency.
Figure 16:
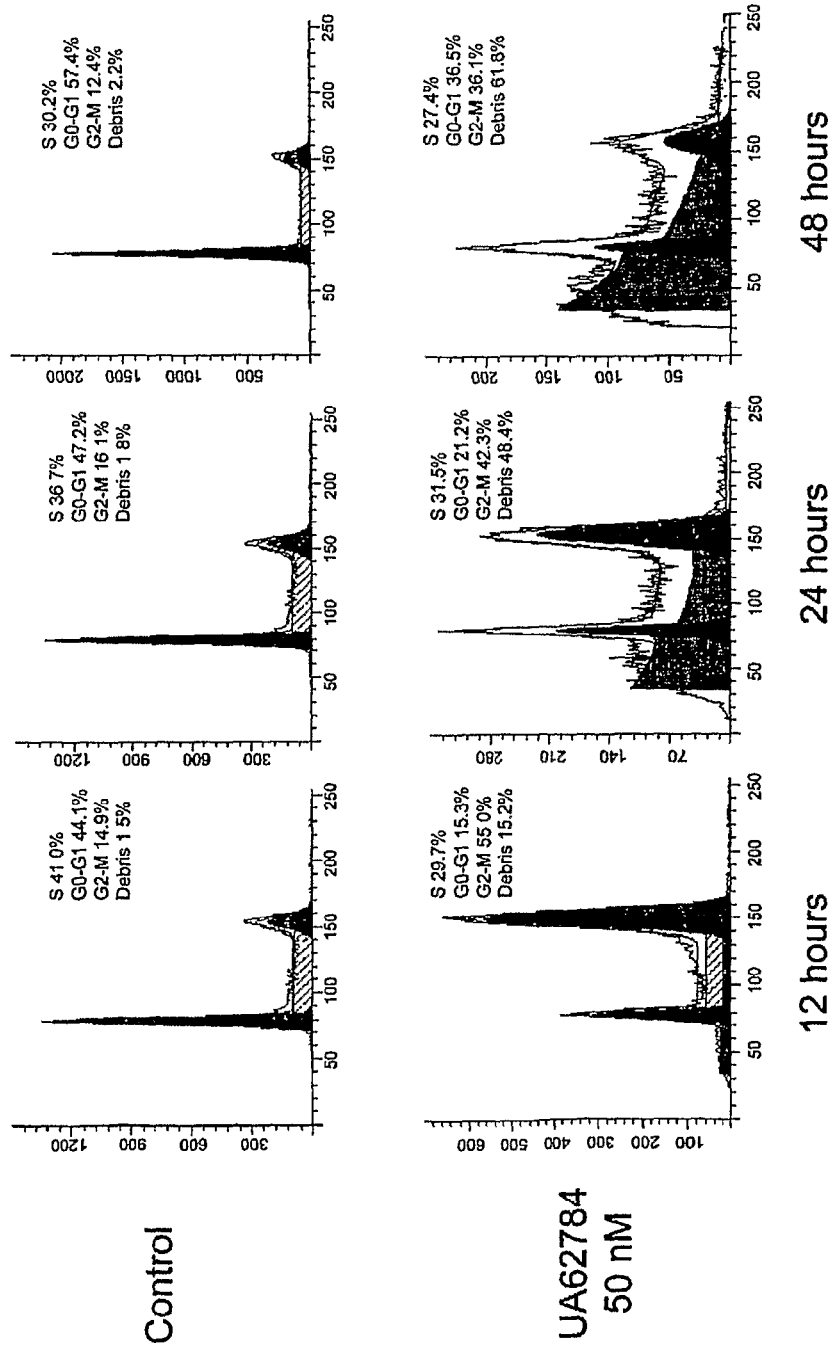
FIG. 16 is a graphic depiction of compound UA62784 induced cell cycle arrest as a function of time.

Screening of Compound Libraries Against the Isogenic Cell Lines for Agents that Selectively Kill Cells with Specific Deficiencies a) The Screening Procedure:

To find molecules that selectively kill cells with specific deficiencies, Applicants use cell proliferation assays to screen molecules libraries in a high throughput manner. These molecule libraries can be small organic compounds, siRNA libraries, antisense libraries and antibody/protein libraries. To carry out the screening in an efficient and cost-effective way, Applicants have designed a procedure for the screening of small organic compound libraries which consists of three steps, namely Toxicity Screen, Synthetic Lethal Screen and Selectivity Screen (FIG. 12).

At the initial screening, compounds are tested in the MTS assay (or other cell proliferation assays such as SRB and Alamar Blue) against the cell line in which the specific gene is either deleted or suppressed by siRNA at a single dose of 10 μM (Toxicity Screening).

Compounds that show more than 50% cell growth inhibition at this concentration are selected to test against both isogenic cell lines (loss-of-function vs. wild type) at three different concentrations (10, 2 and 0.4 μM, Synthetic lethal Screening). Compounds that show a selectivity index ≧5 are selected for next round of screening—Selectivity Screening.

In the Selectivity Screening, compounds are tested against cancer cell lines with a specific loss-of-function mutation and normal cells (HPDE6 and FORF-TERT). Depending on their approximate potency assessed in the Synthetic lethal Screening, compounds are tested in a range of concentrations (8 concentrations per agent) in Selectivity Screening. Compounds that have nM $IC_{50}$ values in loss-of-function cells and selectivity index values >10 are selected for phenotypic consequence tests and in vivo evaluations in animal models.

For screening of siRNA, antisense or antibody libraries, the isogenic cell lines are treated by each agent in parallel under the same conditions and their activities are compared directly through the readout of cell viability. The same criteria described for the screening of small organic compound libraries (FIG. 12) is applied to select positive hits.

b) Identification of Lead Compounds Against DPC4 Deficiency Using Pharmacological Synthetic Lethal Screening:

Using DPC4 isogenic cell lines described earlier, Applicants have applied the procedure depicted in FIG. 12 to identify small organic compounds that selectively kill pancreatic cells with DPC4 deficiency. Applicants have finished three libraries, the NCI diversity library (1,991 compounds) and the NanoSyn Pharm I and IV libraries (17,600 compounds) and identified several leads.

FIG. 3B shows the activity profile of one of the compounds, UA62001, (see FIG. 3A for structural formula) in the isogenic cell line pairs. The $IC_{50}$ values of this compound correlate well with the DPC4 status of the cell lines: HPDE6 (wild-type DPC4), $IC_{50}$>100 µM; BxPc3-DPC4 (reexpression of wild-type DPC4), $IC_{50}$=25 µM; HPDE6-siDPC4 (HPDE6 cells with DPC4 expression stably suppressed by siRNA), $IC_{50}$=6.0 µM; BxPc3Vc (pMSCVneo empty vector), $IC_{50}$=3.0 µM.

To find out if UA62001 has selective effect on DPC4 in other pancreatic cancer cell lines, Applicants further evaluated UA62001 in two other pancreatic cell lines: Panc-1 (DPC4 wildtype) and HS766T (DPC4 deleted). As shown in FIG. 3B, the $IC_{50}$ values of UA62001 are 26 µM in Panc-1 and 3.1 µM in HS766T, which are consistent with the DPC4 status of the cell lines.

Applicants have also identified and confirmed 2 more small molecules that showed selectivity against DPC4 deficiency in the reexpression isogenic cell lines. Their structures and activity profiles are shown in FIGS. 13A and 13B.

Genes Targeted

Theoretically, pharmacological synthetic lethal screening can be used to identify agents that are selective against cancer cells harboring any loss-of-function mutations. However, practically it is desirable to target only the most common loss-of-function mutations. Since different cancer types have different common mutations, it might be necessary to carry screens for individual tumor types. For example, in pancreatic cancer, Applicants proceeded to target p15, p53, DPC4 and BRCA2, whereas in colon cancer Applicants proceeded to target APC-1, E-cadherin and p53.

In addition, because tumorigenesis results from the accumulation of genetic alterations, trying to target a single loss-of-function event may be too simplistic and may not be translatable to human cancers due to the difference of genetic context between engineered cells and patients' tumors. Therefore, engineered cells with the combination of mutations may more accurately reflect the situation that exists in tumor cells. Using engineered cell lines, which contain the most common combination of genetic alterations for pharmacological synthetic lethal screen will more closely resemble patients' tumors and genotype-selective antitumor agents obtained might be more translatable to human ductal adenocarcinomas of pancreas. For example, 95% of the pancreatic adenocarcinomas have activating mutations in the K-ras gene and 95% of the tumors have loss-of-function mutations in p16 gene. Other high frequency genetic alterations in pancreatic cancer include p53 (50%-75%) and DPC4 (50%) (56, 57). It is apparent that pancreatic cancers harbor more than one mutation. As a matter of fact, Rozenblum and coworkers reported that 38% of pancreatic adenocarcinomas have genetic alterations in K-ras, p16, p53 and DPC4 concurrently (66). To identify agents that target this combination of mutations, cell lines that harbor none or all 4 mutations were generated and PSLS screening was carried out using the procedure described in FIG. 12.

Novel Method of Synthesis:

In addition to the synthetic techniques available in the prior art, the present invention further provides an improved method for making the claimed compounds, as well as structurally related derivatives thereof, wherein the improved method allows to efficiently and selectively introduce desired substituents throughout the ring structure to generate compounds of the present invention.

Scheme 1 below describes a general method for producing one of the compounds of the present invention, namely compound named UA62784, via a 4-bromo analogue and intermediate.

Scheme 1: Preparation of UA62784

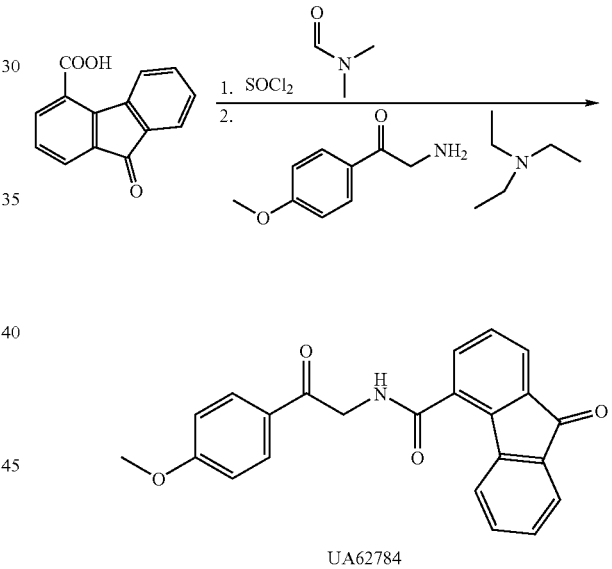

UA62784

Reactants:

| | Reactant | MF | Limit? | MW | Eq | Moles (mmol) | Sample Mass (g) | FM (g/mol) | Reactant Mass (g) |
|---|---|---|---|---|---|---|---|---|---|
| 1 | 9-Fluorenone-4-carboxylic acid | C14H8O3 | No | 224.212 | 1.25 | 50 | 11.21 | 224 | 11.21 |
| 2 | thionyl chloride | Cl2OS | No | 118.970 | 1.25 | 50.0 | 5.95 | 119 | 5.95 |
| 3 | DMF | C3H7NO | No | 73.094 | 0.125 | 5.00 | 0.365 | 73.1 | 0.365 |
| 4 | 2-Amino-4'-methoxyacetophenone Hydrochloride | C9H11NO2 | No | 201.65 g/mol | 1 | 40.0 | 8.07 | 202 | 8.07 |
| 5 | triethyl amine | C6H15N | Yes | 101.190 | 2.5 | 100 | 10.12 | 101 | 10.12 |

Solvents:

| | Name | Solvent Ratio | Volume |
|---|---|---|---|
| 1 | dichloromethane | N/A | 350 mL |

Products:

| | Product | MF | Actual Mass (g) | Actual Mol (mmol) | Yield (%) | Purity | MW | Eq | Theo Mol (mmol) | Theo Mass (g) | FM (g/mol) |
|---|---|---|---|---|---|---|---|---|---|---|---|
| 1 | UA62784 | C23H17NO4 | 12.7 | 34.2 | 85 | | 371.385 | 1.000 | 40.0 | 14.86 | 371 |

Preparation:

To a solution of 9-oxo-9H-fluorene-4-carboxylic acid (11.21 g, 50.0 mmol) in 150 mL DCM, thionyl chloride (11.90 g, 100.0 mmol) and DMF (0.366 g, 5.0 mmol) were added to the solution. The mixture was stirred at reflux for 2 hours. The mixture solution was evaporated in vacuo to remove excess amount of thionyl chloride. The solid residue was dissolved in 200 mL DCM, 2-amino-4'-methoxyacetophenone hydrochloride (8.07 g, 90% purity, 40.0 mmol) was added to the solution and then triethyl amine (10.12 g, 100.0 mmol) was added in portions to the ice-bath solution. The mixture was allowed to stirred at room temperature for 18 hours. The solution solvent was evaporated in vacuo and ethyl ether (100 mL) was added to the residue. The solution was filtered and washed with water, 1N NaOH, 1N HCl and water. The yellow solid was washed with DCM and ethyl acetate repeatedly to obtain the product (12.7 g, 85%). $^1$H NMR (CDCl$_3$) 3.94 (s, 3H), 5.02 (d, J=4.5 Hz, 2H), 7.03 (d, J=9.0 Hz, 2H), 7.16 (bs, 1H, NH), 7.34-7.50 (m, 3H), 7.64 (d, J=7.8 Hz, 1H), 7.72 (d, J=7.5 Hz, 1H), 7.79 (d, J=7.5 Hz, 1H), 7.87 (d, J=8.1 Hz, 1H), 8.05 (d, J=9.0 Hz, 2H).

Step 1 Preparation of 4-Bromo Analog and Intermediate

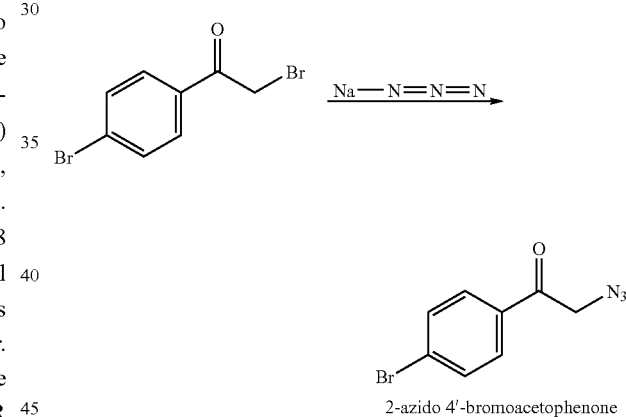

2-azido 4'-bromoacetophenone

Reactants:

| | Reactant | MF | Limit? | MW | Eq | Moles (mmol) | Sample Mass (g) | FM (g/mol) | Reactant Mass (g) |
|---|---|---|---|---|---|---|---|---|---|
| 1 | 2,4'-dibromoacetophenone | C8H6Br2O | Yes | 277.941 | 1.000 | 5.0 | 1.390 | 278 | 1.390 |
| 2 | sodium azide | N3Na | No | 65.010 | 1.000 | 5.00 | 0.325 | 65.0 | 0.325 |

Solvents:

|   | Name | Volume (mL) |
|---|------|-------------|
| 1 | MeOH | 10 |
| 2 | H2O | 10 |

Products:

| | Product | MF | Actual Mass (g) | Actual Mol (mmol) | Yield (%) | MW | Eq | Theo Mol (mmol) | Theo Mass (g) | FM (g/mol) |
|---|---|---|---|---|---|---|---|---|---|---|
| 1 | 2-azido 4'-bromoacetophenone | C8H6BrN3O | 1.0 | 4.17 | 83 | 240.057 | 1.000 | 5.00 | 1.200 | 240 |

Preparation:

A solution of 2,4'-dibromoacetophenone (1.390 g, 5.0 mmol) in MeOH (10 mL) was poured over 10 mL of an aqueous solution of sodium azide (0.325 g, 5.00 mmol) in an ice bath. The mixture was stirred at room temperature for 18 hours. The solvent was removed and then extracted with ethyl ether (20 mL) and water (20 mL). The organic layer was dried over MgSO$_4$ and concentrated in vacuo to obtain 2-azido 4'-bromoacetophenone (1.0 g, 4.17 mmol, 83% yield). $^1$H NMR (CDCl$_3$) 5.45 (s, 2H), 7.67 (d, J=8.4 Hz, 2H), 7.79 (d, J=8.4 Hz, 2H) ppm.

Step 2 Preparation of 2-amino 4'-bromoacetophenone

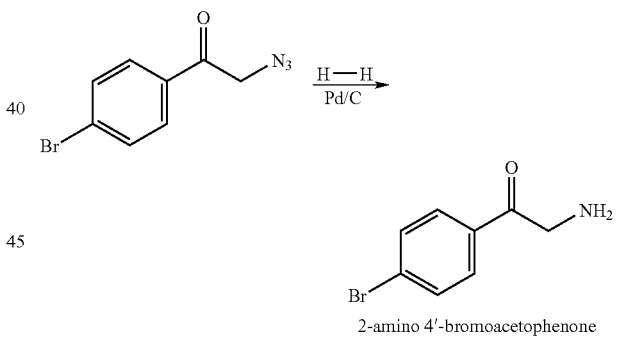

2-amino 4'-bromoacetophenone

Reactants:

| | Reactant | MF | Limit? | MW | Eq | Moles (mmol) | Sample Mass | Vol | Molarity | d | % Wt | FM (g/mol) | Reactant Mass |
|---|---|---|---|---|---|---|---|---|---|---|---|---|---|
| 1 | 2-azido 4'-bromoacetophenone | C8H6BrN3O | Yes | 240.057 | 1.000 | 4.17 | 1.0 g | | | | | 240 | 1.000 g |
| 2 | hydrogen | H2 | No | 2.016 | 1.000 | 4.17 | 8.40 mg | | | | | 2.016 | 8.40 mg |

Solvents:

| Name | Solvent Ratio | Volume |
|------|---------------|--------|
| MeOH |               | 20 mL  |

Products:

| | Product | MF | Actual Mass (g) | Actual Mol (mmol) | Yield (%) | Purity | MW | Eq | Theo Mol (mmol) | Theo Mass (g) | FM (g/mol) |
|---|---------|----|-----|------|----|---|-----|------|------|-------|-----|
| 1 | 2-amino 4'-bromoacetophenone | C8H8BrNO | 0.535 | 2.499 | 60 | | 214.059 | 1.000 | 4.17 | 0.892 | 214 |

Preparation:

To a solution of compound 2-azido 4'-bromoacetophenone (1.0 g, 4.17 mmol) in MeOH (20 mL), Pd/C (10%, 100 mg) was added to the solution. The mixture was degassed and stirred under hydrogen system for 4 hours. The mixture was filtered and evaporated in vacuo without further purification to obtain 2-amino 4'-bromoacetophenone (0.535 g, 2.499 mmol, 60% yield). $^1$H NMR (d-MeOH) 4.63 (d, J=4.8 Hz, 2H), 7.62 (d, J=7.2 Hz, 2H), 8.03 (d, J=7.2 Hz, 2H) ppm.

Step 3 Preparation of UA62784-A1-amide

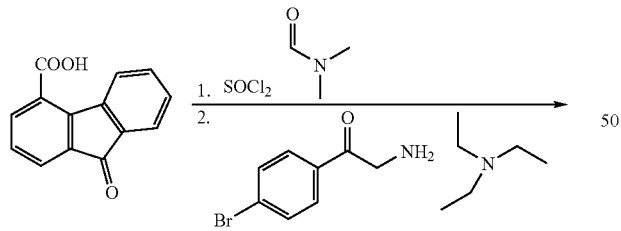

-continued

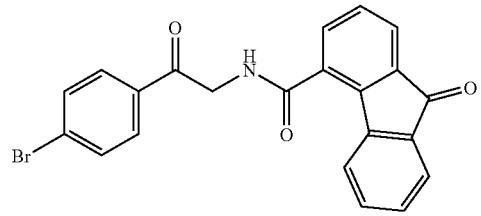

UA62784-A1-amide

Reactants:

| | Reactant | MF | Limit? | MW | Eq | Moles (mmol) | Sample Mass (g) | FM (g/mol) | Reactant Mass (g) |
|---|----------|----|--------|-----|------|--------|-------|-------|-------|
| 1 | 9-fluorenone-4-carboxylic acid | C14H8O3 | Yes | 224.212 | 1.000 | 3.74 | 0.838 | 224 | 0.838 |
| 2 | thionyl chloride | Cl2OS | No | 118.970 | 2 | 7.47 | 0.889 | 119 | 0.889 |
| 3 | DMF | C3H7NO | No | 73.094 | 0.1 | 0.374 | 0.027 | 73.1 | 0.027 |
| 4 | 2-amino 4'-acetophenone | C8H8BrNO | No | 214.059 | 1.000 | 3.74 | 0.8 | 214 | 0.800 |
| 5 | triethylamine | C6H15N | No | 101.190 | 2 | 7.47 | 0.756 | 101 | 0.756 |

Solvents:

| Name | Volume |
|---|---|
| DCM | 20 mL |

Products:

| | Product | MF | Actual Mass (g) | Actual Mol (mmol) | Yield (%) | Purity | MW | Eq | Theo Mol (mmol) | Theo Mass (g) | FM (g/mol) |
|---|---|---|---|---|---|---|---|---|---|---|---|
| 1 | UA62784-A1-amide | C22H14BrNO3 | 0.7 | 1.666 | 44.6 | | 420.255 | 1.000 | 3.74 | 1.571 | 420 |

Preparation:

To a solution of 9-fluorenone-4-carboxylic acid (0.838 g, 3.74 mmol) in 10 mL DCM, thionyl chloride (0.889 g, 7.47 mmol) and DMF (0.027 g, 0.374 mmol) were added to the solution. The mixture was stirred at reflux for 2 hours. The mixture solution was evaporated in vacuo to remove excess amount of thionyl chloride. The solid residue was dissolved in 10 mL DCM, 2-amino 4'-acetophenone (0.8 g, 3.74 mmol) was added to the solution and then triethylamine (0.756 g, 7.47 mmol) was added in portions to the ice-bath solution. The mixture was allowed to be stirred at room temperature for 18 hours. The solution solvent was evaporated in vacuo and ethyl ether (10 mL) was added to the residue. The solution was filtered and washed with water, 1N NaOH, 1N HCl and water. The organic layer was dried over $Mg_2SO_4$, evaporated in vacuo and purified with silica gel chromatography (eluent 100% DCM) to get UA62784-A1-amide (0.7 g, 1.666 mmol, 44.6% yield). $^1$HNMR (CDCl3) 5.08 (d, J=4.5 Hz, 2H), 7.12 (brs, NH), 7.31-7.50 (m, 3H), 7.55-7.73 (m, 4H), 7.79 (d, J=6.6 Hz, 1H), 7.87 (d, J=7.5 Hz, 1H), 8.08 (d, J=7.5 Hz, 2H) ppm.

Step 4 Preparation of UA62784-A1

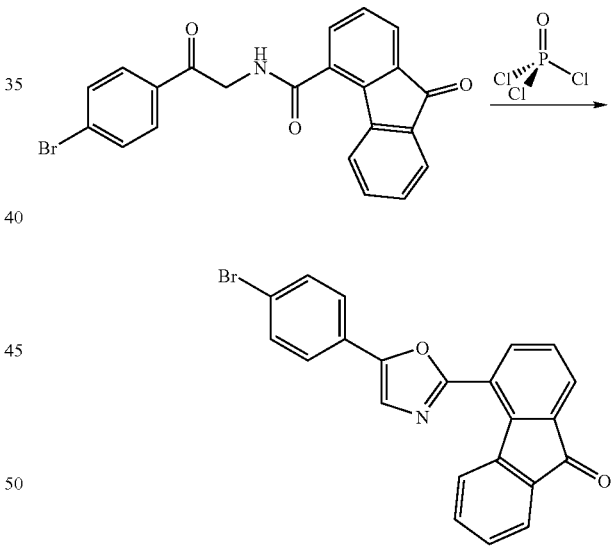

UA62784-A1

Reactants:

| | Reactant | MF | Limit? | MW | Eq | Moles (μmol) | Sample Mass (mg) | FM (g/mol) | Reactant Mass (mg) |
|---|---|---|---|---|---|---|---|---|---|
| 1 | UA62784-A1-amide | C22H14BrNO3 | Yes | 420.255 | 1.000 | 214 | 90 | 420 | 90 |
| 2 | Phosphorus oxychloride | Cl3OP | No | 153.332 | 1.000 | 214 | 32.8 | 153 | 32.8 |

Solvents:

| | Name | Volume (mL) |
|---|---|---|
| 1 | DMF | 10 |

Products:

| | Product | MF | Actual Mass (mg) | Actual Mol (μmol) | Yield (%) | Purity | MW | Eq | Theo Mol (μmol) | Theo Mass (mg) | FM (g/mol) |
|---|---|---|---|---|---|---|---|---|---|---|---|
| 1 | UA62784-A1 | C22H12BrNO2 | 64 | 159 | 74.3 | | 402.240 | 1.000 | 214 | 86 | 402 |

Preparation:

Phosphorus oxychloride (32.8 mg, 214 μmol) was added dropwise to a solution of UA62784-A1-amide (90 mg, 214 μmol) in DMF (10 mL). The mixture was heated to 90° C. for 2 hrs and then poured into ice water (20 mL). The solution was extracted with DCM (20 mL) and combined organic phases were washed with water and brine, dried, and concentrated, followed by purification with silica gel chromatography (eluent 100% DCM) to obtain UA62784-A1 (64 mg, 159 μmol, 74.3% yield) as a yellow solid. $^1$H NMR (CDCl$_3$) 7.34-7.54 (m, 5H), 7.62 (s, 1H), 7.74-7.83 (m, 4H), 8.09 (d, J=7.8 Hz, 1H), 8.60 (d, J=7.8 Hz, 1H) ppm.

The Examples that follow illustrate preferred embodiments of the present invention and are not limiting of the specification and claims in any way.

EXAMPLES

Materials and Methods

Example 1

Cell Culture

Human pancreatic adenocarcinomas cell lines, BxPC-3, PANC-1, CFPAC-1, AsPC-1, Capan-1, Capan-2, Hs 766T, MIA PaCa-2 and SU.86.86 and the normal human primary lung fibroblast cell line, IMR-90, were purchased from the American Type Culture Collection (ATCC, Rockville, Md.). All pancreatic cancer cells were grown in RPMI (Mediatech, Herndon, Va.) with 10% FBS (GEMINI, Woodland, Calif.) and 1% penicillin-streptomycin (Invitrogen, Carlsbad, Calif.). IMR-90 cells were grown in Minimum Essential Medium (Mediatech) with 0.1 mM non-essential amino acids, 10% FBS (GEMINI) and 1% penicillin-streptomycin (Invitrogen). The normal human foreskin fibroblast cell line, Forf, was obtained from the Cell Culture Shared Services at the Arizona Cancer Center (17). Forf was grown in Doulbecco's Modified Eagle Medium (DMEM) with 10% FBS (GEMINI) and 1% penicillin-streptomycin (Invitrogen). The immortalized human pancreas ductal epithelial cell line, HPDE6, was kindly provided by Dr. Ming-Sound Tsao (University of Toronto) (18, 19). HPDE6 cells were maintained in Keratinocyte-SFM supplemented with Epidermal Growth Factor (EGF, 0.2 ng/ml) and Bovine Pituitary Extract (BPE, 30 μg/ml) (Invitrogen).

Example 2

Expression Vector Construction and Retrovirus Based Delivery

The full length cDNA of DPC4 was amplified using RT-PCR with DPC4 forward (5' CACGAATTCATGGA-CAATATGTCTATT 3')(SEQ ID NO: 7) and DPC4 reverse primer (5'ATTCTCGAGTCAGTCTAAAGGTTGTGG 3')(SEQ ID NO: 8) primers containing EcoR I and Xho I restriction enzyme sites respectively. The PCR product was unidirectionally cloned into EcoR I and Xho I sites of the multiple cloning site of pMSCVneo, a retrovirus vector (Clontech, Palo Alto, CA), to generate a DPC4 expression construct, pMSCVneoDPC4. To establish a cell line that constitutively expresses DPC4 gene, pMSCVneoDPC4 was introduced into BxPC-3 cells using the retrovirus delivery system following the manufacture protocol (Clontech). The retrovirus containing the DPC4 gene was produced by co-transfecting the packaging cell line GP2-293 with pVSV-G (Clontech) and pMSCVneoDPC4 using Lipofectin Reagent (Invitrogen). As a negative control, retrovirus containing the pMSCVneo empty vector was also produced. The retrovirus was filtered through a 0.45 μM cellulose acetate membrane syringe filter (Nalgene, Lima, OH) and concentrated for 90 min by ultra-centrifugation at 50,000g. BxPC-3 cells seeded in 6-well plates were infected by the retrovirus in the presence of polybrene (8 μg/ml, Sigma-Aldrich, St. Louis, MO) for 12 hours and then replaced with fresh growth medium. Thirty-six hours after infection, the cells were trypsinized and grown in RPMI medium containing neomycin (G418 at 350 μg/m1) to select positive clones. Ten individual clones were isolated using serial dilution of the cells in 96-well plates. DPC4 expression in individual clones was evaluated using Western blot.

Example 3

Western Blot Analysis

Whole cell extracts were prepared using Nonidet P-40 (NP-40) lysis buffer (1% IGEPAL CA-630, a substitute for NP-40, 150 mM NaCl, 50 mM Tris-HCl [pH 7.4], 2 mM EDTA). For DPC4 protein localization analysis, the nuclei and cytoplasm fractions of the lysates were separated using NE-PER Nuclear and Cytoplasmic Extraction Reagents (PIERCE, Rockford, Ill.). Protein concentrations of the lysates or fractionates were determined using the BCA reagents (PIERCE). Aliquots of the cell lysates or fractionates with equal amount of total protein were resolved on SDS-PAGE gels and transferred onto nitrocellulose membranes. The membranes were then incubated with the primary and HRP conjugated secondary antibodies under the conditions recommended by the manufacturers. DPC4 protein was detected by a monoclonal antibody (Oncogene Research Products, Boston, Mass.). p21 protein was detected by a polyclonal antibody (Cell Signaling Technology, Beverly, Mass.). Both active and proto-form of the caspas-3 were detected by a polyclonal antibody obtained from BD Pharmingen (BD Biosciences Pharmingen, San Diego, Calif.). β-Actin, which served as a loading control was detected by a monoclonal antibody (Sigma). The protein was detected by adding LumiGLO® reagent (chemiluminescent substrate of HRP) and peroxide (Cell Signaling Technology).

Example 4

Anchorage-Independent Growth Assay

BxPC-3-vector cells or BxPC-3-DPC4 cells (3,000 cells per Petri dish) were mixed with Difco agar (final concentration 0.26%) (Clontech) and RPMI medium containing 10% FBS and 1% penicillin-streptomycin, and were overlaid onto an under-layer of 0.45% Difco agar containing RPMI medium, 10% FBS and 1% penicillin-streptomycin in a 35-mm grid Petri dish. The cells were allowed to grow for 19 days at 37° C. before counting the number of colonies ($\geq 8$ cells) under a light microscope. The assay was performed in triplicates. The P values were calculated using a t-test.

Example 5

MTS Based Cell Proliferation Assay

The inhibition of cell proliferation by library compounds was evaluated using the CellTiter 96 Non-Radioactive Cell Proliferation Assay following the protocol recommended by the manufacturer (Promega, Madison Wis.). Briefly, 2000 cells were seeded in each well of 96-well plates in 90 µl growth medium. Cells were allowed to attach overnight followed by addition of 10 µl of serially diluted compounds into the plates. After incubation for 4 days at 37° C. in a humidified incubator, 20 µl of a 20:1 mixture of (3-(4,5-dimethylthiazol-2-yl)-5-(3-carboxymethoxyphenyl)-2-(4-sulfophenyl)-2H-tetrazolium, inner salt (MTS, 2 mg/ml) and an electron coupling reagent, phenazine methosulfate (PMS, 0.92 mg/ml), was added to each well and incubated for 3 hours at 37° C. Absorbance was then measured using the Wallace Victor microplate reader at 490 nm (PerkinElmer, Wellesley, Mass.). Data were expressed as the percentage of cell growth calculated from the absorbance corrected for background absorbance. The surviving fraction of cells was determined by dividing the mean absorbance values of the treated samples by the mean absorbance values of the DMSO control.

Example 6

Compound Libraries

Compound libraries used in the pharmacological synthetic lethal screens consisted of an NCI diversity set (1990 compounds), NanoSyn Pharm II (8,800 compounds) and NanoSyn Pharm IV (8,800 compounds). All the compounds were prepared as 200 µM in DMSO from the stock concentration (1 mM in DMSO for NCI library, 2 mM in DMSO for NanoSyn Pharm libraries) and stored at −20° C. Five microliters of 200 µM compounds were added into 95 µl of cell growth medium for the anti-proliferative assay.

Example 7

Cell Cycle Distribution Analysis

Cells ($5 \times 10^5$) were plated in a T-25 tissue culture flask 24 hours prior to the drug treatment. The cells were treated with UA62001 at 25 µM (about six folds of BxPC-3-vector IC$_{50}$) for 24, 48 and 72 hours. After the treatment, the cells were harvested by trypsinization and centrifugation and then stained with propidium iodide (Sigma) in a modified Krishan buffer (20) for 4 hours at 4° C. The PI stained samples were then analyzed with a FACScan flow cytometer (BD Immunocytometry systems, San Jose, Calif.). Histograms were analyzed for cell cycle compartments and the percentage of cells at each phase of the cell cycle was calculated using CellQuest (BD Immunocytometry systems) analysis software.

Example 8

Annexin V-FITC Apoptosis Assay

Cells were grown and treated with UA62001 as described in the cell cycle distribution analysis section above. Twenty-four hours after the treatment with the compound, cell media containing detached floating cells were transferred to 15 ml conical tubes; while the attached cells were trypsinized and collected in the same tube. Cells were then pelleted by centrifugation at 1500 rpm for 5 min, washed with PBS and then resuspended in 1×binding buffer at a concentration of $1 \times 10^6$ cells/ml. One hundred microliters ($1 \times 10^5$ cells) were incubated with 5 µl of Annexin V-FITC (BD Pharmingen) and propidium iodide for 15 min in the dark at room temperature. After adding 400 µl of the 1× binding buffer, the cells were analyzed by flow cytometry (BD Immunocytometry systems). Data were acquired and analyzed using CellQuest software.

Example 9

DNA Oligo Microarray Analysis

BxPC-3-vector and BxPC-3DPC4 cells ($5 \times 10^5$) were seeded in T-25 cm$^2$ tissue culture flask 24 hours prior to the drug treatment. The cells were then treated with UA62001 at 25µM and harvested by trypsinization after 24 hours. Total RNA of the control and treated samples was isolated using the NucleoSpin RNA Il isolation kit (BD Biosciences, Palo Alto, CA). The microarray analysis including target labeling and chip hybridization and processing was carried out by following the protocols recommended by the chip manufacturer (Agilent Technologies, Palo Alto, CA). Briefly, 1 µg of total RNA was used to generate cyanine 3 (control) or cyanine 5 (drug treated) cRNA targets using the Agilent low input RNA fluorescent linear amplification kit. The concentration and integrity of fluorescent cRNA as well as the incorporation efficiency of cyanine dyes were analyzed using the Agilent Spectrophotometer. Equal amount of labeled cRNA targets from the paired control and treated samples were hybridized onto Agilent Human 1A (V2) oligo array, which contains 21,073 features representing over 21,000 individual human genes and transcripts. The hybridization signals were acquired and normalized using Agilent's Feature Extraction Image Analysis software (v. 7.1). To identify genes whose expression was changed significantly after the drug treatment, the following criteria were used to filter the genes: 1) $\geq 1.5$ fold change upon drug treatment; 2) P value of the Log transformed ratio (PValueLogRatio) $\leq 0.01$ and; 3) the dye normalized signal intensity (DyeNormSignal) $\geq 150$. Venn diagram analysis (Supplementary FIG. 1) was performed for the uniqueness of regulated genes in each of the isogenic cell lines and the overlap of regulated genes between the isogenic cell lines using GeneSpring 7.2 (Agilent). The microarray data was submitted into Gene Expression Omnibus (GEO) with GEO accession number, GSE2646.

Example 10

Validation of Array Data by Real--Time Rt-Pcr

Real time PCR primers for each of the tested genes were designed using the Primer3software. Two micrograms of total RNA isolated from the control and drug treated samples were used in a 20 μl reverse transcription reaction to generate cDNA using the First Strand cDNA Synthesis Kit (Fermentas, Hanover, MD). To perform the real time PCR, 1.5 μl of the RT reaction was mixed with 1 μl of primer mixture (5 μM), 10 μl of water and 12.5 μl of 2 X QuantiTect SYBR PCR Master Mix (Qiagen, Valencia CA). Each sample was subjected to 40 cycles of amplification on an Opticon I real time thermocycler (Bio-Rad Laboratories, Hercules, CA). The transcript abundance of each gene was calculated and normalized to β-Actin using the algorithm provided by the Thermocycler manufacturer.

Results

Example 11

Ectopic expression of DPC4 gene in BxPC3 cells

To restore the function of DPC4 gene in the pancreatic cell line, BxPC3, in which DPC4 gene was homozygously deleted, Applicants used a retrovirus-based vector to ectopically express the wild-type DPC4 gene. To establish a stable cell line that constitutively expresses DPC4, pMSCV-neoDPC4 was introduced into BxPC-3 cells through the retrovirus delivery system described earlier in Example 2. Ten individual clones were isolated using serial dilution of the cells in 96-well plates under G418 selection (350 μg/ml). DPC4 expression in individual clones was evaluated by Western blot using DPC4 monoclonal antibody. The DPC4 expression level of one individual clone, named BxPC-3-DPC4, as shown in FIG. 1A, has a DPC4 expression level that is comparable to that in the immortalized HPDE6 cells. As a negative control, the pMSCVneo empty vector was also delivered into BxPC-3 cells by the retrovirus to create the BxPC-3-vector cell line. Thus, BxPC-3-vector and BxPC3-DPC4 are considered as a pair of DPC4 isogenic cell lines.

Example 12

Characterization of the DPC4 Isogenic Cell Lines

To verify that the ectopic expression of DPC4 has functionally restored the TGF-β pathway, Applicants carried out a series of experiments to evaluate the DPC4 function in BxPC-3-DPC4 cells. Firstly, the cell morphology of BxPC-3-DPC4 was inspected under light microscope and was found to be very similar to that of the parental cell line BxPC-3 except that the proliferation rate of BxPC-3-DPC4 cells was slightly slower than that of BxPC-3 cells (FIG. 1D).

Secondly, Applicants investigated the localization of DPC4 protein in the BxPC-3-DPC4 cells upon the treatment of TGF-β cytokine. Applicants observed that DPC4 protein was localized to the nucleus upon TGF-β treatment in the BxPC-3-DPC4 cells but not in the BxPC-3-vector cells (FIG. 1B), which is consistent with the previous reports (21, 22).

Thirdly, Applicants examined the protein levels of p21 in the isogenic cell lines. p21 is a cyclin-dependent kinase inhibitor whose expression was shown to be up-regulated when DPC4 function was restored (22). As expected, the p21 protein level was increased significantly in the BxPC-3-DPC4 cells compared to the BxPC-3-vector cells (FIG. 1C). Finally, we evaluated the tumorigenicity of the BxPC-3-DPC4 cells using a soft-agar growth assay. As shown in FIG. 1E, the ectopic expression of DPC4 in the BxPC-3-DPC4 cells dramatically suppressed the anchorage-independent growth of the cells (more than 70% reduction in colony numbers, p value=0.0025).

In addition, Applicants investigated the growth response of BxPC-3-DPC4 cells to TGF-β cytokine and did not observe any apparent TGF-β induced cell growth inhibition in BxPC-3-DPC4. Although this observation is different from what has been seen in the PANC-1 cell line which has wildtype DPC4, it is consistent with reported data from studies that dealt with DPC4 restoration in other pancreatic cancer cell lines such as CFPAC-1 and Hs 766T (21, 22). Together, these results demonstrate that the ectopic expression of DPC4 has restored the TGF-β signaling pathway in the BxPC-3-DPC4 cells.

Example 13

Identification of a Genotype-Selective Compound Against the DPC4 Deficiency Through Pharmacological Synthetic Lethal Screening (PSLS)

Figure 2:
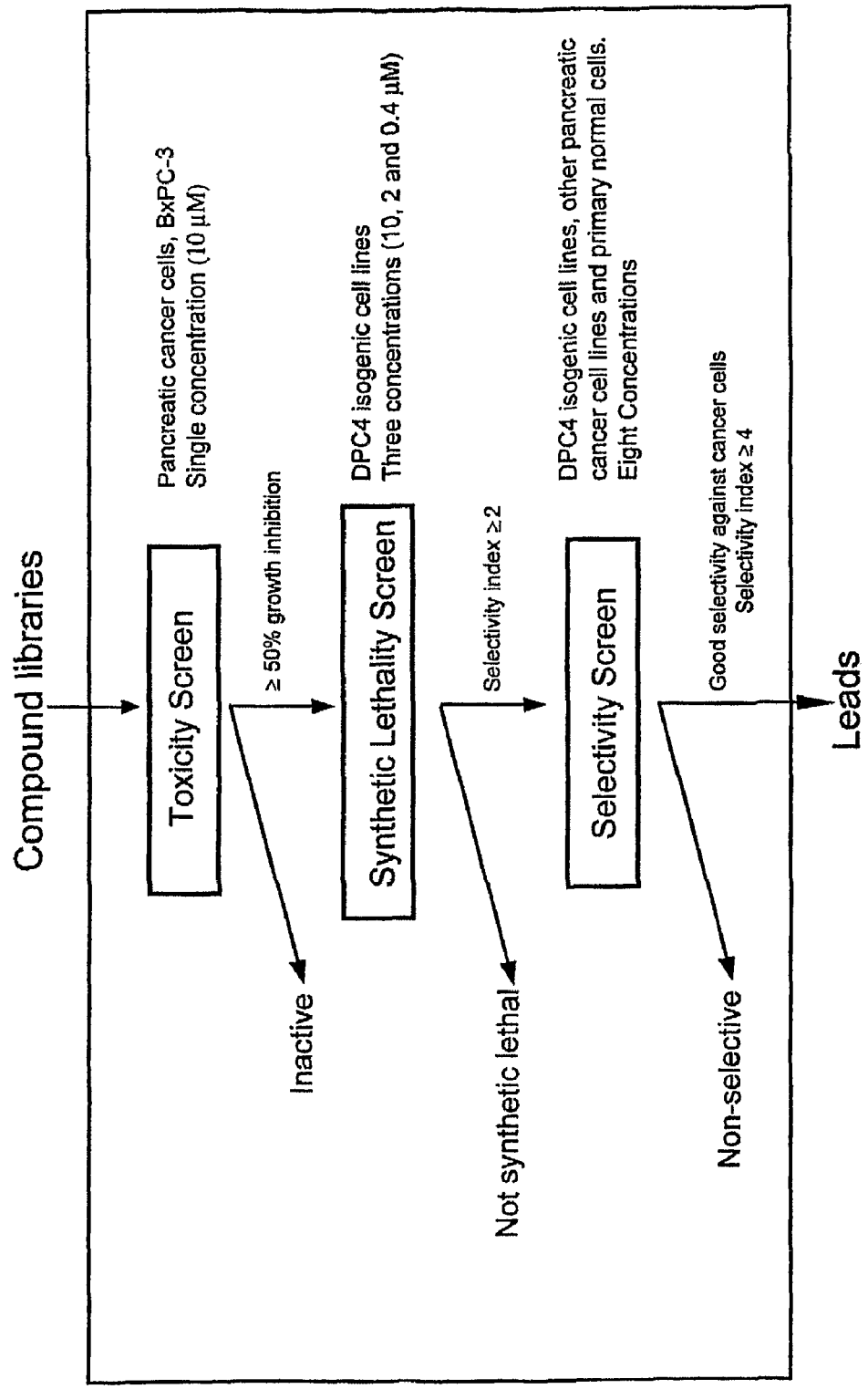
FIG. 2 is a schematic depiction of the method for screening and identification of compounds able to selectively eliminate cancer cells with specific loss-of-function alterations.

After generating the isogenic cell lines for the DPC4 gene, Applicants then carried out a screening process using the cell lines with the aim to identify compounds that selectively kill cells with deficient DPC4 function. The screen process, which was named pharmacological synthetic lethality screening (PSLS), consisted of three rounds of screening, namely, Toxicity Screen, Synthetic Lethality Screen and Selectivity Screen (FIG. 2). In each round, the anti-proliferative activity of compounds was evaluated in different cell lines using the CellTiter 96 Non-Radioactive Cell Proliferation Assay (Promega). In the Toxicity Screen, compounds were evaluated in the BxPC-3 parental cell line at a single concentration of 10 μM. Generally, cancer cell lines, especially highly chemoresistant pancreatic cancer cell lines, have significant variation in their sensitivities to antitumor agents. To ensure that potential lead compounds to be identified exhibited significant antitumor activity, Applicants used this screen against the parental line to eliminate compounds that have low anti-proliferative activity. After screening three compound libraries, the NCI diversity set (1,990 compounds), NanoSyn Pharm II (8,800 compounds) and NanoSyn Pharm IV (8,800 compounds), Applicants identified a total of 200 compounds that showed ≧50% growth inhibition against the BxPC-3 cells at 10 μM. These compounds were then subjected to the second round of screen, the Synthetic Lethality Screening. In this round of screening, each compound was tested against both of the DPC4 isogenic cell lines (BxPC-3-vector and BxPC-3-DPC4) at three different concentrations (10, 2 and 0.4 μM; if even 0.4 μM was too high for a compound, lower testing concentrations were used) in triplicates. The activities of a compound in the DPC4 isogenic cell lines were calculated and a selectivity index was determined for each concentration (Selectivity index=Percentage cell survival in BxPC-3-DPC4 cells/Percentage cell survival in BxPC-3-vector cells). To select compounds for further evaluation in the third round of screening, we set the selection criteria as percentage inhibition in the BxPC-3-vector cells ≧50 and selectivity index >2 at least at one of the 3 concentrations. Among the 200 compounds selected from Toxicity Screening, 10 compounds were selected based on these criteria. These ten compounds were further evaluated in third round of screening, the Selectivity screening. In this screening, compounds were tested against a panel of cell lines including the DPC4 isogenic cell lines, pancreatic cancer cell lines CFPAC-1, Hs766T and PANC-1, and normal human primary cell lines IMR-90 and Forf, at eight different concentrations (concentration range was determined based on the compound potency from the synthetic lethality screening). After three rounds of PSLS screening, one compound, UA62001, 2-phenyl-1H-Naphth [2,3-g]indazole-3,6,11

(2H)-trione, was identified to have DPC4 genotype selectivity. The activity profile of UA62001 in DPC4 isogenic cell lines was shown in FIG. 3. UA62001 has an $IC_{50}$ value at 3.2±0.5 μM in BxPC-3-vector cells and $IC_{50}$ value at 14.7±4.3 μM in BxPC-3-DPC4 cells. To exclude the possibility that such sensitivity difference is a result of random clonal variability of the DPC4 reexpressing cells, Applicants tested UA62001 in two more stable clones of BxPC-3-DPC4 cells. The $IC_{50}$ values of UA62001 in these clones are very similar to that in the original clone.

Applicants further examined the anti-proliferative activity of UA62001 in a panel of cell lines including normal cell lines which have wildtype DPC4 and pancreatic cancer lines with either wildtype DPC4 or inactivated DPC4 (Table 1). UA62001 has low μM $IC_{50}$ values in pancreatic cancer cell lines, but show little growth inhibition against normal human primary cell lines, Forf and IMR-90, even at 200 μM. Because of the high aneuploidy and diverse genetic background in the pancreatic cancer cells, it is rather surprising to see such good correlation between the genetic and expression status of DPC4 and UA62001 sensitivity (See Table 1).

Example 14

Potential Mechanism of Action of the Lead Compound

Although lead compounds identified from the PSLS selectively kill cancer cells harboring DPC4 deficiency, the lethality screening does not tell one how the agents might exert its killing effects. To elucidate the possible mechanism of action of the lead compound, Applicants investigated the cellular responses of BxPC-3 cells to UA62001 treatment using cell cycle analysis and apoptosis assays.

Figure 4:
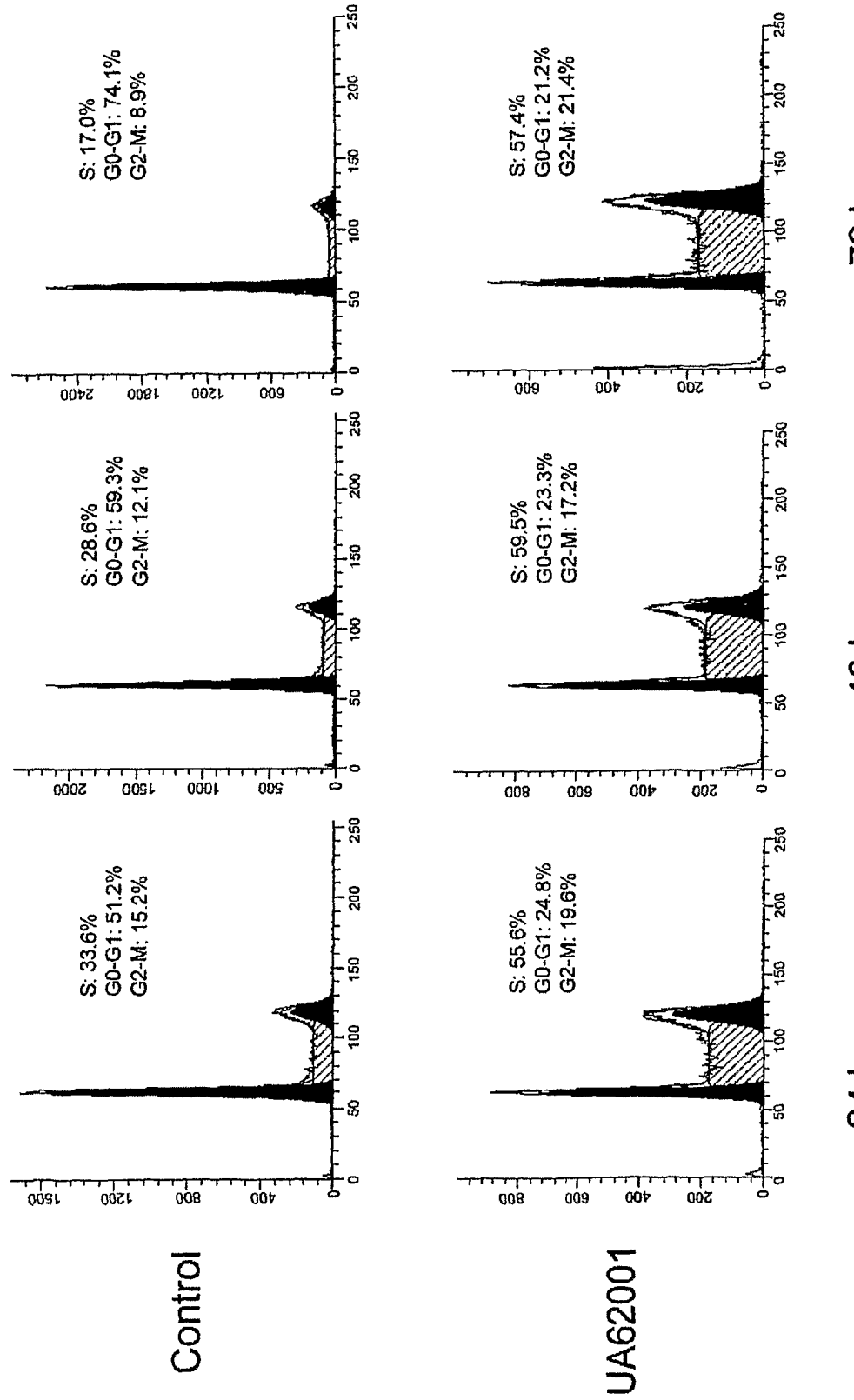
FIG. 4 is a graphic depiction of the cell cycle distribution of UA62001 treated cells.

In the cell cycle distribution analysis, BxPC-3 cells were treated with UA62001 at 25 μM in a time course up to 72 hours. UA62001 treatment arrested more cells in S and G2-M phases. As shown in FIG. 4, BxPC-3 cells treated with UA62001 had a significant increase in G2/M phase population (~20% for treated sample vs. ~10% for untreated control). The cell population in S phase was much higher for UA62001 treated samples than for control samples after the treatment of 24, 48 and 72 hours (55.6%, 59.5% and 57.4% vs. 33.6%, 28.6% and 17.0% for each time point) (FIG. 4). However, this cell cycle arrest effect does not seem to be time-dependent.

Figure 5:
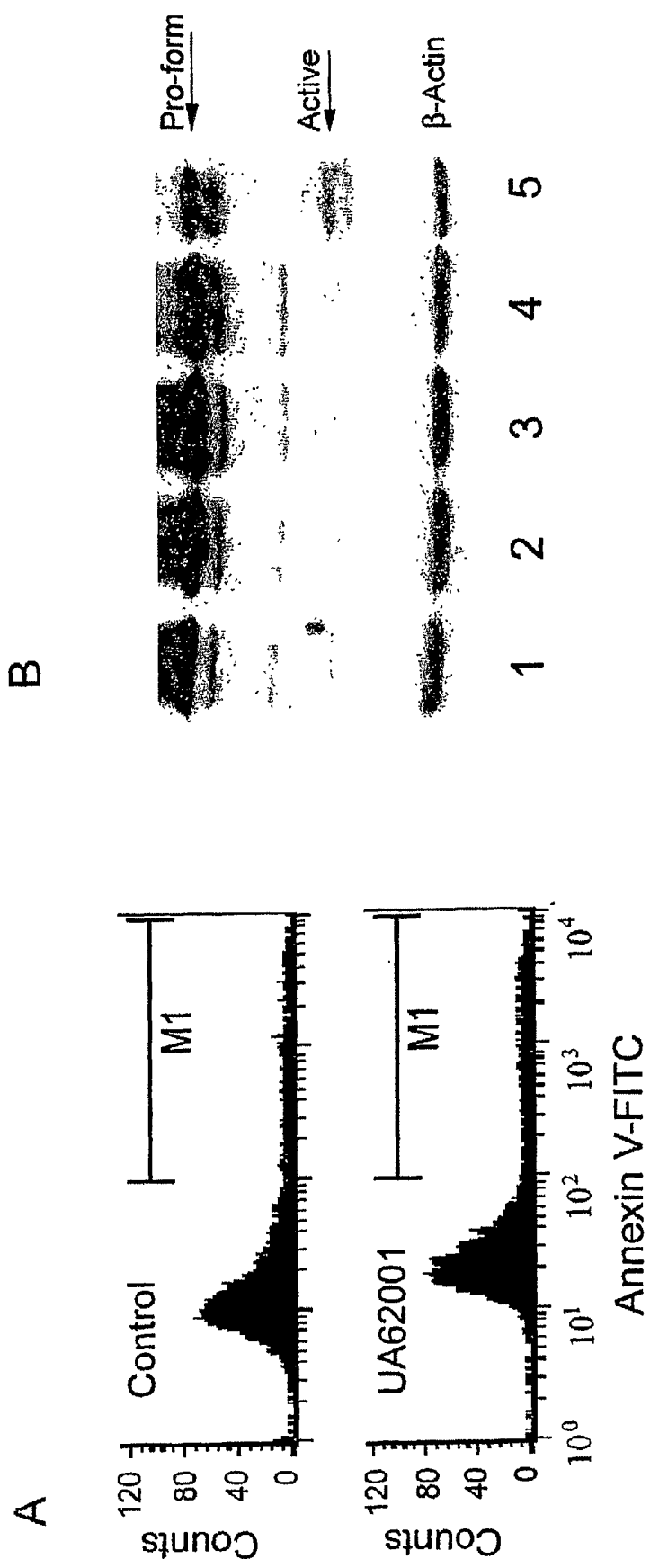
FIG. 5 demonstrates analysis of the apoptosis of UA62001 treated cells.

UA62001 does not appear to be a strong apoptosis inducer. Using the Annexin V staining, we only detected a very modest increase in cell population that fell into the M1 region after UA62001 treatment (8.2%) compared to 4.6% in the untreated control (FIG. 5A). In addition, caspase-3 activation analysis showed that UA62001 did not induce the cleavage of proto-form of caspase-3 (FIG. 5B), indicating that induction of apoptosis might not be the main mechanism by which UA62001 exerts its anti-proliferative activity.

Example 15

Differential Gene Expression Changes in DPC4 Isogenic Cell Lines after UA62001 Treatment To explore the molecular bases of the genotype selectivity of UA62001, Applicants compared the gene expression profiles of DPC4 isogenic cell lines before and after UA62001 treatment using an Agilent oligo microarray. The transcripts of 166 genes (represented by 203 probes on the microarray chip) in BxPC-3-DPC4 cells and 308 genes (represented by 364 probes) in BxPC-3-vector cells were significantly changed upon the UA62001 treatment (FIG. 1). Among these differentially expressed genes, only twenty five were common between the two isogenic cell lines. To find the targets or pathways whose gene expression was regulated by UA62001 treatment might contribute to the genotype selectivity, Applicants analyzed the genes uniquely regulated in each of the isogenic cell lines using the BioRag informatics tool developed by Dr. David Mount et al. at the University of Arizona (www.biorag.org). One pathway that emerged from this analysis is the cell cycle regulatory pathway. CDC2 gene expression was identified as only changed in BxPC-3-vector cells not in BxPC-3-DPC4 cells after UA62001 treatment. However, closer examination of the microarray data showed that CDC2 was also down-regulated in the BxPC-3-DPC4 cells, but to a lesser degree. Cyclin B1 (CCNB1) and cyclin B2 (CCNB2), which formed the complex with CDC2, had the same pattern as CDC2 in response to UA62001 treatment, down-regulated in both DPC4 isogenic cell lines, but by different degrees (Table 2). The Mini-chromosome maintenance complex (MCM) also showed the similar pattern of gene expression changes in the isogenic cell lines as the cyclin B/CDC2 complex after UA62001 treatment. All six members of the hexameric MCM complex (MCM2-7) were differentially down-regulated in both DPC4 isogenic cell lines (Table 2) and the degree of down-regulation was always higher in the BxPC-3-vecter cells than in BxPC-3-DPC4 cells. Real-time quantitative RT-PCR analysis further confirmed the expression changes of these genes (Table 2).

Equivalents:

While this invention has been particularly shown and described with references to preferred embodiments thereof, it will be understood by those skilled in the art that various changes in form and details may be made therein without departing from the scope of the invention encompassed by the appended claims.

Advantages of the Invention:

The present invention provides a rapid, efficient method for screening and identification of large numbers of compounds capable of selective elimination of cancer cells exhibiting specific loss-of-function alterations. Compounds determined to possess such selective ability to eliminate cancer cells with specific loss-of-function alterations according to the present invention are likely to be useful in treating various types of cancer, including but not limited to pancreatic cancer, colon cancer, adenomas, intramucosal carcinomas, invasive carcinomas without distant metastasis, primary invasive carcinomas with distant metastases, and carcinomas metastasized to the liver or distant lymph nodes.

Moreover, the present invention also provides novel compounds that selectively eliminate cancer cells with specific loss-of-function alterations including but not limited to mutations, deletions, hypermethylations and other types of gene silencing. These compounds may be used in a variety of pharmaceutical compositions designed to treat certain types of cancer and other adverse conditions associated with tumorigenic cell proliferation.

Additionally, the present invention also provides useful methods for the efficient preparation of compound able to selectively eliminate cancer cells with loss-of-function alterations, as well as methods for therapeutic use of such compounds. The compounds, methods of screening, methods of preparation, and methods of therapeutic use disclosed in the present invention will have great utility and application in the pharmaceutical, medical, and similarly related arts. The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications, are incorporated herein by reference.

References:

The following references are cited in the specification and Examples by reference number; all of these references are incorporated by this reference in the application in their entirety:

1. Jaffee, E. M., Hruban, R. H., Canto, M., and Kern, S. E. Focus on pancreas cancer. Cancer Cell, 2: 25-28, 2002.
2. Jemal, A., Murray, T., Ward, E., Samuels, A., Tiwari, R. C., Ghafoor, A., Feuer, E. J., and Thun, M. J. Cancer statistics, 2005. CA Cancer J Clin, 55:10-30, 2005.
3. Rothenberg, M. L., Moore, M. J., Cripps, M. C., Andersen, J. S., Portenoy, R. K., Burris, H. A., 3rd, Green, M. R., Tarassoff, P. G., Brown, T. D., Casper, E. S., Storniolo, A. M., and Von Hoff, D. D. A phase II trial of gemcitabine in patients with 5-FU-refractory pancreas cancer. Ann Oncol, 7: 347-353, 1996.
4. Hahn, S. A., Hoque, A. T., Moskaluk, C. A., da Costa, L. T., Schutte, M., Rozenblum, E., Seymour, A. B., Weinstein, C. L., Yeo, C. J., Hruban, R. H., and Kern, S. E. Homozygous deletion map at 18q21.1 in pancreatic cancer. Cancer Res, 56:490-494, 1996.
5. Rozenblum, E., Schutte, M., Goggins, M., Hahn, S. A., Panzer, S., Zahurak, M., Goodman, S, N., Sohn, T. A., Hruban, R. H., Yeo, C. J., and Kern, S. E. Tumor-suppressive pathways in pancreatic carcinoma. Cancer Res, 57: 1731-1734, 1997.
6. Bartsch, D., Hahn, S. A., Danichevski, K. D., Ramaswamy, A., Bastian, D., Galehdari, H., Barth, P., Schmiegel, W., Simon, B., and Rothmund, M. Mutations of the DPC4/Smad4 gene in neuroendocrine pancreatic tumors. Oncogene, 18:2367-2371, 1999.
7. Miyaki, M. and Kuroki, T. Role of Smad4 (DPC4) inactivation in human cancer. Biochem Biophys Res Commun, 306: 799-804, 2003.
8. Luttges, J., Galehdari, H., Brocker, V., Schwarte-Waldhoff, I., Henne-Bruns, D., Kloppel, G., Schmiegel, W., and Hahn, S. A. Allelic loss is often the first hit in the biallelic inactivation of the p53 and DPC4 genes during pancreatic carcinogenesis. Am J Pathol, 158:1677-1683, 2001.
9. Wilentz, R. E., Iacobuzio-Donahue, C. A., Argani, P., McCarthy, D. M., Parsons, J. L., Yeo, C. J., Kern, S. E., and Hruban, R. H. Loss of expression of Dpc4 in pancreatic intraepithelial neoplasia: evidence that DPC4 inactivation occurs late in neoplastic progression. Cancer Res, 60: 2002-2006, 2000.
10. Tascilar, M., Skinner, H. G., Rosty, C., Sohn, T., Wilentz, R. E., Offerhaus, G. J., Adsay, V., Abrams, R. A., Cameron, J. L., Kern, S. E., Yeo, C. J., Hruban, R. H., and Goggins, M. The SMAD4 protein and prognosis of pancreatic ductal adenocarcinoma. Clin Cancer Res, 7: 4115-4121, 2001.
11. Heinmoller, E., Dietmaier, W., Zirngibl, H., Heinmoller, P., Scaringe, W., Jauch, K. W., Hofstadter, F., and Ruschoff, J. Molecular analysis of microdissected tumors and pre-neoplastic intraductal lesions in pancreatic carcinoma. Am J Pathol, 157: 83-92, 2000.
12. Miyaki, M., Iijima, T., Konishi, M., Sakai, K., Ishii, A., Yasuno, M., Hishima, T., Koike, M., Shitara, N., Iwama, T., Utsunomiya, J., Kuroki, T., and Mori, T. Higher frequency of Smad4 gene mutation in human colorectal cancer with distant metastasis. Oncogene, 18: 3098-3103, 1999.
13. Maitra, A., Molberg, K., Albores-Saavedra, J., and Lindberg, G. Loss of Dpc4 expression in colonic adenocarcinomas correlates with the presence of metastatic disease. Am J Pathol, 157: 1105-1111, 2000.
14. Shi, Y., Gera, J., Hu, L., Hsu, J. H., Bookstein, R., Li, W., and Lichtenstein, A. Enhanced sensitivity of multiple myeloma cells containing PTEN mutations to CCI-779. Cancer Res, 62: 5027-5034, 2002.
15. Dolma, S., Lessnick, S. L., Hahn, W. C., and Stockwell, B. R. Identification of genotype-selective antitumor agents using synthetic lethal chemical screening in engineered human tumor cells. Cancer Cell, 3: 285-296, 2003.
16. van der Heijden, M. S., Brody, J. R., Gallmeier, E., Cunningham, S. C., Dezentje, D. A., Shen, D., Hruban, R. H., and Kern, S. E. Functional defects in the fanconi anemia pathway in pancreatic cancer cells. Am J Pathol, 165:651-657, 2004.
17. Rojanala, S., Han, H., Munoz, R. M., Browne, W., Nagle, R., Von Hoff, D. D., and Bearss, D. J. The mitotic serine threonine kinase, Aurora-2, is a potential target for drug development in human pancreatic cancer. Mol. Cancer Ther., 3: 451-457, 2004.
18. Ouyang, H., Mou, L., Luk, C., Liu, N., Karaskova, J., Squire, J., and Tsao, M. S. Immortal human pancreatic duct epithelial cell lines with near normal genotype and phenotype. Am J Pathol, 157: 1623-1631, 2000.
19. Liu, N., Furukawa, T., Kobari, M., and Tsao, M. S. Comparative phenotypic studies of duct epithelial cell lines derived from normal human pancreas and pancreatic carcinoma. Am J Pathol, 153: 263-269, 1998.
20. Krishan, A. Rapid flow cytofluorometric analysis of mammalian cell cycle by propidium iodide staining. J Cell Biol, 66:188-193, 1975.
21. Chen, W. B., Lenschow, W., Tiede, K., Fischer, J. W., Kalthoff, H., and Ungefroren, H. Smad4/DPC4-dependent regulation of biglycan gene expression by transforming growth factor-beta in pancreatic tumor cells. J Biol Chem, 277: 36118-36128, 2002.
22. Dai, J. L., Bansal, R. K., and Kern, S. E. G1 cell cycle arrest and apoptosis induction by nuclear Smad4/Dpc4: phenotypes reversed by a tumorigenic mutation. Proc Natl Acad Sci USA, 96:1427-1432, 1999.
23. Workman, P. Towards intelligent anticancer drug screening in the post-genome era? Anticancer Drug Des, 12: 525-531, 1997.
24. Hurley, L. H. DNA and its associated processes as targets for cancer therapy. Nat Rev Cancer, 2:188-200, 2002.
25. Blundell, T. L. Structure-based drug design. Nature, 384: 23-26, 1996.
26. Beeley, L. J. and Duckworth, D. M. The impact of genomics on drug design. Drug Discovery Today, 1: 474-480, 1996.
27. Bevan, P., Ryder, H., and Shaw, I. Identifying small-molecule lead compounds: the screening approach to drug discovery. Trends Biotechnol, 13:115-121, 1995.
28. Vassilev, L. T., Kazmer, S., Marks, l. M., Pezzoni, G., Sala, F., Mischke, S. G., Foley, L., and Berthel, S. J. Cell-based screening approach for antitumor drug leads which exploits sensitivity differences between normal and cancer cells: identification of two novel cell-cycle inhibitors. Anticancer Drug Des, 16:7-17, 2001.
29. Holbeck, S. L. Update on NCI in vitro drug screen utilities. Eur J Cancer, 40:785-793, 2004.
30. Boyd, M. R., Paull, K. D. Some practical considerations and applications of the national cancer institute in vitro anticancer drug discovery screen. Drug Development Research, 34: 91-109, 1995.
31. Broach, J. R. and Thorner, J. High-throughput screening for drug discovery. Nature, 384: 14-16, 1996.
32. Druker, B. J., Tamura, S., Buchdunger, E., Ohno, S., Segal, G. M., Fanning, S., Zimmermann, J., and Lydon, N. B. Effects of a selective inhibitor of the Abl tyrosine kinase on the growth of Bcr-Abl positive cells. Nat Med, 2: 561-566, 1996.
33. Capdeville, R., Buchdunger, E., Zimmermann, J., and Matter, A. Glivec (STI571, imatinib), a rationally developed, targeted anticancer drug. Nat Rev Drug Discov, 1: 493-502, 2002.
34. Mokbel, K. and Hassanally, D. From HER2 to herceptin. Curr Med Res Opin, 17: 51-59, 2001.
35. Doye, V. and Hurt, E. C. Genetic approaches to nuclear pore structure and function. Trends Genet, 11: 235-241, 1995.
36. Forsburg, S. L. The art and design of genetic screens: yeast. Nat Rev Genet, 2: 659-668, 2001.
37. Hartwell, L. H., Szankasi, P., Roberts, C. J., Murray, A. W., and Friend, S. H. Integrating genetic approaches into the discovery of anticancer drugs. Science, 278:1064-1068, 1997.
38. Friend, S. H. and Oliff, A. Emerging uses for genomic information in drug discovery. N Engl J Med, 338:125-126, 1998.
39. Peng, B., Fleming, J. B., Breslin, T., Grau, A. M., Fojioka, S., Abbruzzese, J. L., Evans, D. B., Ayers, D., Wathen, K., Wu, T., Robertson, K. D., and Chiao, P. J. Suppression of tumorigenesis and induction of p15(ink4b) by Smad4/DPC4 in human pancreatic cancer cells. Clin Cancer Res, 8: 3628-3638, 2002.
40. Venkatasubbarao, K., Ammanamanchi, S., Brattain, M. G., Mimari, D., and Freeman, J. W. Reversion of transcriptional repression of Sp1 by 5 aza-2' deoxycytidine restores TGF-beta type II receptor expression in the pancreatic cancer cell line MIA PaCa-2. Cancer Res, 61: 6239-6247, 2001.
41. Sipos, B., Moser, S., Kalthoff, H., Torok, V., Lohr, M., and Kloppel, G. A comprehensive characterization of pancreatic ductal carcinoma cell lines: towards the establishment of an in vitro research platform. Virchows Arch, 442:444-452, 2003.
42. Schutte, M., Hruban, R. H., Hedrick, L., Cho, K. R., Nadasdy, G. M., Weinstein, C. L., Bova, G. S., Isaacs, W. B., Cairns, P., Nawroz, H., Sidransky, D., Casero, R. A., Jr., Meltzer, P. S., Hahn, S. A., and Kern, S. E. DPC4 gene in various tumor types. Cancer Res, 56: 2527-2530, 1996.
43. Moore, P. S., Sipos, B., Orlandini, S., Sorio, C., Real, F. X., Lemoine, N. R., Gress, T., Bassi, C., Kloppel, G., Kalthoff, H., Ungefroren, H., Lohr, M., and Scarpa, A. Genetic profile of 22 pancreatic carcinoma cell lines. Analysis of K-ras, p53, p16 and DPC4/Smad4. Virchows Arch, 439: 798-802, 2001.
44. Draetta, G., Luca, F., Westendorf, J., Brizuela, L., Ruderman, J., and Beach, D. Cdc2 protein kinase is complexed with both cyclin A and B: evidence for proteolytic inactivation of MPF. Cell, 56: 829-838, 1989.
45. Giordano, A., Whyte, P., Harlow, E., Franza, B. R., Jr., Beach, D., and Draetta, G. A 60 kd cdc2-associated polypeptide complexes with the E1A proteins in adenovirus-infected cells. Cell, 58: 981-990, 1989.
46. Morla, A. O., Draetta, G., Beach, D., and Wang, J. Y. Reversible tyrosine phosphorylation of cdc2: dephosphorylation accompanies activation during entry into mitosis. Cell, 58:193-203, 1989.
47. Riabowol, K., Draetta, G., Brizuela, L., Vandre, D., and Beach, D. The cdc2 kinase is a nuclear protein that is essential for mitosis in mammalian cells. Cell, 57: 393-401, 1989.
48. Maine, G. T., Sinha, P., and Tye, B. K. Mutants of *S. cerevisiae* defective in the maintenance of minichromosomes. Genetics, 106: 365-385, 1984.
49. Gibson, S. I., Surosky, R. T., and Tye, B. K. The phenotype of the minichromosome maintenance mutant mcm3 is characteristic of mutants defective in DNA replication. Mol Cell Biol, 10: 5707-5720, 1990.
50. Fujita, M., Yamada, C., Tsurumi, T., Hanaoka, F., Matsuzawa, K., and Inagaki, M. Cell cycle- and chromatin binding state-dependent phosphorylation of human MCM heterohexameric complexes. A role for cdc2 kinase. J Biol Chem, 273:17095-17101, 1998.
51. Cortez, D., Glick, G., and Elledge, S. J. Minichromosome maintenance proteins are direct targets of the ATM and ATR checkpoint kinases. Proc Natl Acad Sci USA, 101: 10078-10083, 2004.
52. Nichols, W. W., Murphy, D. G., Cristofalo, V. J., Toji, L. H., Greene, A. E., and Dwight, S. A. Characterization of a new human diploid cell strain, IMR-90. Science, 196:60-63, 1977.
53. Doye V, Hurt E C. Genetic approaches to nuclear pore structure and function. Trends Genet., 11:235-241, 1995.
54. Forsburg S L. The art and design of genetic screens: Yeast. *Nature Reviews.*, 2:659-668, 2001.
55. Morrison A, Johnson A L, Johnston L H, Sugino A. Pathway correcting DNA replication errors in *Saccharomyces cerevisiae*. *EMBO J.,* 12:1467-1473, 1993.
56. Jaffee E M, Hruban R H, Canto M, Kern S E. Focus on pancreas cancer. *Cancer Cell.,* 2002.
57. Bardeesy N, DePinho R A. Pancreatic cancer biology and genetics. *Nature Reviews Cancer.,* 2:897-909, 2002.

58. Napoli C, Lemieux C, Jorgensen R. Introduction of a Chimeric Chalcone Synthase Gene into Petunia Results in Reversible Co-Suppression of Homologous Genes in trans. *Plant Cell.,* 2:279-289, 1990.
59. Hunter C P. Gene silencing: shrinking the black box of RNAi. *Curr Biol.,* 10:R137-140, 2000.
60. Sharp P A. RNAi and double-strand RNA. *Genes Dev.,* 13:139-141, 1999.
61. Sharp P A. RNA Interference-2001. *Genes Dev.,* 15:485-490, 2001.
62. Elbashir S M, Harborth J, Lendeckel W, Yalcin A, Weber K, Tuschl T. Duplexes of 21-nucleotide RNAs mediate RNA interference in cultured mammalian cells. *Nature.,* 411:494-498, 2001.
63. Yu J Y, DeRuiter S L, Turner D L. RNA interference by expression of short-interfering RNAs and hairpin RNAs in mammalian cells. *Proc Natl Acad Sci USA.,* 99: 6047-6052, 2002.
64. Brummelkamp, T. R. Bernards, R. and Agami, R. 2002. A System for Stable Expression of Short Interfering RNAs in Mammalian Cells. *Science* 296: 550-553.
65. Lagos-Quintana M, Rauhut R, Lendeckel W, Tuschl T. Identification of novel genes coding for small expressed RNAs. *Science.,* 294:853-858, 2001.
66. Rozenblum E, Schutte M, Goggins M, Hahn S A, Panzer S, Zahurak M, Goodman S N, Sohn T A, Hruban R H, Yeo C J, Kern S E. Tumor-suppressive pathways in pancreatic carcinoma. *Cancer Res.,* 57:1731-1734, 1997.

---

We claim:

1. A method for identifying molecules that reduce viability of cancer cells with a specific pattern of a loss-of-function genetic alteration comprising the steps of:
   (a) creating a matched pair of isogenic cell lines that differ only by a "knock down" of expression of a single DPC4 gene wherein the "knock down" of expression of the single DPC4 gene is achieved by RNA interference performed by transfection or transformation of the cell line with a vector including therein in sequence: (1) DNA encoding a sequence selected from the group consisting of: 5'-ATGTCTATTACGAATACAC-3' (SEQ ID NO: 1);
   5'-TGCCCGTCTCTGGAGGTGG-3' (SEQ ID NO: 2);
   5'-ATCGTGCATCGACAGAGAC-3' (SEQ ID NO: 3);
   5'-GTAGGACTGCACCATACAC-3' (SEQ ID NO: 4);
   5'-GGTCAACTCTCCAATGTCC-3' (SEQ ID NO: 5);
   and 5'-AGCAAGGTTGCACATAGGC-3' (SEQ ID NO: 6); (2) DNA encoding a spacer sequence; and (3) DNA encoding the reverse complement of the selected sequence;
   (b) screening a molecular library against the matched pair of isogenic cell lines to identify a molecule that exerts a differential effect on cell survival such that cell survival is diminished to a greater extent in the cell line that exhibits "knock down" of expression of the single DPC4 gene; and
   (c) confirming the differential effect in a tumor model selected from the group consisting of an in vivo tumor model and an in vitro tumor model to identify the molecules.

2. The method of claim 1 wherein the RNA interference is performed by transient gene suppression using a synthetic RNA duplex produced by the vector of claim 1.

3. The method of claim 1 wherein the single DPC4 gene is a gene that affects the survival of a cancer cell selected from the group consisting of a pancreatic cancer cell and a colon cancer cell.

4. The method of claim 1 wherein the sequence is 5'-GTAGGACTGCACCATACAC-3' (SEQ ID NO: 4).

5. The method of claim 1 wherein the molecular library is selected from the group consisting of a small molecule library, a library of siRNA molecules, a library of antisense RNA molecules, a library of protein molecules, and a library of peptide molecules.

6. The method of claim 5 wherein the molecular library is a small molecule library.

7. The method of claim 6 wherein the small molecule library is selected from the group consisting of steroids, prostaglandins and analogues thereof, prostacyclins and analogues thereof, carbohydrates, receptor agonists, and receptor antagonists.

8. The method of claim 5 wherein the molecular library is a library of siRNA molecules.

9. The method of claim 5 wherein the molecular library is a library of antisense RNA molecules.

10. The method of claim 5 wherein the molecular library is a library of protein molecules.

11. The method of claim 10 wherein the library of protein molecules is a library of antibody molecules.

12. The method of claim 10 wherein the library of protein molecules is a library of receptor molecules.

13. The method of claim 5 wherein the molecular library is a library of peptide molecules.

14. The method of claim 1 wherein the molecules that are identified have therapeutic activity against pancreatic cancer.

15. The method of claim 1 wherein the molecules that are identified have therapeutic activity against colon cancer.

16. A method for identifying molecules that reduce viability of cancer cells with a specific pattern of a loss-of-function genetic alteration comprising the steps of:
   (a) creating a matched pair of isogenic cell lines that differ only by a "knock down" of expression of a single DPC4 gene that affects the survival of a cancer cell selected from the group consisting of a pancreatic cancer cell and a colon cancer cell wherein the "knock down" of expression of the single DPC4 gene is achieved by RNA interference performed by transfection or transformation of the cell line with a vector including therein in sequence: (1) DNA encoding a sequence selected from the group consisting of: 5'-ATGTCTATTACGAATACAC-3' (SEQ ID NO: 1); 5'-TGCCCGTCTCTGGAGGTGG-3'(SEQ ID NO: 2); 5'-ATCGTGCATCGACAGAGAC-3' (SEQ ID NO: 3); 5'-GTAGGACTGCACCATACAC-3' (SEQ ID NO: 4); 5'-GGTCAACTCTCCAATGTCC-3'(SEQ ID NO: 5); and 5'-AGCAAGGTTGCACATAGGC-3' (SEQ ID NO: 6); (2) DNA encoding a spacer sequence; and (3) DNA encoding the reverse complement of the selected sequence;

(b) screening a molecular library against the matched pair of isogenic cell lines to identify a molecule that exerts a differential effect on cell survival such that cell survival is diminished to a greater extent in the cell line that exhibits "knock down" of expression of the single gene; and (c) confirming the differential effect in a tumor model selected from the group consisting of an in vivo tumor model and an in vitro tumor model to identify the molecules.

* * * * *